United States Patent [19]
Roop et al.

[11] Patent Number: 6,057,298
[45] Date of Patent: May 2, 2000

[54] KERATIN K1 EXPRESSION VECTORS AND METHODS OF USE

[75] Inventors: Dennis R. Roop; Joseph A. Rothnagel; David A. Greenhalgh, all of Houston, Tex.; Stuart H. Yuspa, Bethesda, Md.

[73] Assignees: Baylor College of Medicine, Houston, Tex.; The United States of America as represented by the Department of Health and Human Services, Washington, D.C.

[21] Appl. No.: 08/452,872

[22] Filed: May 30, 1995

Related U.S. Application Data

[60] Division of application No. 08/147,777, Nov. 1, 1993, Pat. No. 5,914,265, which is a continuation-in-part of application No. 08/145,387, Oct. 29, 1993, abandoned, which is a continuation-in-part of application No. 07/876,289, Apr. 30, 1992, abandoned.

[51] Int. Cl.$^7$ .............................. A61K 48/00; C12N 5/10; C12N 15/09
[52] U.S. Cl. ........................ 514/44; 435/320.1; 435/371; 435/375
[58] Field of Search .............................. 435/320.1, 240.2, 435/6, 91.1, 7.2, 375, 325, 371; 514/44; 935/62, 52, 55, 56, 57, 34, 70, 71, 65; 424/93.1, 93.21; 536/24.5

[56] References Cited

U.S. PATENT DOCUMENTS

| | | | |
|---|---|---|---|
| 4,497,796 | 2/1985 | Salser et al. | 424/95 |
| 4,736,866 | 4/1988 | Leder et al. | 800/1 |

FOREIGN PATENT DOCUMENTS

| | | |
|---|---|---|
| 9318759 | 9/1993 | WIPO . |

OTHER PUBLICATIONS

Acsadi et al., "Human Dystrophin Expression in mdx Mice After Intramuscular Injection of DNA Constructs," 352 *Nature* 815, 1991.
Angel et al., "Phorbol Ester–Inducible Genes Contain a Common Cis Element Recognized by a TPA–Modulated Trans–Acting Factor," 49 *Cell* 729, 1987.
Asselineau et al., "Filaggrin Production by Cultured Human Epidermal Keratinocytes and Its Regulation by Retinoic Acid," 45 *Differentiation* 221, 1990.
Blessing et al., "Transgenic Mice as a Model to Study the Role of TGF–β–Related Molecules in Hair Follicles," 7 *Genes & Dev.* 204, 1993.
Blumenberg et al., "Regulation of Keratin Gene Expression: The Role of the Nuclear Receptors for Retinoic Acid, Thyroid Hormone, and Vitamin D3," 98 *J. Invest. Dermatol.* 42s, 1992.
Bos, "The ras Gene Family and Human Carcinogenesis," 195 *Mutant Res.* 255, 1988.
Bradford, "A Rapid and Sensitive Method for the Quantitation of Microgram Quantities of Protein Utilizing the Principle of Protein–Dye Binding," 72 *Anal. Biochem.* 248, 1976.
Broker et al., "A Molecular Portrait of Human Papillomavirus Carcinogenesis", pp. 197–208, In: Molecular Diagnostics of Human Cancer, Cancer Cells 7, Cold Spring Harbor, N.Y. (1989).
Christophers et al., "Cellular Architecture of the Stratum Corneum," 56 *J. Invest. Dermatol.* 165, 1971.
Clark et al., "Epidermal Growth Factor Regulates the Expression of its Own Receptor," 82 *Proc. Natl. Acad. Sci. USA* 8374, 1985.
Cotsarelis et al., "Label–Retaining Cells Reside in the Bulge Area of Pilosebaceous Unit: Implications for Follicular Stem Cells, Hair Cycle, and Skin Carcinogenesis," 61 *Cell* 1329, 1990.
Cripe et al., "Transcriptional Activation of the Human Papillomavirus–16 P97 Promoter by an 88–Nucleotide Enhancer Containing Distinct Cell–Dependent and AP–1–Responsive Modules," 2 *New Biologist* 450, 1990.
Dale et al., "Assembly of Stratum Corneum Basic Protein and Keratin Filaments in Macrofibrils," 276 *Nature* 729, 1978.
Dale and Holbrook, "Developmental Expression of Human Epidermal Keratins and Filaggrin," In: Current Topics in Developmental Biology, pp. 127–151, 1987.
Dhar et al., "Nucleotide Sequence of the p21 Transforming Protein of Harvey Murine Sarcoma Virus," 217 *Science* 934, 1982.
Dhawan et al., "Systemic Delivery of Human Growth Hormone by Injection of Genetically Engineered Myoblasts," 254 *Science* 1509, 1991.
Dignam et al., "Accurate Transcription Initiation by RNA Polymerase II in a Soluble Extract from Isolated Mammalian Nuclei," 11 *Nucleic Acids Res.* 1475, 1983.
Dotto et al., "c–myc and c–fos Expression in Differentiating Mouse Primary Keratinocytes," 5 *EMBO J.* 2853, 1986.
Earp et al., "Epidermal Growth Factor (EGF) Stimulates EGF Receptor Synthesis," 261 *J. Biol. Chem.* 4777, 1986.
Evans, "The Steroid and Thyroid Hormone Receptor Superfamily," 240 *Science* 889, 1988.
Fisher et al., "Patterns of Epithelial Expression of Fos Protein Suggest Important Role in the Transition from Viable to Cornified Cell During Keratinization," 3 *Development* 253, 1991.
Fisher et al., "Localization of Profilaggrin mRNA in Newborn Rat Skin by In Situ Hybridization," 88 *J. Invest. Dermatol.* 661, 1987.

(List continued on next page.)

*Primary Examiner*—Karen M. Hauda
*Attorney, Agent, or Firm*—Lyon & Lyon LLP

[57] ABSTRACT

A keratin K1 vector for expression of a nucleic acid sequence in an epidermal cell. The vector includes a 5' flanking region which includes necessary sequences for expression of a nucleic acid cassette, a keratin K1 3' flanking region which regulates expression of a nucleic acid sequence, predominantly in the epidermis, and a linker which connects the 5' flanking region to a nucleic acid. The linker has a position for inserting a nucleic acid cassette. The linker does not contain the coding sequence of a gene that the linker is naturally associated with. That is, the linker is not the normal gene associated with the 5' and 3' regions.

23 Claims, 7 Drawing Sheets

OTHER PUBLICATIONS

Fuchs and Green, "Changes in Keratin Gene Expression during Terminal Differentiation of the Keratinocyte," 19 *Cell* 1033, 1980.

Fuchs and Green, "Regulation of Terminal Differentiation of Cultured Human Kerkatinocytes by Vitamin A," 25 *Cell* 617, 1981.

Glass et al., "Positive and Negative Regulation of Gene Transcription by a Retinoic Acid–Thyroid Hormone," 59 *Cell* 697, 1989.

Gorman et al., "Recombinant Genomes Which Express Chloramphenicol Acetyltransferase in Mammalian Cells," 2 *Mol. Cell. Biol.* 1044, 1982.

Greenhalgh et al., "Induction of Epidermal Hyperplasia, Hyperkeratosis, and Papillomas in Transgenic Mice by a Targeted v–Ha–ras Oncogene," 7 *Mol. Carcinog.* 99, 1993.

Greenhalgh et al., "Hyperplasia, Hyperkeratosis and Benign Tumor Production in Transgenic Mice by a Targeted v–fos Oncogene Suggest a Role for fos in Epidermal Differentiation and Neoplasia," 8 *Oncogene* 2145, 1993.

Greenhalgh et al., "Two Oncogenes, v–fos and v–ras, Cooperate to Convert Normal Keratinocytes to Squamous Cell Carcinoma," 87 *Proc. Natl. Acad. Sci. USA* 643, 1990.

Greenhalgh and Yuspa, "Malignant Conversion of Murine Squamous Papilloma Cell Lines by Transfection with the fos Oncogene," 1 *Mol. Carcinogen.* 134, 1988.

Harding et al., "Histidine–rich Proteins (Filaggrins): Structural and Functional Heterogeneity during Epidermal Differentiation," 170 *J. Mol. Biol.* 651, 1983.

Harper et al., "Expression of Transfected DNA by Primary Murine Keratinocytes," 91 *J. Invest. Dermatol.* 150, 1988.

Haydock et al., "The Repetitive Structure of the Profilaggrin Gene as Demonstrated Using Epidermal Profilaggrin cDNA," 261 *J. Biol. Chem.* 12520, 1986.

Hennings et al., "Calcium Regulation of Growth and Differentiation of Mouse Epidermal Cells in Culture," 19 *Cell* 245, 1980.

Higuchi, "Using PCR to Engineer DNA," In: PCR Technology, Principles and Applications for DNA Amplification (Erlich, H.A. ed) pp. 61–70, Stockton Press, New York (1989).

Hogan et al., Manipulating the Mouse Embryo. A Laboratory Manual, Cold Spring Harbor, N.Y., Cold Spring Harbour Laboratory (1986).

Hohl et al., "Transcription of the Human Loricrin Gene In Vitro is Induced by Calcium and Cell Density and Suppressed by Retinoic Acid," 96 *J. Invest. Dermatol.* 414, 1991.

Hosomi et al., "Regulation of Terminal Differentiation of Cultured Mouse Epidermal Cells by $1\alpha,25$–Dihydroxyvitamin $D_3$", 113 *Endocrinology* 1950, 1983.

Huff et al., "Identification of Control Elements 3' to the Human Keratin 1 Gene that Regulate Cell Type and Differentiation–specific Expression," 268(1) *J. Biol. Chem.* 377, 1993.

Huitfeldt et al., "Altered Regulation of Growth and Expression of Differentiation–Associated Keratins in Benign Mouse Skin Tumors," 12 *Carcinogen.* 2063, 1991.

Imamato et al., "Evidence for Autocrine/Paracrine Growth Stimulation by Transforming Growth Factor–$\alpha$ During the Process of Skin Tumor Promotion," 4 *Mol. Carcinog.* 52, 1991.

Iversen et al., "Kinetics of Cell Renewal, Cell Migration and Cell Loss in the Hairless Mouse Dorsal Epidermis," 1 *Cell Tissue Kinet.* 351, 1968.

Johnson et al., "Structure of a Gene for the Human Epidermal 67–kDa Keratin," 82 *Proc. Natl. Acad. Sci. USA* 1896, 1985.

Knapp et al., "Three cDNA Sequences of Mouse Type I Keratins," 262 *J. Biol. Chem.* 938, 1987.

Kopan et al., "Retinoids as Important Regulators of Terminal Differentiation: Examining Keratin Expression in Individual Epidermal Cells at Various Stages of Keratinization," 105 *J. Cell Biol.* 427, 1987.

Krieg et al., "Organization of a Type I Keratin Gene," 260 *J. Biol. Chem.* 5867, 1985.

Kudlow et al., "Epidermal Growth Factor Stimulates the Synthesis of Its Own Receptor in a Human Breast Cancer Cell Line," 261 *J. Biol. Chem.* 4134, 1986.

Kulkarni et al., "Transforming Growth Factor $\beta 1$ Null Mutation in Mice Causes Excessive Inflammatory Response and Early Death," 90 *Proc. Natl. Acad. Sci. USA* 770, 1993.

Leask et al., "Regulation of a Human Epidermal Keratin Gene: Sequences and Nuclear Factors Involved in Keratinocyte–Specific Transcription," 4 *Genes Develop.* 1985, 1990.

Lee et al., "Activation of Transcription by Two Factors that Bind Promoter and Enhancer Sequences of the Human Metallothionein Gene and SV40," 325 *Nature* 368, 1987.

Lersch et al., "Sequence and Expression of a Type II Keratin, K5, in Human Epidermal Cells," 8 *Mol. Cell Biol.* 486, 1988.

Lindahl et al., "Cellular Aspects of Gene Therapy," In: Growth Factors in Health and Disease, (B. Westermark, C. Betsholtz, B. Hokfelt, eds.), Excerpta Medica, Amsterdam, New York, Oxford, p. 383, 1990.

Luetteke et al., "TGF$\alpha$ Deficiency Results in Hair Follicle and Eye Abnormalities in Targeted and Waved–1 Mice," 73 *Cell* 263, 1993.

MacGregor et al., "Use of *E.coli* lacZ ($\beta$–Galactosidase) as a Reporter Gene," In: Methods in Molecular Biology, vol. 7, pp. 217–235 (1991).

MacKenzie et al., "Relationship between Mitosis and the Ordered Structure of the Stratum Corneum in Mouse Epidermis," 226 *Nature* 653, 1970.

Mack and Laimins, "A Keratinocyte–Specific Transcription Factor, KRF–1, Interacts with AP–1 to Activate Expression of Human Papillomavirus Type 18 in Squamous Epithelial Cells," 88 *Proc. Natl. Acad. Sci. USA* 9102, 1991.

Malmqvist et al., "Proton and Electron Microprobe Analysis of Human Skin," 231 *Nucl. Instrum. Methods Phys. Res.* 611, 1984.

Maniatis et al., Molecular Cloning, A Laboratory Manual, Cold Spring Harbor, New York, Cold Spring Harbor Laboratory (1982).

Mann et al., "Mice with a Null Mutation of the TGF$\alpha$ Gene Have Abnormal Skin Architecture, Wavy Hair, and Curly Whiskers and Often Develop Corneal Inflammation," 73 *Cell* 249, 1993.

Marchuk et al., "Complete Sequence of a Gene Encoding a Human Type I Keratin: Sequences Homologous to Enhancer Elements in the Regulatory Region of the Gene," 82 *Proc. Natl. Acad. Sci. USA* 1609, 1985.

Matoltsky, "Desmosomes, Filaments, and Keratohyalin Granules: Their Role in the Stabilization and Keratinization of the Epidermis," 65 *J. Invest. Dermatol.* 127, 1975.

Matsumoto et al., "Growth–Inhibitory Effects of 1,25–Dihydroxyvitamin $D_3$ on Normal Human Keratinocytes Cultured in Serum–Free Medium," 166 *Biochem. Biophys. Res. Commun.* 916, 1990.

Mehrel et al., "Identification of a Major Keratinocyte Cell Envelope Protein, Loricrin," 61 *Cell* 1103, 1990.

Menon et al., "Ionic Calcium Reservoirs in Mammalian Epidermis: Ultrastructural Localization by Ion–Capture Cytochemistry," 84 *J. Invest. Dermatol.* 508, 1985.

Morgan et al., "Expression of an Exogenous Growth Hormone Gene by Transplantable Human Epidermal Cells," 237 *Science* 1476, 1987.

Nanney et al., "Epidermal Growth Factor Receptors in Idiopathic and Virally Induced Skin Diseases," 140 *Am. J. Path.* 915, 1992.

Nanney et al., "Comparison of Epidermal Growth Factor Binding and Receptor Distribution in Normal Human Epidermis and Epidermal Appendages," 83 *J. Invest. Dermatol.* 385, 1984.

Nischt et al., "Aberrant Expression During Two–Stage Mouse Skin Carcinogenesis of a type I 47–kDa Keratin, K13, Normally Associated with Terminal Differentiation of Internal Stratified Epithelia," 1 *Mol. Carcinogen.* 96, 1988.

Offord and Beard, "A Member of the Activator Protein 1 Family Found in Keratinocytes but Not in Fibroblasts Required for Transcription from a Human Papillomavirus Type 18 Promoter," 64 *J. Virol.* 4792, 1990.

Oshima et al., "Activation of an Intron Enhancer Within the Keratin 18 Gene by Expression of c–fos and c–jun in Undifferentiated F9 Embryonal Carcinoma Cells," 4 *Genes Develop.* 835, 1990.

Palmiter and Brinster, "Germ–Line Transformation of Mice," 20 *Ann. Rev. Genet.* 465, 1986.

Pastorcic et al., "Control of Transcription Initiation In Vitro Requires Binding of a Transcription Factor to the Distal Promoter of the Ovalbumin Gene," 6 *Mol. Cell. Biol.* 2784, 1986.

Pierceall et al., "Presence of Human Papilloma Virus Type 16 DNA Sequences in Human Nonmelanoma Skin Cancers", 97 *J. Invest. Dermatol.* 880, 1991.

Pierceall et al., "Ras Gene Mutation and Amplification in Human Nonmelanoma Skin Cancers", 4 *Mol. Carcinog.* 196, 1991.

Pirisi et al., "Transformation of Human Fibroblasts and Keratinocytes with Human Papillomavirus Type 16 DNA," 61(4) *J. Virology* 1061, 1987.

Potten, "Stem Cells in Epidermis from the Back of the Mouse," In: *Stem Cells: Their Identification and Characterisation* (C.S. Potten ed.), Churchill Livingstone, Edinburgh London Melbourne and New York, pp. 200–232 (1983).

Régnier et al., "Onset of Epidermal Differentiation in Rapidly Proliferating Basal Keratinocytes," 87 *J. Inves. Dermatol.* 472, 1986.

Régnier and Darmon, "1,25–Dihydroxyvitamin $D_3$ Stimulates Specifically the Last Steps of Epidermal Differentiation of Cultured Human Keratinocytes," 47 *Differentiation* 173, 1991.

Rice and Green, "The Cornified Envelope of Terminally Differentiated Human Epidermal Keratinocytes Consists of Cross–Linked Protein," 11 *Cell* 417, 1977.

Risse et al., "Asymmetrical Recognition of the Palindromic AP1 Binding Site (TRE) by Fos Protein Complexes," 8 *EMBO J.* 3825, 1989.

Roberts et al., "Transforming Growth Factors: Isolation of Polypeptides from Virally and Chemically Transformed Cells by Acid/Ethanol Extraction," 77 *Proc. Natl. Acad. Sci., USA* 3494, 1980.

Roop et al., "Sequential Changes in Gene Expression During Epidermal Differentiation," In: The Biology of Wool and Hair (Rogers, G.E., Reis, P.J., Ward, K.A., and Marshall, R.C. eds), pp. 311–324, Chapman and Hall, New York (1988).

Roop et al., "Epidermal Differentiation and Its Modulation by Retinoids," In: Pharmacology of Retinoids in the Skin. Pharmacol Skin. (Reichert, U., and Shroot, B., eds.), vol. 3, pp. 1–7, Karger, Basal (1989).

Roop et al., "Transcriptional Control of High Molecular Weight Keratin Gene Expression in Multistage Mouse Skin Carcinogenesis," 48 *Cancer Res.* 3245, 1988.

Roop et al., "Regulated Expression of Differentiation–Associated Keratins in Cultured Epidermal Cells Detected by Monospecific Antibodies to Unique Peptides of Mouse Epidermal Keratins," 35 *Differentiation* 143, 1987.

Roop et al., "Keratin Gene Expression in Mouse Epidermis and Cultured Epidermal Cells," 80 *Proc. Natl. Acad. Sci. USA* 716, 1983.

Rosenthal et al., "A Human Epidermal Differentiation–specific Keratin Gene is Regulated by Calcium but not Negative Modulators of Differentiation in Transgenic Mouse Keratinocytes," 2 *Cell Growth and Differentiation* 107, 1991.

Rothnagel et al., "The Gene for Mouse Epidermal Filaggrin Precursor," 262 *J. Biol. Chem.* 15643, 1987.

Rothnagel et al., "Identification of a Calcium–Inducible, Epidermal–Specific Regulatory Element in the 3'–Flanking Region of the Human Keratin 1 Gene," 101 *J. Invest. Dermatol.* 506, 1993.

Ryseck and Bravo, "c–JUN, JUN B, and JUN D Differ in Their Binding Affinities to AP–1 and CRE Consensus Sequences: Effect of FOS Proteins," 6 *Oncogene* 533, 1991.

Schweizer et al., "Sequential Expression of mRNA–Encoded Keratin Sets in Neonatal Mouse Epidermis: Basal Cells with Properties of Terminally Differentiating Cells," 37 *Cell* 159, 1984.

Sedman et al., "The Full–Length E6 Protein of Human Papillomavirus Type 16 Has Transforming and trans–Activating Activities and Cooperates with E7 to Immortalize Keratinocytes in Culture", 65 *J. Virol* 4860, 1991.

Seedorf et al., "Human Papillomavirus Type 16 DNA Sequence," 145 *Virology* 181, 1985.

Sellheyer et al., "Inhibition of Skin Development by Overexpression of Transforming Growth Factor $\beta_1$ in the Epidermis of Transgenic Mice," 90 *Proc. Natl. Acad. Sci. USA* 5237, 1993.

Shull et al., "Targeted Disruption of the Mouse Transforming Growth Factor–$\beta$1 Gene Results in Multifocal Inflammatory Disease," 359 *Nature* 693, 1992.

Smeyne et al., "Fos–lacZ Transgenic Mice: Mapping Sites of Gene Induction in the Central Nervous System," 8 *Neuron* 13, 1992.

Smith et al., "Differential Keratin Gene Expression in Developing, Differentiating, Preneoplastic, and Neoplastic Mouse Mammary Epithelium," 1 *Cell Growth and Diff.* 161, 1990.

Steinert et al., "The Molecular Biology of Intermediate Filaments," 42 *Cell* 411, 1985.

Steinert et al., "Amino Acid Sequences of Mouse and Human Epidermal Type II Keratins of $M_r$ 67,000 Provide a Systematic Basis for the Structural and Functional Diversity of the End Domains of Keratin Intermediate Filament Subunits," 260 *J. Biol. Chem.* 7142, 1985.

Storey and Banks, "Human Papillomavirus Type 16 E6 Gene Cooperates with EJ–ras to Immortalize Primary Mouse Cells," 8 *Oncogene* 919, 1993.

Stumpf et al., "Topographical and Developmental Studies on Target Sites of 1,25 $(OH)_2$ Vitamin $D_3$ in Skin," 238 *Cell Tissue Res.* 489, 1984.

Tamai et al., "Sequence of the Endo A Gene Encoding Mouse Cytokeratin and Its Methylation State in the CpG–rich Region," 104 *Gene* 169, 1991.

Tennant et al., "Prediction of Chemical Carcinogenicity in Rodents from In Vitro Genetic Toxicity Assays," 236 *Science* 933, 1987.

Teumer et al., "Human Growth Hormone in the Blood of Athymic Mice Grafted with Cultures of Hormone–Secreting Human Keratinocytes," 4 *FASEB J.* 3245 (1990).

Thierry et al., "Two AP1 Sites Binding JunB Are Essential for Human Papillomavirus Type 18 Transcription in Keratinocytes," 66 *J. Virol.* 3740, 1992.

Tomic et al., "Nuclear Receptors for Retinoic Acid and Thyroid Hormone Regulate Transcription of Keratin Genes," 1 *Cell Reg.* 965, 1990.

Tyner et al., "The Sequences of a Type II Keratin Gene Expressed in Human Skin: Conservation of Structure Among All Intermediate Filament Genes," 82 *Proc. Natl. Acad. Sci. USA* 4683, 1985.

Tyner and Fuchs, "Evidence for Posttranscriptional Regulation of the Keratins Expressed during Hyperproliferation and Malignant Transformation in Human Epidermis," 103 *J. Cell Biol.* 1945, 1986.

Umesono et al., "Direct Repeats as Selective Response Elements for the Thyroid Hormone, Retinoic Acid, and Vitamin $D_3$ Receptors," 65 *Cell* 1255, 1991.

Vahlquist et al., "Vitamin A and β–Carotene Concentrations at Different Depths of the Epidermis: A Preliminary Study in the Cow Snout," 92 *Upsala J. Med. Sci.* 253, 1987.

Weiss et al., "Monoclonal Antibody Analysis of Keratin Expression in Epidermal Diseases: A 48– and 56–kdalton Keratin as Molecular Markers for Hyperproliferative Keratinocytes," 98 *J. Cell Biol.* 1397, 1984.

Woodcock–Mitchell et al., "Immunolocalization of Keratin Polypeptides in Human Epidermis Using Monoclonal Antibodies," 95 *J. Cell Biol.* 580, 1982.

Woodworth et al., "Recombinant Retrovirus Encoding Human Papillomavirus Type 18 E6 and E7 Genes Stimulate Proliferation and Delay Differentiation of Human Keratinocytes Early After Infection", 7 *Oncogene* 619, 1992.

Yoneda et al., "The Human Loricrin Gene," 267(25) *J. Biol. Chem.* 18060, 1992.

Yoneda et al., "Structure of the Human Loricrin Gene: Linkage at 1q21 with Profilaggrin and Involucrin Genes," 39(2) *Clin. Res.* 496A, 1991.

Yuspa et al., "Expression of Murine Epidermal Differentiation Markers Is Tightly Regulated by Restricted Extracellular Calcium Concentrations In Vitro," 109 *J. Cell Biol.* 1207, 1989.

Yuspa et al., "Epidermal Cell Culture", 12(1) *Transplantation Proc.* 114, 1980.

Yuspa and Harris, "Altered Differentiation of Mouse Epidermal Cells Treated with Retinyl Acetate In Vitro," 86 *Exp. Cell Res.* 95, 1974.

Orkin et. al. "Report and Recommendations of the Panel to Assess the NIH Investment Research on Gene Therapy," NIH Publication, Dec. 7, 1995.

Weiss, R. "Upping the Antisense Ante," Science News, vol. 139:108–109, Feb. 16, 1991.

Rojanasakul, Y. "Antisense oligonucleotide therapeutics: drug delivery and targeting," Advanced Drug Delivery Reviews, vol. 18: 115–131, Jan. 1996.

Stull et. al. "Antigene, Ribozyme and Aptamer Nucleic Acid Drugs: Progress and Prospects," Pharmaceutical Research, vol. 12 (4): 465–483, Apr. 1995.

Doeberitz et al. "Correlation of Modified Human Papilloma Virus Early Gene Expression with Altered Growth Properties in C4–1 Cervical Carcinoma Cells," Cancer Research, vol. 48: 3780–3786, Jul. 1, 1988.

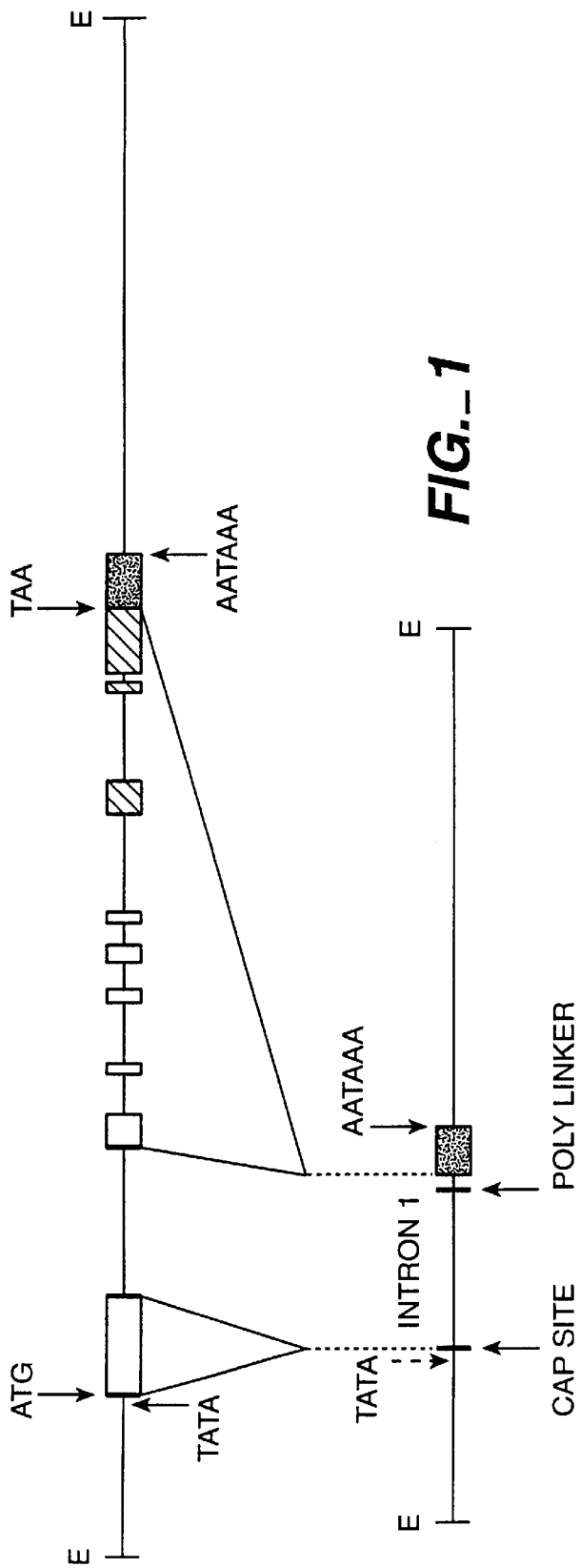
FIG._1
FIG._10

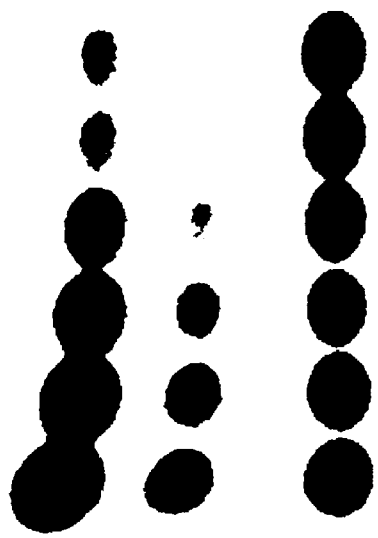
FIG._2
TGGCCTTGAG$_{10}$GGAGATGATT$_{20}$CACTCTCCTT$_{30}$CACAGAAGAG$_{40}$CTGACCTCTG$_{50}$GGGTCAACAG$_{60}$ATATAGCACC$_{70}$
[D3]: 0  $10^{-10}$M  $10^{-9}$M  $10^{-8}$M  $10^{-7}$M  $10^{-6}$M

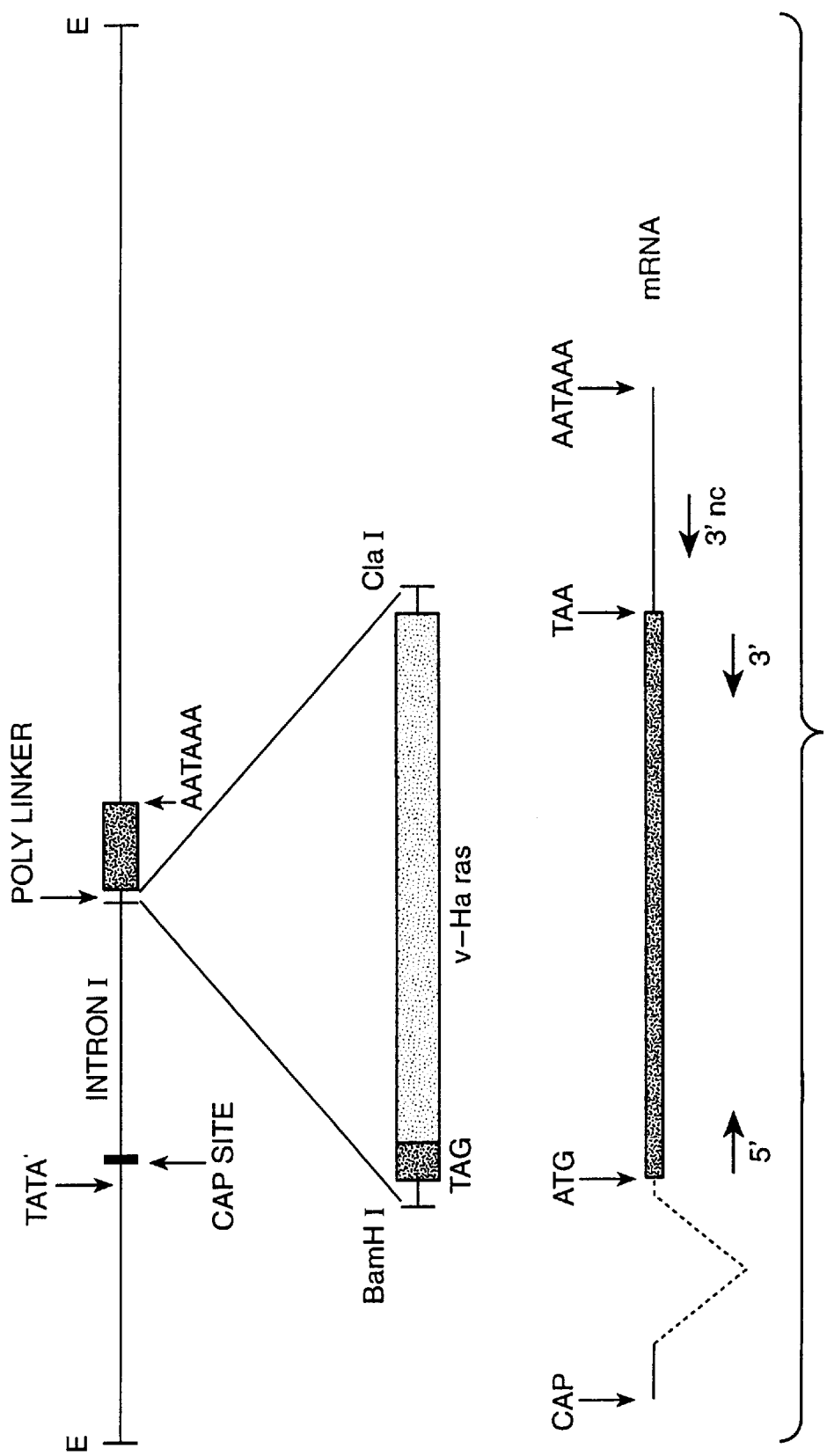
FIG._3

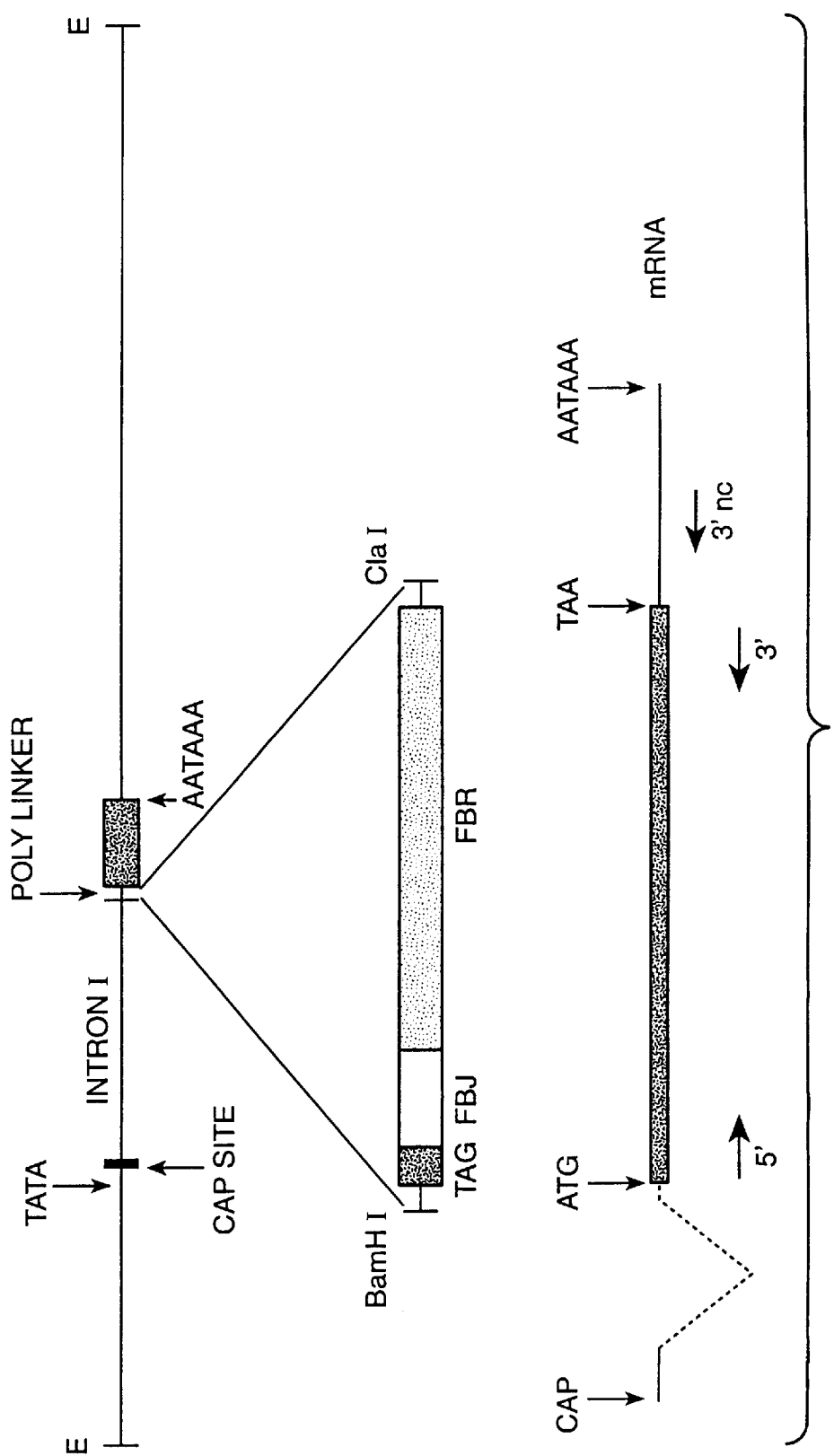
FIG._4

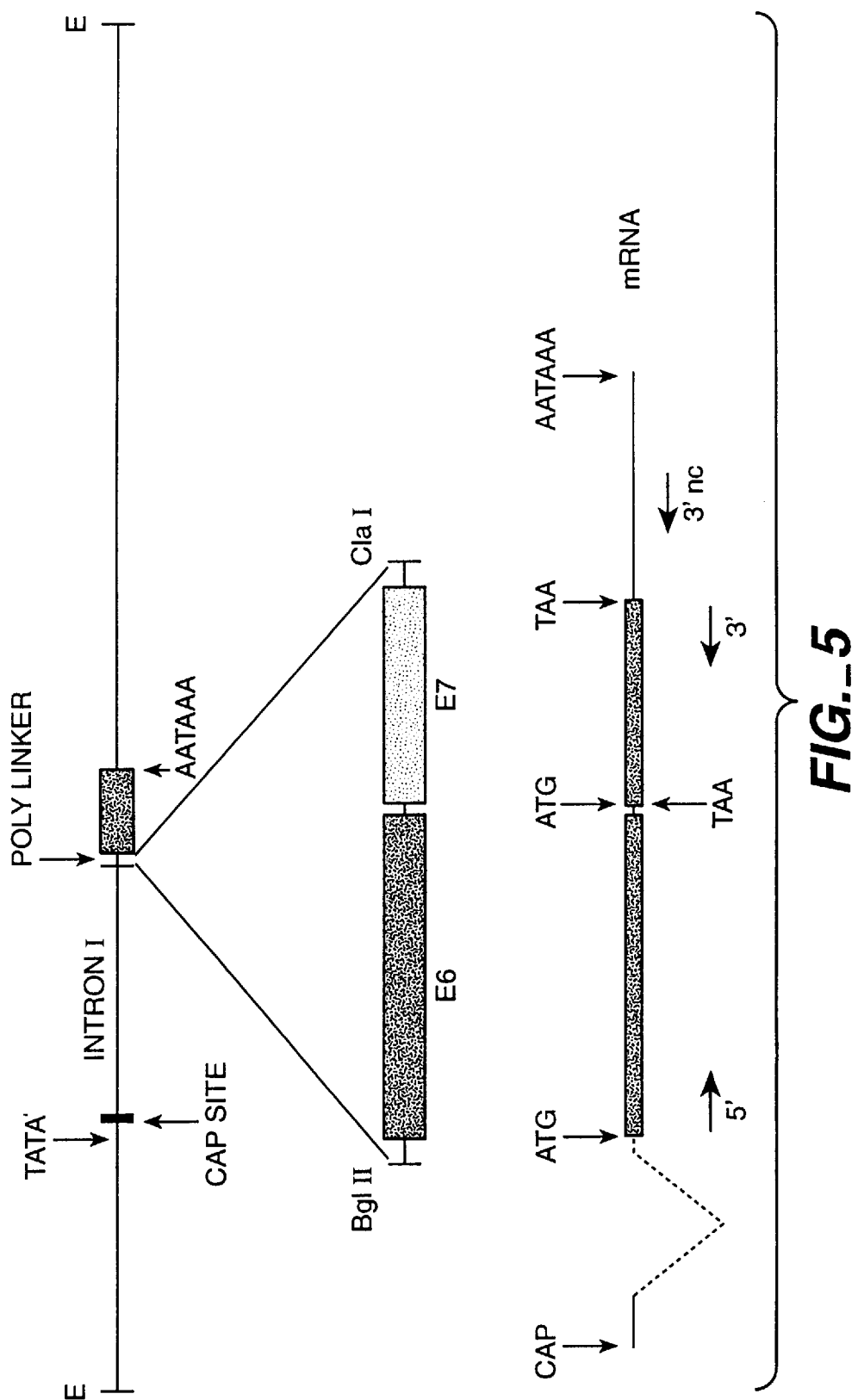
FIG._5

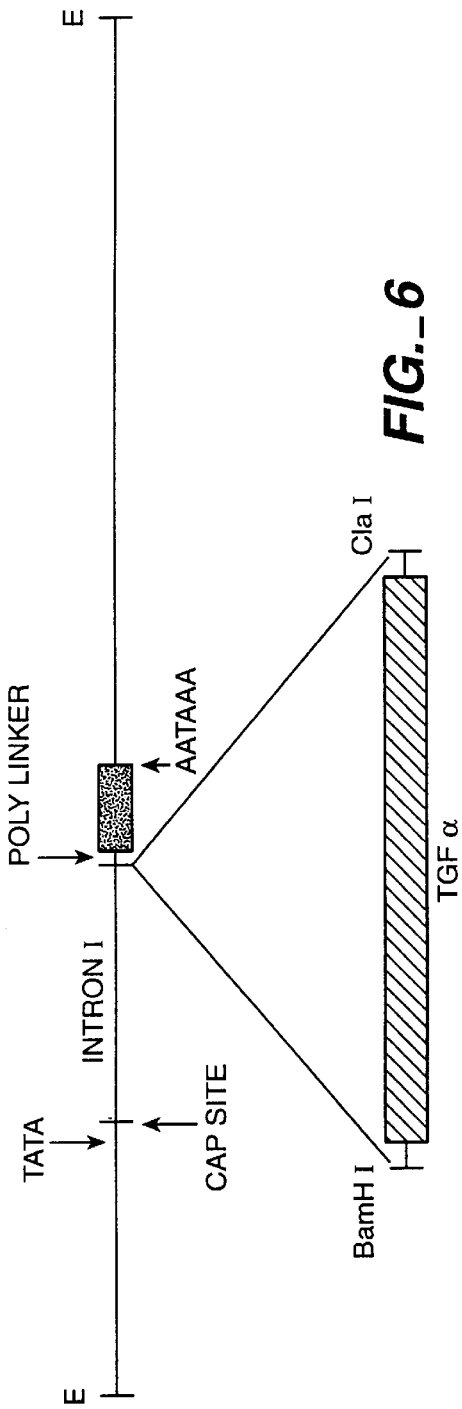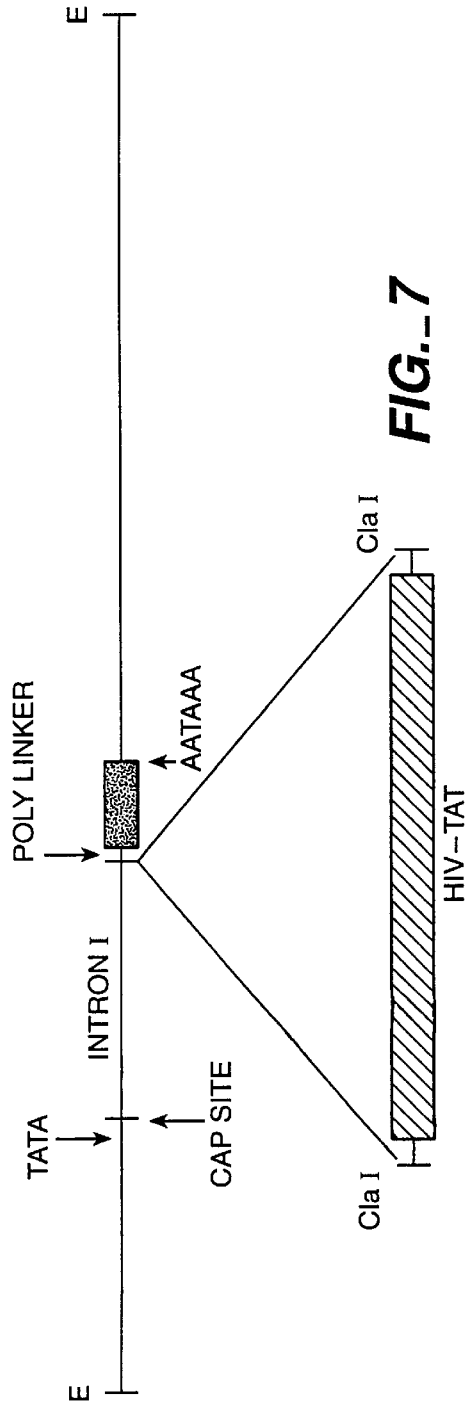

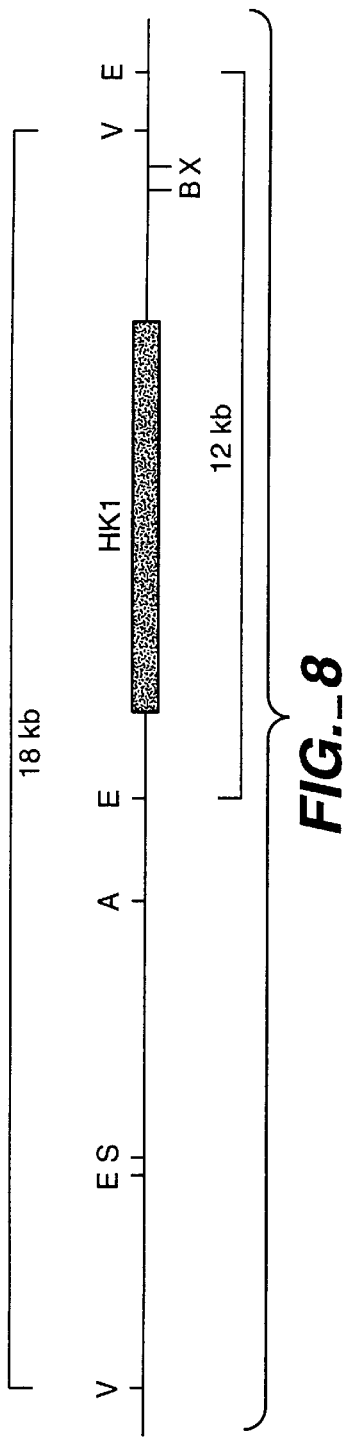
FIG._8
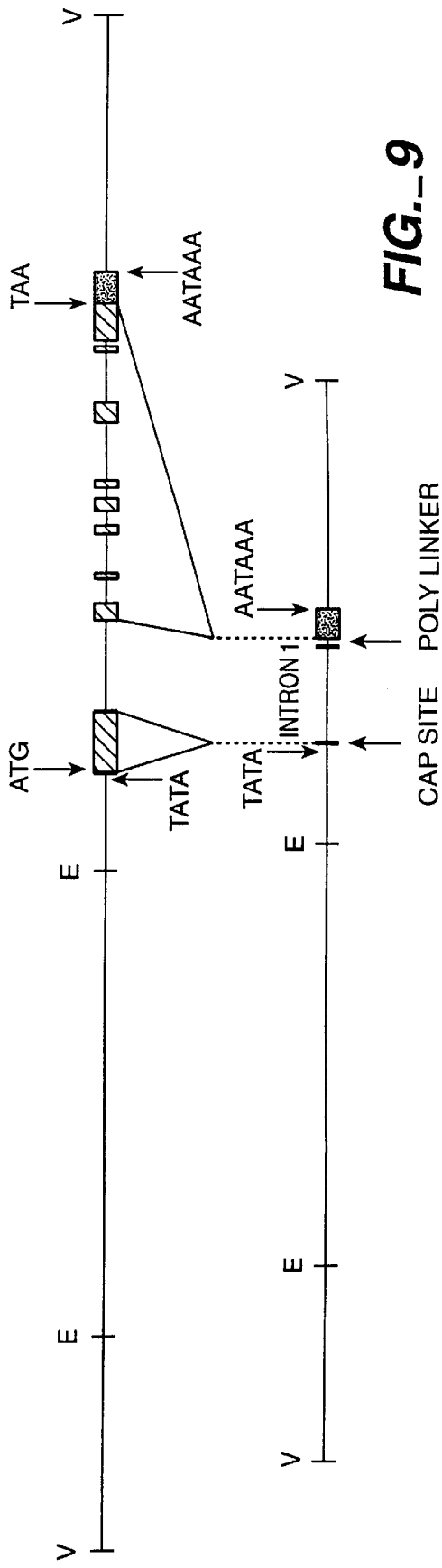
FIG._9

KERATIN K1 EXPRESSION VECTORS AND METHODS OF USE

RELATED APPLICATION

This application is a divisional of application Ser. No. 08/147,777, Roop et al., filed Nov. 1, 1993, U.S. Pat. No. 5,914,265, entitled "Keratin K1 Expression Vectors and Methods of Use; which is a continuation-in-part of Roop et al., Ser. No. 08/145,387 filed Oct. 29, 1993, now abandoned, entitled "Keratin K1 Expression Vectors and Methods of Use," which is also a continuation-in-part of Roop et al., U.S. patent application Ser. No. 07/876,289, filed Apr. 30, 1992, now abandoned, entitled "Development of a Vector to Target Gene Expression to the Epidermis of Transgenic Animals," the whole of which (including drawings) are all hereby incorporated by reference. This divisional application is also related to Roop et al., U.S. Ser. No. 07/876,286, filed Apr. 30, 1992, now abandoned, entitled "Constitutive and Inducible Epidermal Vector Systems," and its continuation-in-part application by Roop et al., Ser. No. 08/145,388, entitled "Specific Expression Vectors and Methods of Use," filed Oct. 29, 1993, now abandoned, and its continuation-in-part application by Roop et al., Ser. No. 08/146,930, entitled "Specific Expression Vectors and Methods of Use," filed Nov. 1, 1993, U.S. Pat. No. 5,958,764, all (including drawings) hereby incorporated by reference herein.

The invention was partially supported by a grant from the United States Government under HD25479, AI30283 and CA52607 awarded by the National Institutes of Health. Further, this work was partially performed at the National Institutes of Health in the Laboratory of Cellular Carcinogenesis and Tumor Promotion, Division of Cancer Etiology, National Cancer Institute. The U.S. government may have rights in the invention.

BACKGROUND OF THE INVENTION

This invention relates to gene therapy to cause expression of genes within the epidermis or epidermal cells.

The skin is the largest organ in the human body. The skin consists of two layers, the epidermis and the dermis. The outer layer is the epidermis which is composed of four histologically defined layers, each of which represent a distinct stage of differentiation of the epidermal keratinocyte. The innermost layer is the stratum germinativum (or basal layer) consisting of continuously dividing cells. The next two layers are the stratum spinosum (or spinous layer) and the stratum granulosum (or granular layer). The outermost layer is the stratum corneum consisting of dead cells whose cytoplasm has been entirely replaced by keratin. (Iverson, et al., Cell Tissue Kinet., Vol. 1, pp. 351–367 (1968); MacKenzie, et al., Nature, Vol. 226, pp. 653–655 (1970)).

The dermis lies under the epidermis and is separated from it by a basement membrane. The dermis is a thick layer of living tissue consisting mainly of a loose connective tissue within which are blood capillaries, lymph vessels, sensory nerve endings, sweat glands and their ducts, hair follicles, sebaceous gland and smooth muscle fibers.

The epidermis is a continuously regenerating epithelium. Keratinocytes are the major cell type of the epidermis and arise from the basal cells in the basal layer. The basal cells consist of metabolically active cells. The basal cells are the cells which undergo mitosis. (Potten, In Stem Cells: Their Identification and Characterization, pp. 200–232 (1983)).

Upon commitment to differentiation, the basal cells lose their proliferative potential and migrate to the spinous layer. With further maturation these cells enter the granular layer and finally terminate as cornified squames in the stratum corneum before being sloughed into the environment. (Matoltsky, J. Invest. Dermatol., Vol 65, pp. 127–142 (1975)).

During the regeneration process for the differentiated epidermal cells, the cells express a succession of different homologous keratin genes. The keratin produced by the differentiating cells is an insoluble fibrous protein. Keratins are the most abundant proteins synthesized in the epidermal cells and changes in the keratin expression patterns occur during differentiation.

The degree of differentiation can be defined biochemically by the expression of marker proteins that characterize each stage. (Matoltsky, J. Invest. Dermatol., Vol. 65, pp. 127–42 (1975)). For instance, basal keratinocytes express keratins K5 and K14 as major products. (Woodcock-Mitchell, et al., J. Cell Biol., Vol. 95, pp. 580–88 (1982)). These proteins assemble into 10 nm filaments and together with microtubules and microfilaments, comprise the cytoskeleton of epidermal cells. (Steinert, P. M., et al., Cell, Vol. 42, pp. 411–19 (1985)).

One of the earliest changes associated with the commitment to differentiation and migration into the spinous layer is the induction of another differentiation-specific pair of keratins, K1 and K10. Once a cell is committed to the differentiation pathway the cells downregulate the genes for K5 and K14, and express the genes for the differentiation-specific keratins, K1 and K10. (Woodcock-Mitchell, et al., J. Cell Biol., Vol. 95, pp. 580–88 (1982); Roop, et al., Proc. Natl. Acad. Sci., USA, Vol. 80, pp. 716–20 (1983); Schweizer, et al., Cell, Vol. 37, pp. 159–170 (1984)). Transcription of K1 and K10 is restricted to the spinous layer cells. The expression of K1 precedes K10 and is one of the earliest in keratinocyte differentiation. Occasionally, K1 can be observed in the occasional basal cell that has already ceased mitotic activity and is about to migrate into the spinous layer. (Huitfeld, et al., Carcinogenesis, Vol. 12, pp. 2063–2067 (1991)). When the cells mature into granular layer cells, the genes for K1 and K10 are downregulated. At this point, other genes, notably loricrin and filaggrin, are induced. (Dale, B. A., et al., Nature, Vol. 276, pp. 729–731 (1978); Harding, C. R., et al., J. Mol. Biol., Vol. 170, pp. 651–673 (1983)).

Genes or cDNAs encoding the major keratins expressed in epidermal cells have been cloned, such as K5 (Lersch, et al., Mol. and Cell Biol., Vol. 8, pp. 486–493 (1988)), K14 (Marchuk, et al., Proc. Natl. Acad. Sci., USA, Vol. 82, pp. 1609–1613 (1985); Knapp, et al., J. Biol. Chem., Vol. 262, pp. 938–945 (1987); Roop, et al., Cancer Res., Vol. 48, pp. 3245–3252 (1988)), K1 (Steinert, et al., J. Biol. Chem., Vol. 260, pp. 7142–7149 (1985)), and K10 (Krieg, et al., J. Biol. Chem., Vol. 260, pp. 5867–5870 (1985)). In addition, human K6 cDNA has been cloned. (Tyner, et al., Proc. Natl. Acad. Sci., USA, Vol. 82, pp. 4683–4687 (1985)).

Northern blot analysis and in situ hybridization studies suggest that keratin genes K5 and K14 are predominantly transcribed in the proliferating basal layer. Transcription of keratin genes K1 and K10 is induced as cells migrate into the spinous layer. (Lersch, et al., Mol. and Cell Biol., Vol. 8, pp. 486–493 (1988); Knapp, et al., J. Biol. Chem., Vol. 262, pp. 938–945 (1987); Roop, et al., Cancer Res., Vol. 48, pp. 3245–3252 (1988)). K6 is expressed in human skin under conditions of high proliferation and malignant transformation. (Tyner, et al., J. Cell Biol., Vol. 103, pp. 1945–1955 (1986)).

Genes encoding rat and mouse filaggrin have also been identified. In situ hybridization experiments confirmed that transcription of this gene is restricted to the granular layer. (Haydock, et al., J. Biol. Chem., Vol. 261, pp. 12520–12525 (1986); Rothnagel, et al., J. Biol. Chem., Vol. 262, pp. 15643–15648 (1987); Fisher, et al., J. Invest. Dermatol., Vol. 88, pp. 661–664 (1987)).

Loricrin, one of the genes encoding a component of a cornified envelope, has been studied at the molecular level by in situ hybridization showing that transcripts of this gene are restricted to the granular layer. (Mehrel, et al., Cell, Vol. 61, pp. 1103–1112 (1990)). Both the human loricrin gene (Yoneda, et al., J. Biol. Chem., Vol. 267, no. 25, pp. 18060–18066 (1992)), and the mouse loricrin cDNA (Mehrel, et al., Cell, Vol. 61, pp. 1103–1112 (1990)) have been isolated and cloned.

Studies have shown that cells generated by cultivation of a small biopsy can be prepared as stratified sheets and then used for replacement of damaged skin by grafting techniques. (Lindahl, et al., Growth Factors in Health and Disease, p. 388 (1990)). Other studies describe genetically engineered keratinocytes which synthesize human growth hormone. (Morgan, et al., Science, Vol. 237, pp. 1476–1479 (1987)). These studies described retrovirus mediated gene transfer to introduce recombinant human growth hormone into cultured human keratinocytes. The retroviruses were generated from the Ψ AM cell line using an SV40 promoter. (Morgan, et al., Science, Vol. 237, pp. 1476–1479 (1987); Teumer, et al., Growth Hormone and Athymic Mice, FASEB, Vol. 4, pp. 3245–3250 (1990)). The transduced keratinocyte cultures secreted human growth hormone.

In addition, other studies have shown human keratinocytes permanently transformed with plasmids containing the human growth hormone gene under the control of either the metallothionein promoter or the herpesvirus thymidine kiriase promoter. (Lindahl, et al., Growth Factors in Health and Disease, p. 388 (1990)). These studies also described skin grafting techniques with the genetically engineered keratinocytes.

SUMMARY OF THE INVENTION

Applicant has determined that it is useful to construct vectors based upon the control sequences of the epidermal-specific gene termed K1. Specifically, expression of such keratin K1 vectors is tissue and differentiation-specific. Keratin K1 vectors can be used to treat diseases by targeting the vector accordingly. These vectors can also be used to create transgenic animals for assessing human disease in an animal model.

The keratin K1 gene is expressed in the epidermis in a differentiation-specific manner. The regulatory elements of such a keratin gene is useful for tissue and differentiation-specific target vectors. Keratin K1 is associated with early differentiation. Occasionally K1 can be observed in the occasional basal cell that has already ceased mitotic activity and is about to migrate into the spinous layer. By using the regulatory elements of this gene, specific expression vectors can be constructed to target the expression of particular nucleic acids in a tissue and differentiation-specific manner.

The 5' regulatory regions of four human epidermal keratin genes, K5, K6, K10 and K14, have been cloned into vectors to drive expression of the CAT reporter gene. These constructs were transfected into epithelial cells along with vectors expressing nuclear receptors for retinoic acid and thyroid hormone. (Tomic, et al., Cell Reg., Vol. 1, pp. 965–973 (1990)). This study demonstrated that these receptors can suppress the promoters of keratin genes. Suppression was ligand dependent and was evident in primary cultures of epithelial cells. Other studies have discussed the regulation by calcium of human keratin genes K1 and K10. (Rosenthal, et al., Cell Growth and Differentiation, Vol. 2, pp. 107–113 (1991)). 5' and 3' flanking sequence for the human K1 gene responded to elevated levels of calcium in order to induce both mouse K1 and human K1 expression.

Furthermore, both the 5' and 3' sequences for human K1 keratin gene have been used to express oncogenes exclusively to the epidermis of transgenic mice. (Greenhalgh, et al., Mol. Carcinogenesis, Vol. 7, pp. 99–110 (1993); Greenhalgh, et al., Oncogene, Vol. 8, pp. 2145–2157 (1993)). The control elements of 5' and 3' flanking sequences of the human keratin K1 gene that respond to calcium and differentiation were studied by mutations to the 5' and 3' sequences. These studies further define DNA regulatory elements for calcium induced differentiation responses. (Huff, et al., J. Biol. Chem., Vol. 268, No. 1, pp. 377–384 (1993)).

Other expression vectors have been constructed with the K1 5' and 3' sequences to target TGF-β to the epidermis. This study involved the role of TGF-β as an inhibitor of epithelial-cell proliferation. (Sellheyer, et al., PNAS, Vol. 90, pp. 5237–5241 (1993)). In addition, a bovine K6 vector was also constructed to study the role of TGF-β in hair follicles. (Blessing, et al., Genes & Dev., Vol. 7, pp. 204–215 (1993)).

Taking advantage of the unique targeting ability of epidermal cells, the present invention features use of the keratin K1 gene regulatory regions to construct vectors which direct efficient expression of exogenous DNA in epidermal cells. In particular, the present invention demonstrates that by removing sequences that normally restrict expression of the keratin K1 gene in early differentiated cells, an expression vector can be constructed which achieves high levels of expression in undifferentiated epidermal cells. Such expression is greater than equivalent vectors which use the viral promoter SV40. The vector can be constituitively expressed in epidermal cells at all differentiation states, not just the spinous layer. Likewise, if the sequences that normally restrict expression of the K1 gene are not removed, an expression vector may be constructed which directs expression of exogenous DNA to only cells of the earlier differentiated layers of the epidermis.

This unique targeting ability also allows transgenic animal models used for not only the dissection of molecular carcinogenesis and disease, but also in assessing potential chemical and physical carcinogens and tumor promoters, and exploring novel therapeutic avenues. Furthermore, advantages due to the unique targeting ability of the above vector allow methods to administer and treat wounds, surgical incisions, skin ulcers, psoriasis and cancer. Furthermore, the above vectors can be used to transform epidermal cells to produce particular proteins, polypeptides, and RNA, as well as be used in methods for creating immune responses.

Likewise, the above expression vector can be used in vitro with epidermal cells in culture. Use of this vector in vitro allows the role of various nucleic acids to be studied by target specific expression into epidermal cells. (Greenhalgh, et al., Mol. Carcinogenesis, Vol. 7, pp. 99–110 (1993); Greenhalgh, et al., Oncogene, Vol. 8, pp. 2145–2157 (1993)).

It should also be noted that this invention features vectors using the regulatory elements required for specific nucleic acid expression in epidermal cells, including regulatory elements from the K1 gene, as well as other regulatory elements of specific genes which are not K1.

In the first aspect, the present invention features a keratin K1 vector for expression of a nucleic acid sequence in an epidermal cell. The vector includes a 5' flanking region which includes necessary sequences for expression of a nucleic acid cassette, a keratin K1 3' flanking region which regulates expression of a nucleic acid sequence, predominantly in the epidermis, and a linker which connects the 5' flanking region to a nucleic acid. The linker has a position for inserting a nucleic acid cassette. The linker does not contain the coding sequence of a gene that the linker is naturally associated with. That is, the linker is not the normal gene associated with the 5' and 3' regions.

The term "vector" as used herein refers to a nucleic acid, e.g., DNA derived from a plasmid, cosmid, phasmid or bacteriophage, into which fragments of nucleic acid may be inserted or cloned. The vector can contain one or more unique restriction sites for this purpose, and may be capable of autonomous replication in a defined host or organism such that the cloned sequence is reproduced. The vector molecule can confer some well-defined phenotype on the host organism which is either selectable or readily detected. Some components of a vector may be a DNA molecule incorporating DNA, a sequence encoding a therapeutic or desired product, and regulatory elements for transcription, translation, RNA stability and replication. A viral vector in this sense is one that contains a portion of a viral genome, e.g. a packaging signal, and is not merely DNA or a located gene within a viral particle.

The purpose of the vector is for expression of a nucleic acid sequence in an epidermal cell. Expression includes the efficient transcription of an inserted gene or nucleic acid sequence within the vector. Expression products may be proteins, polypeptides or RNA. The gene insert or nucleic acid sequence is contained in the nucleic acid cassette.

The term "nucleic acid cassette" as used herein refers to the genetic material of interest which can express a protein, polypeptide or RNA. The nucleic acid cassette is positionally and sequentially oriented within the vector such that the nucleic acid in the cassette can be transcribed into RNA, and when necessary, translated into a protein or a polypeptide in the transformed epidermal cell. Preferably, the cassette has its 3' and 5' ends adapted for ready insertion into a vector, e.g., it has restriction endonuclease sites at each end.

A variety of proteins and polypeptides can be encoded by the sequence in a nucleic acid cassette in the transformed epidermal cells. Those proteins or polypeptides which can be expressed include hormones, growth factors, enzymes, clotting factors, apolipoproteins, receptors, drugs, oncogenes, tumor antigens, tumor suppressor, viral antigens, parasitic antigens and bacterial antigens. Specific examples of these compounds include proinsulin, insulin, growth hormone, androgen receptors, insulin-like growth factor I, insulin-like growth factor II, insulin growth factor binding protein, epidermal growth factor TGF-α, TGF-β, dermal growth factor (PDGF), angiogenesis factors (acidic fibroblast growth factor, basic fibroblast growth factor and angiogenin), matrix proteins (Type IV collagen, Type VII collagen, laminin), oncogenes (ras, fos, myc, erb, src, sis, jun), E6 or E7 transforming sequence, p53 protein, cytokine receptor, IL-1, IL-6, IL-8, viral capsid protein and proteins from viral, bacterial and parasitic organisms which can be used to induce immune responses. In addition, the nucleic acid cassette can code for antisense RNA or ribosomes as well. These are only examples and are not meant to be limiting in any manner.

In addition, the nucleic acid cassette can encode a "transforming gene" which encompasses viral oncogenes, endogenous proto-oncogenes and activated proto-oncogenes. A variety of oncogenes are known in the art. The term "oncogene" means those genes which cause cancer and include both viral and cellular oncogenes, many of which are homologous to DNA sequences endogenous to rodents and/or humans. The term "oncogene" includes both the viral sequence and the homologous endogenous sequences. Some examples of transforming genes are Ha-ras, K1-ras, N-ras, fos, myc, src, sis, erbA, erbB, jun, p Large T, p Middle T, HPV E7, HPV E6, HPV E5, tat, EIA, Rb, p53, WT1, TGF-α, TGF-β, EGFR, RAR, VD$_3$R, and PKC.

The term "flanking region" as used herein refers to nucleotide sequences on either side of an associated gene. Flanking regions can be either 3' or 5' to a particular gene in question. In general, flanking sequences contain elements necessary for regulation of expression of a particular gene. This can include regulatory sequences necessary for tissue-specific expression, differentiation-specific expression, as well as sequences necessary for efficient expression.

Usually, specific regulatory sequences or elements are embedded adjacent to or within the protein coding regions of DNA. These elements, located adjacent to the gene, are termed cis-acting elements. The signals are recognized by other diffusible biomolecules in trans to potentiate the transcriptional activity. These biomolecules are termed "trans-acting factors". The presence of the trans-acting factors and cis-acting elements have been shown to contribute to the timing and developmental expression pattern of a gene. Cis-acting elements are usually thought of as those that regulate transcription and are found within promoter regions and other upstream (5') or downstream (3') DNA flanking regions.

Flanking DNA with regulatory elements that regulate expression of the genes of the epidermis may also include modulator sequences that are regulated by specific factors, such as Vitamin D and its metabolites, Vitamin A and its metabolites, retinoic acid, and calcium, as well as others. "Modulator Sequences" as used herein refers to sequences which may be in the 3' or 5' flanking regions where such sequences can enhance activation and/or suppression of the transcription of the associated gene. "Responsive" or "respond" as used herein in relation to modulate relates to the enhancement of activation and/or suppression of gene transcription as discussed below. "Metabolites" as used herein refers to any product of metabolism.

The 5' flanking regions may include a promoter, a TATA box, a CAP site and a first intron and intron/exon boundary which are in an appropriate relationship sequentially and positionally for the expression of an associated gene. In this invention, necessary sequences are those elements of the 5' flanking region which are sequentially and positionally in an appropriate relationship to cause the specific expression of a nucleic acid cassette. The 5' flanking region can provide tissue-specific expression to an associated gene.

The 5' sequence may contain elements which regulate tissue-specific expression. The 5' flanking region is located 5' to the associated gene or nucleic acid sequence to be expressed. The 5' flanking region regulatory elements can include the portion of a naturally occurring 5' element responsible for tissue-specific expression. The 5' flanking region can be defined by known procedures. For example, the active portion of the 5' flanking region can be mapped by mutational analysis or various clones created to define the desired activity in a selected vector.

The term "promoter" as used herein refers to a recognition site of a DNA strand to which the RNA polymerase binds. The promoter usually is a DNA fragment of about 100 to 200 base pairs (in eucaryotic genes) in the 5' flanking DNA upstream of the CAP site or the transcriptional initiation start site. The promoter forms an initiation complex with RNA polymerase to initiate and drive transcriptional activity. The complex can be modified by activating sequences termed "enhancers" or inhibitory sequences termed "silencers". The promoter can be one which is naturally or non-naturally associated with a 5' flanking region.

The term "intron" as used herein refers to a section of DNA occurring in a portion of a gene which does not code for an amino acid in the gene product. RNA transcribed from such an intron is included in a precursor RNA, from which the intron mRNA is then excised (and is therefore not transcribed into messenger RNA nor translated into protein).

The term "exon" as used herein refers to a portion of a gene that is included in the transcript of a gene and survives processing of the RNA in the cell to become part of a messenger RNA. Exons generally occupy three distinct regions of genes that encode proteins. The first, which is not translated into proteins, signals the beginning of RNA transcription and contains sequences that direct the messenger RNA to the ribosomes for protein synthesis. The exons in the second region contain the information that is translated into the amino acid sequence of the protein. Exons in the third region are transcribed into the part of the messenger RNA that contains the signals for termination of translation and for the addition of polyadenylation tail (poly(A)).

The intron/exon boundary will be that portion in a particular gene where an intron section connects to an exon position. The terms "TATA box" and "CAP site" are used as they are recognized in the art.

The 3' flanking region contains sequences which regulate expression predominantly in the epidermal cells of a nucleic acid sequence. The 3' flanking regions provide tissue-specific expression to an associated gene. The 3' flanking region may be located within a vector of this invention either 5' or 3' to that of an associated gene in order to regulate its expression. The term as used herein includes that portion of the naturally occurring 3' flanking region responsible for tissue-specific expression. That portion can be readily defined by known procedures. For example, the active portions of a 3' flanking region can be mapped by mutational analysis or various clones created to define the desired activity in a selected vector system.

The 3' flanking region may also contain a 3' untranslated region or 3' UTR. This term refers to the sequence at the 3' end of a structural gene which is usually transcribed with the gene. This 3' UTR region usually contains a poly(A) sequence. Although the 3' UTR is transcribed from the DNA, it is not translated into protein. Keratin-specific 3' UTR sequences may be used to allow for specific stability in a keratinocyte or epidermal tissues.

A "3' non-coding region" or "3' NCR" is a region contiguous to the 3' UTR region of a structural gene. The 3' NCR region generally contains a transcriptional termination signal.

The 3' UTR and 3' NCR sequences provide a higher level of messenger RNA accumulation through increased messenger RNA stability in keratinocytes rather than non-keratinocyte cells. Thus, this increased stability of messenger RNA leads to increased levels of protein production. It should also be noted that the 5' flanking region can also contain UTR sequences.

The 3' flanking regions from a keratin K1 gene regulates expression predominantly in the epidermis. "Predominantly" as used herein means that the gene associated with the 3' flanking region, whether natural or in the expression vector, will be expressed to a higher degree only in the epidermis, i.e., to the same order of magnitude of difference as would be found in natural expression of the keratin K1 gene in the epidermis versus other cell types. In addition, the same magnitude of difference may be observed in an epidermis versus other cell types by Northern analysis, X-Gal, immunofluorescence or CAT assays as discussed herein and known in the art. While keratin genes are normally expressed in the epidermis or epidermal cells, namely, keratinocytes, keratin genes are expressed to a lower degree in other tissues, such as the oral mucosa, esophagus and trachea, and other tissues as well. The 3' flanking region as used herein will also express the associated gene in other tissues but to a lower degree than expression in the epidermis. Expression is preferentially in the epidermis.

By "keratin K1 gene" is meant those genes exemplified herein and their equivalents in other animal species or other tissues. Homologous or analogous sequences are also included so long as they provide equivalent regulatory properties to those described herein. It is important in this invention that the chosen sequence provide the tissue specific expression noted herein. In addition, other sequences such as the modulators and regulators noted herein include such analogous sequences and functionalities. Those in the art will recognize that the minimum sequences required for such a function are encompassed by such a definition and are readily determined by standard technique exemplified herein.

In addition to the above, the 3' flanking region may also contain approximately 8.0 kb of a 5' flanking sequence (or the functional sequence therein) from the 18 kb EcoRV fragment. An 18 kb EcoRV fragment is from the human keratin K1 gene and is expressed exactly like the endogenous mouse K1 gene, i.e., post mitotically in cells committed to terminal differentiation. This may be inserted at the end of the vectors at the 3' flanking region. Expression of this vector will only be in cells after they commit to terminal differentiation.

The term "linker" as used herein refers to DNA which contains the recognition site for a specific restriction endonuclease. Linkers may be connected to the ends of DNA fragments prepared by cleavage with some other enzyme. A linker having a unique restriction endonuclease site at the location of the start and stop codon connects the 5' flanking region to a nucleic acid. In particular, the linker provides a position for inserting the nucleic acid cassette which contains a specific nucleic acid sequence to be expressed. This position may be an endonuclease site in the linker, such as Cla I, Not I, Xma I, Bgl II, Pac I, Xho I, Nhe I and Sfi I.

In preferred embodiments, the vector described above may have both its 5' flanking region and its 3' flanking region from keratin K1 gene. In particular, the present invention may have a 5' flanking region of approximately 1.2 kb, and a 3' flanking sequence of approximately 2.1 kb of a keratin K1 gene.

As discussed above, these regions can be further and more precisely defined by routine methodology. Preferably, the vector contains such a 3' region or 5' region comprising, consisting, or consisting essentially of these regions. The term "consisting of" is used herein as it is recognized in the art. A vector with the 3' or 5' regions "consisting essentially of" the regions of the present invention includes those regions in which the sequence is changed, but the desired vector activity remains equivalent. Such a change, for example, could be a change of 10 nucleotides in any of the above regions. This is only an example and is non-limiting.

More particularly, the vector above, may contain a 5' flanking region having nucleotides 1 to 46 of Sequence ID No. 1, a 3' flanking region having nucleotides 6891 to 10747 of Sequence ID No. 1, and a linker having nucleotides 2351 to 2376 of Sequence ID No. 2.

The invention can also feature a vector as described above with 5' UTR sequences, 3' UTR sequences, and 3' NCR sequences. These can be incorporated into the vector to allow the nucleic acid in the cassette to be transcribed into RNA and then when necessary, translated into proteins or polypeptides in the transformed epidermal cell.

A second aspect of the present invention is a purified nucleic acid sequence comprising the keratin. K1 gene 5' flanking region and the 3' flanking region of Sequence ID No. 1. "Purified" as used herein means that the sequence is isolated from its natural state. The present invention also covers the 5' flanking region or the 3' flanking region by themselves. Not only does the invention cover either of the 5' flanking region and/or 3' flanking region of the isolated keratin K1 gene, but other equivalent keratin K1 genes as well.

In a third related aspect, the present invention features an epidermal cell transformed with a vector as described above for expression of a nucleic acid sequence. As described above, the nucleic acid cassette may contain genetic material encoding for a variety of proteins, polypeptides or RNA.

As used herein, transformation is a mechanism of gene transfer which involves the uptake of DNA by a cell or organism. Following entry into the cell, the transforming DNA may recombine with that of the host or may replicate independently as a plasmid or temperate phage. Cells which are able to take up DNA are described as competent. Particular cells may not be naturally competent, but require various treatments in order to induce the transfer of DNA across the cell membrane.

Transformation can be performed by in vivo techniques as described below, or by ex vivo techniques in which epidermal cells are co-transfected with a vector containing a selectable marker. This selectable marker is used to select those cells which have become transformed. It is well known to those skilled in the art the type of selectable markers to be used with transformation studies.

The transformed cell can produce a variety of compounds selected from proteins, polypeptides or RNA, including hormones, growth factors, enzymes, clotting factors, apolipoproteins, receptors, drugs, tumor antigens, viral antigens, parasitic antigens and bacterial antigens. Other examples can be found above in the discussion of nucleic acid cassette. The product expressed by the transformed cell depends on the nucleic acid of the nucleic acid cassette. As discussed above, this list is only an example and is not meant to be limiting.

A fourth aspect of the present invention features methods for transformation of epidermal cells. These methods comprise the steps of contacting a cell with a vector as described above for a sufficient time to transform the epidermal cell.

In a fifth aspect, the present invention features a method for treating a wound or surgical incision. In addition, the present invention features a method to treat skin ulcers. These methods use the above-referenced vectors in order to transform epidermal cells. The nucleic acid cassette of the vector contains genetic material coding for a growth factor, a matrix protein or angiogenesis factor. Expression of such genes in vivo aids in the treatment of wounds or surgical incisions. As above, the methods of transformation can be by in vivo or ex vivo techniques.

In a more particular related aspect, the methods involve transforming epidermal cells with a plurality of the above-referenced vectors. In these particular methods, the genetic material of at least one vector codes for a growth factor, the genetic material of at least one vector codes for a second growth factor, the genetic material of at least one vector codes for a matrix protein and the genetic material of at least one vector codes for an angiogenesis factor. The growth factors may consist of epidermal growth factor, transforming growth factor, dermal growth factor or even growth hormone. The matrix protein may consist of Type IV collagen, laminin, nidogen or Type VII collagen. The angiogenesis factor may consist of acidic fibroblast growth factor, basic fibroblast growth factor and angiogenin.

Transformation in these methods and those below can be performed by in vivo techniques, as well as ex vivo techniques. Ex vivo techniques also can include transplanting the transformed epidermal cells into the animal or human to be treated. Such an ex vivo procedure is used with treating wounds or surgical incisions or skin ulcers and other methods below.

A sixth related aspect of the present invention features a method for treating psoriasis by transforming epidermal cells with the above-referenced vectors. These vectors contain nucleic acid sequences coding for proteins, polypeptides or RNA, such as transforming growth factors or cytokine receptors. The RNA which is produced by the expression vector may be antisense RNA complementary to transforming growth factor alpha, IL-1, IL-6 or IL-8. The cytokine receptors may be receptors for IL-1, IL-6 or IL-8. "Receptor" as used herein includes natural receptors as well as anything that binds a ligand and causes compartmentalization changes in a cell.

A seventh related aspect of the present invention features a method for treating cancer. This method includes the transformation of squamous epithelial cells with the above-referenced vectors. The nucleic acid cassettes of the above vectors contain genetic material coding for proteins, polypeptides or RNA. In particular, the genetic material may code for the p53 protein or code for antisense RNA which is complementary to the E6 or E7 gene of human papilloma virus.

Squamous epithelial cells as used herein, are cells which may be either epidermis cells, oral mucosa, esophageal, vaginal, trachea or corneal epithelia.

An eighth related aspect of the present invention features a method for inducing an immune or immunological response by transforming an epidermal cell with the above-referenced vector. The nucleic acid cassette may contain nucleic acid sequences coding for proteins or polypeptides, or other factors which might produce an immunogenic or immunological response. The nucleic acid cassette can contain genetic material that encodes for microbial proteins. This includes genetic material coding for a viral capsid protein from the human papilloma virus, other viral capsids, bacterial proteins and toxins. This is only an example and is not meant to be limiting.

A ninth related aspect of the invention features a transgenic animal whose cells contain the vector referenced above. These cells include germ or somatic cells. Transgenic animal models can be used for not only dissection of molecular carcinogenesis and disease, but also in assessing potential chemical and physical carcinogens and tumor promoters, and exploring therapeutic avenues.

The genetic material which is incorporated into the epidermal cells from the above vectors includes DNA not normally found in epidermal cells, DNA which is normally found in epidermal cells but not expressed at physiological significant levels, DNA normally found in epidermal cells and normally expressed at physiological desired levels, and other DNA which can be modified for expression in epidermal cells, and any combination of the above.

The vectors of the above methods may be administered by various routes. The term administrations refers to the route of introduction of a vector or carrier of DNA into the body. Administration may be intravenous, intramuscular, topical, oral, or by gene gun or hypospray instrumentation. Administration can be directly to a target tissue or through systemic delivery. Administration will include a variety of methods, such as direct gene transfer into skin tissue by liposomes, proteoliposomes, calcium phosphate-coprecipitated DNA, DNA coupled to macromolecular complexes, DNA transporters, DNA coded to microprojectiles, coded plasmids, direct microinjection, as well as skin grafts. Direct gene transfer of vectors can be administered by direct microinjection, electroporation, liposomes, proteoliposomes, calcium phosphate-coprecipitation, skin grafts, retroviral vectors, DNA coupled to macromolecular complexes, DNA transporters and microprojectiles. Routes of administration include intramuscular, aerosol, oral, topical, systemic, ocular, intraperitoneal and/or intrathecal. See, e.g., WO 93/18759, hereby incorporated by reference herein.

Other features and advantages of the invention will be apparent from the following detailed description of the invention in conjunction with the accompanying drawings and from the claims.

BRIEF DESCRIPTION OF THE DRAWINGS

FIG. 1 is a schematic drawing of the human keratin K1 gene (HK1) and the expression vector derived from its regulatory sequences.

FIG. 2 demonstrates the suppression of the SV40 promoter by a novel negative regulatory element from the HK1 gene (HK1.NRE) in the presence of Vitamin $D_3$.

FIG. 3 is a schematic drawing of the HK1 vector containing the coding sequence of v-ras$^{Ha}$ protein of Harvey Murine Sarcoma Virus.

FIG. 4 is a schematic drawing of the HK1 vector containing the coding sequence of the v-fos protein from a FBJ/FBR chimeric plasmid.

FIG. 5 is a schematic drawing of the HK1 expression vector containing the coding sequences of the E6 and E7 proteins from human papilloma virus 18.

FIG. 6 is a schematic drawing of the HK1 vector containing the coding sequence of TGF-α.

FIG. 7 is a schematic drawing of the HK1 vector containing the coding sequence of the trans-regulatory protein tat, from human immunodeficiency virus.

FIG. 8 is a schematic drawing of an 18 kb EcoRV fragment containing the HK1 gene.

FIG. 9 is a schematic drawing of a derivative of the HK1 vector containing additional 5' flanking sequences which restrict expression to differentiated epidermal cells.

FIG. 10 illustrates the nucleotide sequence of the protected regions FP(A) and FP(BP). The consensus AP-1 site within FP(A) is underlined. The canonical hormone response elements within FP(B) are denoted by arrows.

The drawings are not necessarily to scale, and certain features of the invention may be exaggerated in scale and shown in schematic form in the interest of clarity and conciseness.

DETAILED DESCRIPTION OF THE INVENTION

It will be readily apparent to one skilled in the art that varying substitutions and modifications may be made to the invention disclosed herein without departing from the scope and spirit of the invention.

The following examples are offered by way of illustration and are not intended to limit the invention in any manner.

The following are specific examples of preferred embodiments of the present invention. These examples demonstrate how keratin K1 based vectors can be used in construction of various cellular or animal models, and how genes can be regulated by sequences within such vectors. The utility of such vectors is noted herein and is amplified upon in co-pending application by Roop et al., entitled "Specific Expression Vectors and Methods of Use", supra, and such sections are hereby specifically incorporated by reference herein.

Below are provided examples of specific regions of the keratin K1 genes that can be used to provide certain functionalities to an expression vector, and thus within a transformed cell or animal containing such a vector. Those in the art will recognize that specific portions of these regions can be identified as that containing the functional nucleic acid sequence providing the desirable property, and such regions can be readily minimized using routine deletion or mutagenic techniques or their equivalent. Thus, such regions include the modulator sequence described below, as well as those sequences responsive to calcium, Vitamin D and its metabolite, Vitamin A and its metabolite, and progesterone. As noted herein, such controlling segments of nucleic acid may be inserted at any location on the vector, although there may be preferable sites as described herein.

EXAMPLE 1

Construction and Characterization of a Vector

To target the expression of exogenous DNA to the epidermis a vector from the human keratin K1 gene was constructed. Among its many uses, it is useful in making transgenic animals.

A schematic showing the structure of the human keratin K1 gene is shown in FIG. 1. The 10.8 kb EcoRI fragment containing the entire human keratin K1 gene was originally isolated from lambda clone c55 (Johnson, et al., PNAS, USA, Vol. 82, pp. 1896–1900 (1985)). In constructing the targeting vector, most of the first exon including the ATG was removed, leaving only the 5' non-coding sequences, the first intron and the intron/exon boundaries. In addition, the remainder of the gene up to the termination codon was deleted. A polylinker containing the following unique restriction sites (Bam HI, Xma I, Kpn I, Not I, and Cla I) was engineered into a site 3' of the first intron to allow easy insertion of exogenous DNA. These manipulations were performed through the use of polymerase chain reactions (PCR). The unique EcoRI sites were conserved at the ends of the vector to allow easy amplification in pGEM vectors and excision for purification from plasmid sequences prior to injection into embryos.

The rationale for constructing the vector in this manner was as follows. Since the specific elements responsible for the expression characteristics of the 10.8 kb human keratin K1 fragment are not defined, the entire 5' and 3' flanking regions were included in the vector construct. One skilled in the art will readily recognize that as these elements are further defined the flanking sequences can be changed accordingly. For example, the vector may contain a nucleic acid sequence consisting of the 10.8 kb EcoRI fragment and an additional 8.1 kb of sequence 5' to the 10.8 kb EcoRI fragment, comprising an approximately 18 kb EcoRV nucleic acid sequence. In addition, sequences within the 3' non-coding region were retained since these may confirm stability to transcripts of exogenous DNA in epidermal cells. Further description of 3' regulatory elements are set forth in Example 16. The first intron was retained to potentially enhance expression efficiency (Brinster, et al., PNAS, USA, Vol. 82, pp. 1896–1900 (1988).

EXAMPLE 2

HK1 Expression in Epidermal Keratinocytes

To assess the human keratin K1 targeting vector for exclusive expression in epidermal keratinocytes, the β-galactosidase reporter gene was cloned into Bam HI and Cla I restriction sites located in the polylinker region of the expression vector (FIG. 1). The β-galactosidase gene has frequently been used as a reporter gene to assess targeting specificity (MacGregor, et al., In: Methods in Molecular Biology, Vol. 7, pp. 217–235 (1991). This construct was designated pHK1.β-gal. To determine if expression of this construct resulted in the production of a functional protein, and to determine whether the vector retained cell type specificity, this construct was transfected into primary epidermal keratinocytes and primary dermal fibroblasts. At seventy-two hours post transfection cells were stained with a solution containing the substrate 5-bromo-4-chloro-3-indoyl-β-galactosidase (X-gal). β-galactosidase activity, indicated by a blue coloration, was detected in keratinocytes but not fibroblasts. Thus, expression of the HK1.β-gal construct was cell type specific and resulted in the production of a functional protein.

EXAMPLE 3

Transgene Mice

The same pHK1.β-gal construct utilized in the in vitro studies discussed in Example 2 was used in the production of transgenic mice. This construct was digested with EcoRI (see FIG. 1) and subjected to preparative agarose gel electrophoresis to purify the pHK1.β-gal expression construct away from plasmid sequences (pGEM 3) which might interfere with expression. The separated expression construct sequences were purified and recovered using NA 45 DEAE membrane (Schleicher & Schuell). DNA was precipitated and resuspended at 1–3 ng/μl. ICR outbred female mice (Sasco) were given PMS and HCG to stimulate superovulation, mated to FVB males (Taconic) and the resulting early fertilized embryos (most preferably on cell stage) were collected from the oviducts. DNA was microinjected into the pronuclei and the embryos were surgically transferred to pseudopregnant recipient females (the result of mating ICR females with vasectomized $B_6D_2F_1$ males (Taconic)).

In the initial experiments, 40 mice were born. In order to quickly determine if the pHK1.β-gal transgene was being exclusively expressed in the epidermis of these mice, these animals were sacrificed at birth. A small amount of tissue was removed for extraction of DNA and the remainder of the neonate was rapidly frozen in Tissue-Tek O.C.T. for frozen sections. PCR analysis was performed on the extracted DNA using oligonucleotide primers specific for the intron within the HK1 vector and this demonstrated that five of the 40 neonates contained the HK1.β-gal construct.

To assess whether expression of the HK1β-gal construct was restricted to the epidermis or expressed in other squamous epithelia, frozen longitudinal sections were cut from several PCR positive and PCR negative embedded neonates and these were stained with X-Gal. Data showed where a PCR positive animal, #30, expressed high levels of β-galactosidase in the epidermis and a PCR negative sibling, #29, was completely negative, indicating that endogenous murine β-galactosidase was not expressed at sufficient levels in the epidermis to cause false positives in this assay. Staining of the intestine was observed in both the positive (#30) and negative (#29) neonates. This may represent endogenous enzyme activity or the production of β-galactosidase by bacteria in the intestine. X-gal staining was detected in the basal compartment, although it is not as intense as in the differentiated layers. Thus, the human keratin K1 expression vector is also expressed in a substantial number of proliferating basal cells.

The most important finding from these initial transgenic experiments is that the vector constructed from the human keratin K1 gene can target the expression of an exogenous coding sequence exclusively to the epidermis of transgenic mice. This specificity of targeting was readily shown by the data. A low power exposure of the skin of #30 demonstrates intense staining with X-Gal. In addition, there are numerous hair follicles and sebaceous glands which do not stain with X-Gal. Keratins K5 and K14 are not only expressed in the epidermis, but in all squamous epithelia, including hair follicles and sebaceous glands. The expression pattern for keratin K14 is revealed by immunofluorescence with a specific K14 antiserum. Staining of the epidermis, as well as hair follicles and sebaceous glands is observed. If the strategy used in construction the human keratin K1 expression vector had altered its targeting specificity in transgenic mice, then X-Gal staining would have been observed in hair follicles, sebaceous glands, other squamous epithelia, and perhaps even other tissue types. However, expression of the HK1.β-gal transgene, like the keratin K1 gene itself is restricted to the epidermis.

EXAMPLE 4

Regulation of Keratin K1 Vector by Vitamin $D_3$

A novel Vitamin $D_3$ responsive element was used to modulate expression levels in the epidermis. Although all of the regulatory elements of the human keratin K1 gene have not been identified, a novel negative regulatory element from the human keratin K1 gene (HK1.NRE) has been identified and this example demonstrates that it is able to suppress a heterologous promoter in response to Vitamin $D_3$. The HK1.NRE is 70 nucleotides in length (nucleotides 9134 to 9204 of Sequence ID No. 1). PCR technology was used to generate Bam HI and Bgl II sites at opposite ends of this fragment. This facilitates generating multiple copies of this fragment since ligation and digestion with Bam HI and Bgl II will select for oligomers which have ligated head to tail. Four tandem copies of the HK1.NRE were inserted into the Bgl II cloning site of pA10.CAT. In the absence of Vitamin $D_3$ this construct is highly expressed when transfected into primary mouse epidermal cells (FIG. 2). The addition of increasing concentrations of Vitamin $D_3$ to the culture medium completely suppresses transcription of this heterologous promoter. This observation indicates that the activity of the human keratin K1 expression vector can be modulated in the epidermis. The activity of the human keratin K1 vector is suppressed in the epidermis by topical application of Vitamin $D_3$, or an analogue, to the skin. In addition, it was determined that retinoic acid restored activity of the K1 vector. Further discussion of Vitamin D regulation is set forth in Examples 8 and 16.

EXAMPLE 5

Development of Transgenic Animal Models for Skin Carcinogenesis

The ability to stably introduce genes into the germline of mice has greatly enhanced prospects for generation of animal models of human disease (Leder and Stewart, U.S. Pat. No. 4,736,866 issued Apr. 12, 1988, and Palmiter and Brinster, Ann. Rev. Genet., Vol. 20, pp. 465–499). When such genes are combined with regulatory sequences that target their expression to specific tissues, it provides a model to not only study diseases in the context of living organisms, but also in specific tissues suspected of being the targets of these genes. Thus, transgenic mice offer the possibility to determine the influence of factors such as blood supply, an intact immune system, humoral and cell-mediated growth controls and physical barriers on disease progression. The epidermis is an attractive tissue for targeted gene expression; not only is it a model for epithelial diseases in general but the accessibility of the epidermis allows easy detection of progressive pathological changes that result from transgene expression as well as the assessment of the potential role played by environmental factors in these processes. In addition, the prospects for utilizing gene therapy to treat cancer are coming closer to reality. Therefore, animal models of human cancers would be useful to assess the therapeutic potential of these approaches. The development of animal models of skin disease is dependent upon the ability to specifically target gene expression to the epidermis. The human keratin K1 targeting vector described in Example 1 is ideally suited for this purpose.

EXAMPLE 6

Targeting the v-ras$^{Ha}$ Oncogene to the Epidermis

One family of proto-oncogenes, the ras family (ras$^{Ha}$, ras$^{K1}$, ras$^{N}$), has been identified in approximately 20% of human tumors by virtue of specific point mutations at codons 12, 13, and 61 which activate their transforming potential. The mechanisms whereby ras genes become activated are currently unknown but there is widespread evidence that environmental agents play pivotal roles in the etiology of ras mutations. To date, few studies have undertaken to study ras activation in human skin malignancies. However recent reports have identified ras$^{Ha}$ activation in basal and squamous cell carcinomas appearing on sun exposed body sites, interestingly at potential pyrimidine dimer sites possibly derived from skin exposure to UV irradiation. In the mouse skin model of chemical carcinogenesis where the three distinct stages of initiation, promotion and malignant conversion have been defined, ras$^{Ha}$ activation has been found in benign squamous papillomas, the end point of initiation and promotion suggesting an early role for ras$^{Ha}$ in skin carcinogenesis. Taken collectively, the above experimental evidence suggests the importance of developing an animal model to further study the mechanism of ras$^{Ha}$-induced skin carcinogenesis. Toward this end, the sequence encoding the v-ras$^{Ha}$ protein of Harvey Murine Sarcoma Virus (Dhar, et al., Science, Vol. 217, pp. 934–937 (1982) was cloned into the Bam HI and Cla I sites of the human keratin K1 expression vector (FIG. 3). To discriminate expression of the v-ras$^{Ha}$ transgene from that of the endogenous ras gene, a sequence encoding the human keratin K6 epitope Sequence ID No. 4 was engineered onto the 5' end of the v-ras$^{Ha}$ cassette.

HK1 ras transgenic mice exhibit the following phenotype: 1) Newborn transgenic mice expressing v-ras$^{Ha}$ (HK1 ras) exclusively in the epidermis show distinct wrinkled skin at 48 hours and are smaller than litter mates. 2) Juvenile HK1 ras transgenic mice exhibit progressive keratinization which peaks at 14 days. 3) The histotype of newborn HK1 ras mice reveals massive epidermal hyperplasia with up to 20-fold thickening of the epidermis. 4) By day 14 this progresses to massive hyperkeratosis. Both histotypes are pre-neoplastic, papillomatous, non-dysplastic and exhibit few appendages.

The HK1 ras transgenic mice develop benign tumors. Typical lesions appear within 10–12 weeks at single sites. The histotype of these tumors reveals a well differentiated squamous papilloma. Papillomas often appear at sites after wounding. Many of these papillomas are prone to regression. This regression phenomenon suggests that ras$^{Ha}$ alone is insufficient to maintain even a benign phenotype and requires further events which may involve roles for additional oncogenes/antioncogenes. (Greenhalgh, et al., Induction of Epidermal Hyperplasia, Hyperkeratosis and Papillomas in Transgenic Mice by a Targeted v-Ha-ras Oncogene, Mol. Carcinog., Vol. 7, pp. 99–110 (1993)).

EXAMPLE 7

Targeting the fos Oncogene to the Epidermis of Transgenic Mice

Recent in vitro studies have shown that the v-fos gene can convert to malignancy primary keratinocytes or papilloma cell lines which expressed an activated ras$^{Ha}$ (Greenhalgh, et al., PNAS, USA, Vol. 87, pp. 643–647 (1990); Greenhalgh and Yuspa, Mol. Carcinogen., Vol. 1, pp. 134–143 (1988)). This suggested that fos could play a later role in epidermal carcinogenesis and cooperate with the benign phenotype imparted by activated ras-$^{Ha}$ expression. Although this alone was sufficient to initiate the establishment of HK1 fos transgenic mice with a view to mate with HK1 ras mice, two further studies have identified a role for fos in normal epidermal differentiation and thus highlights fos as an attractive target for perturbation. Using a c-fos/β-gal fusion gene Curran and co-workers (Smeyne, et al., Neuron, Vol. 8, pp. 13–23 (1992)) have shown significant fos expression in the differentiated layers of the epidermis and (Fisher, et al., Development, Vol. III, pp. 253–258 (1991)) have localized c-fos expression to a specific subset of granular cells.

Thus, fos may have an important role in the control of the final stages of keratinocyte differentiation. The putative perturbations of this normal role for c-fos in such specialized cells by v-fos can only be explored in the context of targeted expression in transgenic mice. In addition the c-fos proto-oncogene is known to function as a transcriptional regulator in conjunction with the c-jun/AP 1 gene product and thus, while targeting ras$^{Ha}$ represents studies of membrane signalling on neoplasia, targeting fos explores the role of transcriptional control on this process.

Thus, the fos protein coding sequence from the FBJ/FBR chimeric v-fos plasmid pFBRJ was inserted into the human keratin K1 targeting vector (FIG. 4). To discriminate expression of the v-fos transgene from that of the endogenous fos gene, a sequence encoding the human keratin K1 epitope (Sequence ID No. 5) was engineered onto the 5' end of the v-fos cassette.

HK1 fos transgenic mice exhibit the following phenotype: 1) A specific ear phenotype typically appears at 3–4 months initially in the wounded (tagged) ear and then becomes bilateral. 2) In several animals expressing severe phenotypes, the wounded ear lesion can grossly resemble a benign keratoacanthoma. 3) Alopecia and hyperkeratosis of the axilla often develop in older animals (approximately 1 year of age).

The histotypes of the HK1 fos mice are as follows: 1) The histotype of the initial ear lesions exhibits hyperplasia and hyperkeratosis, a pre-neoplastic pathology with few dysplastic cells and little evidence of further neoplastic progression. 2) At later stages the massive hyperkeratotic histotype resembles a benign keratoacanthoma.

Three HK1 fos transgenic mice lines have been established which develop an obvious pre-neoplastic ear phenotype at 3–4 months. The promotion stimulus derived from wounding (i.e., ear tag) appears to accelerate the appearance of this phenotype which eventually becomes bilateral. Also, it appears that friction in the axilla and inguinal area may also promote a pre-neoplastic hyperplastic/hyperkeratotic response after a significant latent period. Collectively these data support a fundamental role for the fos gene in normal keratinocyte differentiation and perturbation by v-fos results in pre-neoplastic differentiation disorders. In several HK1 fos mice severe ear lesions appear to progress to resemble benign keratoacanthomas. Although numbers are low at this time, that this is the resultant tumor type is consistent with a role for fos in the latter stages of terminal differentiation, and low numbers and latency suggest a requirement for additional events. (Greenhalgh, et al., Hyperplasia, Hyperkeratosis and Benign Tumor Production in Transgenic Mice by a Targeted v-fos Oncogene Suggest a Role for fos in Epidermal Differentiation and Neoplasia, Oncogene, Vol. 8, pp. 2145–2157 (1993)).

EXAMPLE 8

Targeting HPV 18 E6 and E7 Gene Expression to the Epidermis

There is widespread evidence from clinical and epidemiological studies which implicate human papilloma viruses (HPV) in the etiology of certain squamous epithelial tumors in humans. HPV's have a specific tropism for squamous epithelial cells and different types of HPVs have specificity for the anatomic site that they infect. Additionally, within a specific subgroup of HPVs, certain types are associated with development of either benign (e.g., HPV6 and 11) or malignant (e.g., HPV-16 and 18) disease and this may center on the properties of the E6 and E7 genes. Through adaptation to the differentiation programs of the epithelia that they infect, HPVs have evolved a clever strategy for the production of infectious progeny. HPVs infect basal epithelial cells but do not undergo lytic replication in this compartment, thus, the germinative pool of cells is not subjected to the cytopathic effects of late viral gene expression. Production of virus only occurs in terminally differentiated cells that have lost proliferative potential and will be desquamated into the environment.

This strategy not only provides for the spread of mature viral particles, but ensures their continuous production by replenishment with cells from the basal compartment. Since the life cycle of the virus is so tightly linked to all stages of differentiation of squamous epithelial cells, establishment of successful culture systems has been difficult. To date, these host factors, coupled with regulatory mechanisms present within papilloma virus genomes themselves have also hindered attempts to observe pathological effects of HPV gene expression in squamous epithelia in transgenic mice. These restrictions on utilization of the transgenic mouse model have been overcome with the ability to specifically target HPV gene expression to squamous epithelia using the human keratin K1 targeting vector.

In the example provided, the sequence encoding the HPV-18 E6 and E7 ORF was inserted at the Bam HI and Cla I sites of the human keratin K1 targeting vector polylinker to create the HK1.E6/E7 transgene, by employing a 5' E6 specific oligo #1 (5'-CCCCGGGATCGATCTGGATC-AGCCATTGTTGC-3') and a 3' E7 specific oligo #2 (5'-CCCGGGAGATCTCACAATACTATGGCGCGC-3'). The E6/E7 ORF was initially obtained by PCR amplification of HPV18 nco plasmid DNA using oligos #1 and #2, and the reaction conditions described previously, Kopan, et al., Retinoids as Important Regulators of Terminal Differentiation: Examining Keratin Expression in Individual Epidermal Cells at Various Stages of Keratinization, J. Cell Biol., Vol. 105, pp. 427–440 (1987); Hosomi, et al., Regulation of Terminal Differentiation of Cultured Mouse Epidermal Cells by 1a, 25-dihydroxyvitamin D3, Endocrinology, Vol. 113, 1950–1957 (1983). The PCR product was digested with Bgl II and ClaI, paper purified, subcloned into the human keratin K1 targeting vector and sequenced employing standard techniques (FIG. 5).

Generation and Identification of Transgenic Mice

The control of HPV gene expression is tightly linked to the program of differentiation in squamous epithelia and is species-restricted. In order to overcome these limitations, and generate an in vivo transgenic mouse model, an epidermal targeting vector was employed, based on HK1, to express the transforming genes E6 and E7 of HPV 18 exclusively in the epidermis.

Plasmid DNAs were prepared by standard techniques (Maniatis, et al., Molecular Cloning, A Laboratory Manual (Cold Spring Harbor, N.Y.: Cold Spring Harbor Laboratory) (1982)). The HK1.E6/E7 transgene was released from the pGem3 plasmid by digestion with EcoRI and the 7 kb fragment isolated by agarose gel electrophoresis and paper purification. The purified HK1.E6/E7 DNA concentration was adjusted to 2 ng/µl in 10 mM Tris HCL, 0.25 mM EDTA pH 7.5 and subjected to 40,000 rpm ultracentrifugation for 1 hour to remove debris prior to microinjection. Mouse embryos were isolated as described previously (Hogan, et al., Manipulating the Mouse Embryo. A Laboratory Manual (Cold Spring Harbour, N.Y.: Cold Spring Harbour Laboratory) (1986)). DNA was microinjected into the pronuclei of one cell mouse embryos, obtained from 10–12 g female ICR mice mated to male FVB mice supplied by Sasco animal facility (Houston, Tex.). After microinjection, 15–20 surviving embryos were transferred to the oviduct of ICR pseudo pregnant foster mothers and normal gestation allowed. Transgenic mice were confirmed by tail DNA isolation (Hogan, et al., Manipulating the Mouse Embryo. A Laboratory Manual (Cold Spring Harbour, N.Y.: Cold Spring Harbour Laboratory) (1986)), and PCR analysis using vector-specific oligos #3 (5'-TGGTCCA-CTTGGGATTGGTG-3') and #4 (5'-GGAGTCT-CATAGCCATGG-3') specific for the first intron of the expression vector.

Preparation and Analysis of RNA

Mouse epidermis, prepared from 1–5 day old neonates as described (Yuspa, et al., Epidermal Cell Culture, Transplantation Proc., Vol. 12, Suppl. 1, pp. 114–122 (1980), together with surgically removed lesions and organs, was routinely stored in liquid nitrogen prior to total RNA isolation employing the RNAzol (Biotex Labs, Houston) protocol. Total RNA was subjected initially to Northern analysis to determine the expression of the HK1.E6/E7 transgene.

Following formaldehyde agarose gel electrophoresis and transfer to nitrocellulose, filters were hybridized to a random-primed sequence specific for the 3' non-coding region of the vector (specific activity $2\times10^8$ cpm), and washed to a final stringency of 0.5× standard sodium citrate/0.1% SDS at 68° C. prior to autoradiography at −70° C. using Kodak X-Omat AR5 film with intensifying screen. Total RNA was also analyzed for HK1.E6/E7 expression by reverse transcriptase PCR (RT/PCR) employing the BRL preamplification system (BRL Bethesda, Md.) and, following manufactures instructions, cDNA was generated using 5 $\mu$g of total RNA and 200 ng of a HK1 3' non-coding specific oligo (oligo #5 (5'-ATCGACCTCGGTCTTGCC-3')). This cDNA was amplified employing oligos #1 and #2 specific for E6 and E7 as described (Greenhalgh, et al., Targeted Expression of v-ras$^{Ha}$ to the Epidermis of Transgenic Mice Induces Hyperplasia, Hyperkeratosis and Papillomas, Mol. Carcinog., Vol. 7, pp. 99–110 (1993)), using the absence of reverse transcriptase to account for DNA contamination, or using oligo #6 (5'-CCCGGCTTCGAATTTGCCTCCTTCATTC-3'), specific for vector sequences 5' to the intron.

This latter reaction allowed for both assessment of contaminating DNA and the cloning, into pGem3 at the ClaI sites, of PCR amplified (oligos #6 and #2), Csp45/ClaI digested cDNA representing the predominant HK1.E6/E7 transcript which was then subsequently sequenced. To show that full length E6/E7 transcripts were produced, the HK1.E6/E7 cDNA was amplified using a 5' oligo #7 (5'-TATACCCCATGCTGCATGCC-3') that was specific for the deleted sequence produced by the alternative splicing that creates the E6*/E7 transcript, and oligo #2. To confirm that this transcript truly represented full length E6, this PCR product was digested with Xba I.

Microinjection of the HK1.E6/E7 construct gave numerous viable offspring and PCR analysis of tail tip DNA, employing vector-specific oligos #3 and #4, identified the presence of the transgene in seven founders. Northern analysis, using a vector specific probe, confirmed that three lines were high expressors. These lines were propagated to homozygosity. HK1.E6/E7 transgenic mice were indistinguishable from normal, non-transgenic siblings for the majority of their adult life, but once older than year (and more typically 16–20 months) HK1.E6/E7 mice began to exhibit small lesions underlying the fur. These lesions were initially identified by a roughness and a subtle rigidity of the skin, which occurred predominantly on the nape of the neck, back and dorsal ear surface. Following careful shaving and use of a depilatory cream, HK1.E6/E7 mice exhibited up to 15–20 pinpoint, raised structures, often with a scaly, keratotic cap.

These lesions were prone to regression, some disappearing within 6–8 weeks of the initial observation. Also, unlike transgenic mice expressing v-ras$^{Ha}$ or v-fos, the HK1.E6/E7 lesions did not appear to be associated with a wound promotion stimulus (e.g., ear tag). Not all animals were documented to possess these phenotypes. However due to the subtle nature of the lesions and their propensity to regress, these animals probably possessed unidentified lesions. Also, a second type of lesion appeared which was larger and more typical of a benign squamous cell papilloma. These papillomas appeared in old mice (18–21 months), grew slowly, and did not convert to malignant conversion.

Histopathology of HK1.E6/E7 Lesions and Keratin Immunofluorescence

Initially, the histotype of HK1.E6/E7 transgenic epidermis was indistinguishable from normal, non-transgenic siblings for all three lines, as was gingiva, vagina, anus and forestomach, which are possible alternate sites for mouse K1 expression. The earliest indications of HK1.E6/E7 induced pathology occurred in a 322 $F_1$ mouse #635 at approximately 10 months of age. The histotype is similar to a wart like lesion typically induced by HPV, consisting of a marked hyperplasia and hyperkeratosis, with a prominent stratum granulosum, and having distinct verrucous appendages descending from a highly keratotic plug. All histotypes of these subtle, verrucous lesions were identical.

Conversely, the second lesion histotype was confirmed as a typical, squamous cell papilloma with no areas of malignant conversion or carcinoma in situ. Frozen sections from epidermis, typical warts and papillomas were assessed for mouse keratin K1, K6, K13 and K14 expression by double label immunofluorescence. HK1.E6/E7 epidermis expressed keratins in an identical manner to normal, non-transgenic epidermis. While novel expression of the hyperproliferative keratin MK6 was observed in all lesions, they also retained MK1 expression, loss of which is observed in malignant conversion, indicating the benign nature of these lesions. Also, these lesions did not express K13, an early marker for malignant conversion. Thus both histotype and specific keratin markers confirmed the hyperproliferative but benign nature of the HK1.E6/E7 induced phenotypes.

Thus, it appears that the HK1.E6/E7 transgenic mice mimic not only the pathology, but also the epidemiology of HPV-16 or HPV-18 induced human disease, namely a long latency period between HPV induced preneoplastic disease and the onset of overt neoplasia.

The apparent delay and low phenotype frequency exhibited by these mice provides a relevant background to study the consequences of HPV expression during epithelial differentiation. In addition, these mice can be useful in assessing the efficacy of novel antisense pharmaceuticals which have been designed to inhibit expression of the E6 and E7 genes of HPV 18.

EXAMPLE 9

Analysis of HK1.E6/E7 Transcripts and ras$^{Ha}$ Activation

Due to latency and low lesion frequency, coupled to the alternative splicing available to the HPV18 E6/E7 region analysis of the transcripts produced by HK1.E6/E7 transgene expression was carried out. cDNA was generated from newborn epidermis representative of each line or a squamous papilloma using oligo #5 and amplified using oligos #6 and #2 as defined in Example 8. The ability to amplify across an intron using oligo #6 allowed assessment of DNA in RNA samples, but gave a slightly higher band size than that of the HPV.18 nco plasmid positive control, amplified by E6 and E7 specific oligos #1 and #2 as defined in Example 8. These experiments demonstrated the existence of two transcripts in epidermal and tumor RNA, with a similar upper to lower band intensity for epidermis and tumor. Subsequent Southern analysis showed that both of these PCR products were detected by an E6/E7 specific probe. That the more predominant lower 683 bp band represented the alternative splice E6*/E7 transcript was confirmed by cloning this amplified PCR product into a pGem3 vector and subsequent sequencing. The upper 873 bp band was confirmed to be a full length E6/E7 transcript by replacing oligo #6 with oligo #7 in the PCR amplification reaction. Oligo #7 is specific for the sequences lost on creation of E6*. This generated a 680 bp band in epidermal and papilloma RNA identical to the plasmid positive control. Diagnostic Xba I digestion of these PCR products give the expected 641 bp band, indicative of a full length E6 transcript. The verrucous lesions also possessed ratios of E6 to E6* transcripts identical to that of the $ras^{Ha}$ papilloma.

Since the latency of lesion appearance suggested the requirement for events additional to the transgene expression, the $ras^{Ha}$ oncogene was investigated for characteristic activating mutations. These have been well documented to occur spontaneously in mouse skin carcinogenesis and occur frequently in chemical carcinogenesis. cDNA generated from several verrucous lesions and squamous papillomas by random priming was amplified by c-$ras^{Ha}$ specific oligos and the PCR product subjected to single-strand sequencing. All verrucous lesions analyzed had a normal sequence at codons 12, 13 and 61. However while possessing a normal codon 12 and 13, the anogenital papilloma possessed an A→T transversion at codon 61. Conversely the neck papilloma had normal codons 12 and 61 but possessed a G→T mutation within codon 13.

Previously, it was observed that a HK1.ras transgene has profound effects in newborn but not adult epidermis (Greenhalgh, et al., Targeted Expression of v-$ras^{Ha}$ to the Epidermis of Transgenic Mice Induces Hyperplasia, Hyperkeratosis and Papillomas, Mol. Carcinog., Vol. 7, pp. 99–110 (1993)). That data indicated the necessity for cooperating genetic events additional to HK1.E6/E7 expression that lead to overt lesion appearance and eventual neoplasia. It is of interest that while the host factors that cooperate with HK1.E6/E7 to produce the verrucous lesions remain unknown, in the progression to a benign squamous cell papilloma, the $ras^{Ha}$ oncogene was found to be activated by an A→T transversion at codon 61 (c-$ras^{Ha61}$). This is typical of the mutations found in spontaneous or chemical activation of the murine c-$ras^{Ha}$ protooncogene. A second activating mutation (G→T) was detected at codon 13 (c-$ras^{Ha13}$) in a histologically identical squamous cell papilloma. These mutations were not detectable in the verrucous lesions and this suggests that squamous papillomas develop from a cooperation between the HK1.E6/E7 and the spontaneously activated endogenous c-$ras^{Ha}$ oncogene. Cooperation between HPV-16 and 18 and $ras^{Ha}$ has been observed previously in vitro and centered on E7 expression (Woodworth, et al., Recombinant Retrovirus Encoding Human Papillomavirus Type 18 E6 and E7 Simulate Proliferation and Delay Differentiation of Human Keratinocytes Early After Infection, Oncogene, Vol. 7, pp. 619–626 (1992)).

This is of note since, HK1.E6/E7 expression in the transgenic mouse epidermis is predominantly E6*/E7. This bears significance to the relevance of HK1.E6/E7 mice as a model for the human condition as approximately 10% of cervical carcinomas contain $ras^{Ha}$ mutations. Moreover, HPV-16 has recently been associated with squamous cell carcinomas etiology on sun exposed sites (Pierceall, et al., Presence of Human Papillomavirus Type 16 DNA Sequences in Human Non-melanoma Skin Cancers, J. Invest. Dermatol., Vol. 97, pp. 880–884 (1991)), up to 46% of which contain UV-induced activating $ras^{Ha}$ mutations (Pierceall, et al., Ras Gene Mutations and Amplification in Human Nonmelanoma Skin Cancers, Mol. Carcinog., Vol. 4, pp. 196–202 (1991)). Also, as HPV represents a serious problem for immune suppressed individuals (Broker, et al., A Molecular Portrait of Human Papillomavirus Carcinogenesis, pp. 197–207, In: Molecular Diagnostics of Human Cancer, Cancer Cells 7, Cold Spring Harbor, N.Y., (1989)), and given the frequency of $ras^{Ha}$ activation in human cancers (Bos, The ras Gene Family and Human Carcinogenesis, Mutant Res., Vol. 198, pp. 255–271 (1988)), the mating of HK1.E6/E7 mice with transgenic mice expressing activated $ras^{Ha}$ (HK1.ras) could prove a powerful system to explore gene synergism in vivo.

The HK1.E6/E7 transgene, being derived from HPV-18 DNA, contains an alternative splice site which augments the expression of E7 at the expense of a full length E6 transcript, producing the non-transforming E6* (Sedman, et al., The Full Length E6 Protein of Human Papillomavirus Type 16 has Transforming and Transactivating Activities and Cooperates with E7 to Immortalize Keratinocytes in Culture, J. Virol., Vol. 65, pp. 4860–4866 (1991)). Careful analysis of the HK1.E6/E7 transcripts showed that for all three lines, epidermis, verrucous lesions and papillomas expressed similar and predominant levels of the E6*/E7 transcript. The low levels of the full length E6 transcript, barely detectable in newborn epidermal RNA, remained unchanged in lesions or papillomas on comparison to the E6*/E7 transcript. Thus, the transgenic mice may be considered predominantly E7, hence the potential for cooperation with c-ras.

Since the data suggests the necessity of secondary and tertiary events in the low frequency and long latency for the development of HPV associated pathology in our mice may be a consequence of low level full length E6 expression. The full length E6, in addition to cooperating with E7 in immortalizing human keratinocytes, is capable of transforming murine NIH 3T3 cells in vitro (Sedman, et al., The Full Length E6 Protein of Human Papillomavirus Type 16 has Transforming and Transactivating Activities and Cooperates with E7 to Immortalize Keratinocytes in Culture, J. Virol., Vol. 65, pp. 4860–4866 (1991)), and the BPV E6 can immortalize human epithelial cells alone. Moreover, the HPV16 E6 gene was shown to cooperate with $ras^{Ha}$ and immortalize keratinocytes apparently independent of E7 (Story and Banks, Human Papilloma Virus Type 16 E6 Cooperates with EJ-ras to Immortalize Primary Mouse Cells, Oncogene, Vol. 8, pp. 919–924 (1993)). Therefore, the combination of functional E6 and E7 together with $ras^{Ha61}$, may be required to achieve either higher lesion frequencies (both verrucae and papillomas), and malignant conversion in this transgenic epidermal model.

Accordingly, it will be useful to produce an HK1.E6 mouse for mating purposes with the HK1.E6/E7 (i.e., E6*/E7) mice and HK1.ras. Furthermore, if progression to malignancy in HPV-16 and 18 infected tumors is contingent on E6 and E7 binding to the p53 and Rb tumor suppressor proteins, thereby inactivating their function), the mating of HK1.E6/E7 mice (i.e., E6*/E7) to those null for the p53 gene would give a functional in vivo murine equivalent to the putative E6/p53 interaction found in humans.

EXAMPLE 10

Production of Transgenic Mice Expressing TGF-α in the Epidermis

Transforming growth factor alpha (TGF-α) is a cytokine with structural and functional characteristics similar to epidermal growth factor (EGF). Both TGF-α and EGF bind to the epidermal growth factor receptor (EGF-R) and stimulate the tyrosine kinase cascade. TGF-α is expressed by both normal and transformed cells and causes proliferation of cultured keratinocytes. In vivo, TGF-α induces angiogenesis and is more potent than EGF in accelerating wound healing. In normal human skin, expression of TGF-α occurs in all layers of the epidermis and in certain areas of the appendages. Several cutaneous diseases such as psoriasis, squamous cell carcinoma, and congenital bullous ichthyosiform erythroderma have been associated with altered expression of TGF-α.

To determine whether altered expression of TGF-α plays a role in the pathogenesis of these diseases, the protein coding sequence of human TGF-α was inserted into the human keratin K1 targeting vector (FIG. 6).

Construction of the HK1.TGF-α Transgene

The targeting vector (pHK1) is derived from a 12 kb EcoRI fragment of the HK1 gene from lambda clone c55 (Johnson, et al., Structure of a Gene for the Human Epidermal 67 kDa Keratin, Proc. Natl. Acad. Sci. USA, Vol. 82, pp. 1896–1906 (1985)), that has been found to direct expression in a tissue-specific and developmental-specific fashion (Greenhalgh, et al., Induction of Epidermal Hyperplasia, Hyperkeratosis and Papillomas in Transgenic Mice by a Targeted v-Ha-ras Oncogene, Mol. Carcinog., Vol. 7, pp. 99–110 (1993); Greenhalgh, et al., Hyperplasia, Hyperkeratosis and Benign Tumor Production in Transgenic Mice by a Targeted v-fos Oncogene Suggest a Role for fos in Epidermal Differentiation and Neoplasia, Oncogene, Vol. 8, pp. 2145–2157 (1993)).

As previously described, this 10.8 kb fragment is missing certain regulatory elements which restrict expression to the differentiated compartment of the epidermis. This truncation allows expression of the transgene to be directed to 20–30% of the proliferative compartment of the epidermis (Rosenthal, et al., A Human Epidermal Differentiation Specific Keratin Gene is Regulated by Calcium but not Negative Modulators of Differentiation in Transgenic Mouse Keratinocytes, Cell Growth and Diff., Vol. 2, pp. 107–113 (1991)).

Briefly, through the use of PCR, all HK1 exons and introns, with the exception of the first intron, have been deleted and a polylinker with unique restriction enzyme sites was introduced 3' of the first intron. Thus, the targeting vector retains all of the 5' flanking sequence up to but not including the ATG, the first intron including the intron/exon splice site, and the 3' non-coding and flanking sequences after the TAA codon (FIG. 6). The EcoRI sites at the vector ends were retained and the vector cloned into pGem3 for bacterial amplification and replication. The sequence encoding human TGF-α cDNA (plasmid phTGF1-10-925 kindly provided by Dr. Graeme Bell, University of Chicago) was introduced into the HK1 vector by engineering unique Bam HI and Cla I restriction enzyme sites onto the 5' and 3' ends of the TGF-α cDNA by PCR through the use of TGF-α specific oligonucleotides #1 (5'AAACGCGG-ATCCATGGTCCCCTCGGCTGGA-3') and #2 (5'-CCATCGATGGTCAGACCACTGTTTCTGA-3'). This product was amplified and subcloned into the TA cloning vector (Invitrogen). The 50 μl reaction consisted of 5 μl of 10× PCR buffer (Invitrogen), 1 μl of 25 mM dNTP's, 1 μl of each primer and 4 units of *Thermus aquaticus* (Taq) DNA polymerase (Cetus). 30 PCR cycles of the following profile were used: 1 minute at 94° C., 2 minutes at 55° C., 3 minutes at 72° C., and finally 7 minutes at 74° C. After confirmation of the correct sequence, this 500 bp Bam HI-Cla I fragment of the TGF-α cDNA was subsequently subcloned into the Bam HI and Cla I sites of the HK1 targeting vector (FIG. 6).

Generation and Identification of Transgenic Mice

The pHK1-TGF-α plasmid was digested with EcoRI in order to release the transgene and the 6.7 kb fragment was isolated by agarose gel electrophoresis and paper purified. HK1.TGF-α DNA concentration was adjusted to 2 ng/ml in 10 mM Tris HCl, 0.25 mM EDTA pH 7.5 and ultracentrifuged at 40,000 rpm for 30 minutes. One cell mouse embryos were isolated from 10–12 gram ICR female mice (Charles River) mated to FVB male mice (Frederick Cancer Research Facility) and the transgene DNA was microinjected into the male pronucleus of the embryos (Johnson, et al., The Structure of the Gene for the Human Epidermal Keratin of 67,000 Molecular Weight, Proc. Natl. Acad. Sci. USA, Vol. 82, pp. 1896–1900 (1985)). These embryos were implanted into ICR pseudopregnant foster mothers. PCR analysis using oligonucleotides #3 (5'-TGGTCCACTTGGGATTGGTG-3') and #4 (5'-GGAGTCTCATAGCCATGG-3') specific for the first intron of the expression vector (FIG. 6) were used to confirm the presence of the transgene in tail tip DNA from 21 day old founder mice. The 100 μl PCR reaction consisted of 10 μl 10× buffer (Cetus), 2 μl each 10 mM DNTP, 1 μl diluted DNA, 1 μl each of 5' and 3' primers at 200 ng/μl, 78 μl H$_2$O, and 1 μl Taq DNA polymerase (Cetus). Samples were heated to 95° C. for 5 minutes, then 30 cycles of amplification consisted of denaturation at 95° C. for 30 seconds, annealing at 60° C. for 1 minute and extension at 72° C. for 1 minute, the final extension was at 72° C. for 15 minutes.

Northern and Reverse Transcriptase/PCR Analysis (RT/PCR)

Skins from newborn and adult mice (transgenic and control) were floated on 0.25% trypsin at 4° C. for 18 hours, after which the epidermis and dermis were separated as independent sheets (Yuspa, et al., Epidermal Cell Culture, Transplantation Proceedings, Vol. 12, Suppl. 1, pp. 114–122 (1980)). Total RNA was isolated from the epidermis using the RNAzol protocol (Biotex Laboratories). Following formaldehyde agarose gel electrophoresis and transfer to nitrocellulose, filters were hybridized with $^{32}$P-labelled random-primed probes corresponding to the 3' non-coding (3' NC) human keratin 1 sequence, or a TGF-αspecific sequence. Filters were washed to a stringency of 0.5 SSC 0.1% SDS at 68° C. prior to autoradiography at −70° C. using Kodak X-O-Mat AR5 film with an intensifying screen. To account for loading discrepancies, filters were reprobed with a probe specific for βactin.

Total RNA was also isolated from papillomas and stomach, brain, liver, kidney, and spleen and assessed for HK1.TGF-α expression by RT/PCR analysis. cDNA was generated by incubating 2-μg of total RNA with reverse transcriptase (Life Sciences, St. Petersburg, Fla.) according to the manufacturer's instructions and 200 ng of 3' NC specific oligo #5 (5'-ATCGACCTCGGTCTTGCC-3') at 37° C. for 2 hours. The resultant cDNA was amplified by PCR using TGF-α specific oligos #1 and #2 as outlined above to give an approximate 500 bp band indicative of HK1.TGF-α expression. Control reactions without reverse transcriptase were included to account for DNA contamination of RNA samples.

Radioimmunoassay

Epidermis from transgenic and control newborn mice was separated from dermis by heating in 0.15M NaCl at 68° C. for 2 minutes. Protein was extracted using three different methods. Acid/ethanol extraction as described by Robert, et al., Transforming Growth Factors: Isolation of Polypeptides from Virally and Chemically Transformed Cells by Acid/ethanol Extraction, Proc. Natl. Acad. Sci., USA, Vol. 77, pp. 3494–3498 (1980)), cytosol/membrane extraction as described by Imamato, et al., Evidence for Autocrine/paracrine Growth Stimulation by Transforming Growth Factor-α During the Process of Skin Tumor Promotion, Mol. Carcinog., Vol. 4, pp. 52–60 (1991), and total epidermal protein extraction.

Total epidermal protein extracts were prepared by homogenization in 0.0625M Tris-HCl, pH 6.8, 5% SDS, 10% glycerol, and 20% 2-mercaptoethanol followed by heating at 95° C. for 10 minutes. After a brief centrifugation step to remove insoluble material, the supernatant was dialyzed against TBS buffer containing 1 mM EDTA and 0.1% Triton X-100. Quantification of protein was performed as described by the Bradford assay and quantified by a TGF-α radioimmunoassay (Biomedical Technologies, Inc., Stroughton, Mass.).

Immunoprecipitation

Newborn HK1.TGF-α or control skin samples were trypsinized overnight at 4° C. and once separated from dermis (Yuspa, et al., Epidermal Cell Culture, Transplantation Proceedings, Vol. 12, Suppl. 1, pp. 114–122 (1980)), the epidermis was incubated in low calcium, cysteine-free EMEM containing 1 mCi S35-cysteine overnight at 37° C. The epidermis was then washed three times with PBS, centrifuged, and the pellet lysed in Tris-SDS-glycerol-mercaptoethanol buffer, followed by heating to 95° C. for 10 minutes and centrifugation. The resultant supernatant was dialyzed with RIPA buffer (1% NP-40, 0.1% aprotinin, 1% deoxycholate, 0.1% SDS, 150 mM sodium chloride, 1 mM EDTA, 1 mM PMSF, 20 mM MOPS pH 7.6) at room temperature for 24 hours.

Samples with $3 \times 10^6$ cpm were adjusted to a volume of 1 ml with RIPA buffer and normal rabbit serum (20 μl) added; the samples were incubated for 1 hour at 4° C. Continuing this pre-clearing step, 50 μl of goat antimouse IgG-agarose was then added for 1 hour at 4° C. After centrifugation, the supernatant was collected and incubated with 2 μg of TGF-α antibody (Oncogene Science) for 3 hours at 4° C. followed by addition of 50 μl of goat anti-mouse IgG-agarose and incubation for a further hour at 4° C. After centrifugation, the pellet was washed repeatedly with RIPA buffer and buffer containing 2.5M KCl and recentrifugated. Samples were resuspended in solubilization buffer and 50 μl aliquots were incubated with 0.32M iodoacetamide for 15 minutes at 37° C. Samples were then run on 12.5% tricine-SDS-PAGE gels and fixed in 40% methanol/10% acetic acid. After incubation with Enhance (Dupont) followed by water (30 minutes each), gels were dried and fluorographed.

Tissue Histology

Skin, liver, mammary gland, tongue, stomach, vagina, gingiva, and pancreatic tissues were fixed in Carnoy's solution (chloroform/acetic acid/ethanol 3:1:6 v/v) at 4° C. overnight, transferred to 95% ethanol, embedded in paraffin, sectioned and stained with hematoxylin and eosin.

Immunofluorescence

Biopsy samples were frozen in OCT at −70, sectioned at 4–6 microns and mounted onto glass slides. Slides were washed twice in PBS for 10 minutes and rinsed in distilled water for 2 minutes. Monospecific antikeratin antibodies from two species (Roop, et al., Regulated Expression of Differentiation Associated Keratins in Cultured Epidermal Cells Detected by Monospecific Antibodies to Unique Peptides of Mouse Epidermal Keratins, Differentiation, Vol. 35, pp. 143–150 (1987); Roop, et al., Transcriptional Control of High Molecular Weight Keratin Gene Expression in Multistage Mouse Skin Carcinogenesis, Cancer Res., Vol. 48, pp. 3245–3252 (1988); Nischt, et al., Abberant Expression During Two Stage Mouse Skin Carcinogenesis of a Type I 147-kDa Keratin, K13, Normally Associated with Terminal Differentiation of Internal Stratified Epithelia, Mol. Carcinogen., Vol. 1, pp. 96–108 (1988); Smith, et al., Differential Keratin Gene Expression in Developing, Differentiating, Preneoplastic and Neoplastic Mouse Mammary Epithelium, Cell Growth and Diff., Vol. 1, pp. 161–170 (1990)), were applied overnight at room temperature.

The following dilutions were prepared in 12% BSA/PBS (v/v): guinea pig anti K14 1:2000, rabbit anti K1 1:500, rabbit anti K6 1:2000, rabbit anti K13 1:500, rabbit anti loricrin (Mehrel, et al., Identification of a Major Keratinocyte Cell Envelope Protein, Loricrin, Cell, Vol. 61, pp. 1103–1112 (1990)), 1:500 and rabbit anti filaggrin (Rothnagel, et al., The Structure and Expression of the Mouse Epidermal Filaggrin Precursor Gene, J. Biol. Chem., Vol. 262, pp. 15643–15648 (1987)) 1:500. Sections were washed as above and secondary biotinylated goat anti guinea pig 1:100 (Vector), along with normal goat 1:100 and swine serum 1:100, were applied for 30 minutes at room temperature. Sections were washed again and 1:400 Streptavidin-Texas Red (Gibco) and 1:40 swine anti rabbit FITC (Dakopatts) were applied for 30 minutes at room temperature. Sections were washed, air dried, and cover-slipped with Fluoromount (Fisher Biotech).

Bromodeoxyuridine Uptake and Staining

Samples were processed as previously described (Huitfeldt, et al., Altered Regulation of Growth Expression of Differentiation Associated Keratins in Benign Mouse Skin Tumors, Carcinogen., Vol. 12, pp. 2063–2067 (1991)). Briefly, newborn transgenic and control mice were injected (i.p.) with BrdUrd (Sigma) 250 mg/kg in 0.9% NaCl and sacrificed after 2 hours. Dorsal and ventral skin was fixed in 70% ethanol at 4° C. and embedded in paraffin. Sections were cut, deparaffinized, and soaked in 2N HCl for 30 minutes. Sections were then washed in PBS, placed in 70% ethanol with 0.1M Tris twice for 10 minutes, switched to 70% ethanol twice for 5 minutes, rehydrated, and dried. Sections were incubated with undiluted FITC-conjugated monoclonal antibody to BrdUrd (Becton-Dickinson) mixed with guinea-pig antiserum to K14 (diluted 1:2000) for 20 hours. Sections were washed twice in PBS for 10 minutes, rinsed in distilled water, incubated with 1:100 goat anti guinea pig biotinylated antibody (Vector) for 30 minutes. After washing, 1:400 Streptavidin-Texas Red (Gibco) was applied for 30 minutes and sections were again washed, dried, and mounted with Fluoromount (Fisher Biotech).

Phenotypic Expression

Injection of the HK1.TGF-α construct into embryos resulted in phenotypic founders that were quite similar to that of ras$^{Ha}$. PCR analysis of tail DNA using oligonucleotides specific for the first intron of HK1 (oligo #3 and #4,) confirmed the presence of the transgene in 10 founders. Subsequent northern analysis of F1 neonatal epidermal RNA confirmed that eight were expressors (1960, 1970, 1981, 2032, 2034, 2106, 2113, 5418). Seven of the founders and their progeny had a markedly thickened, opalescent skin at birth, and this phenotype persisted until growth of the first coat of hair. Founder 1981 had a very subtle phenotypic pattern that became more apparent in the $F_1$ generation. Affected newborn pups were often smaller in size compared to normal littermates and at 6–8 days of age, the HK1.TGF-α pups exhibited precocious eye opening compared to 10–12 days in normal litter mates. By 7–8 days of age, control littermates had growth of the first coat of hair whereas transgenic pups had diffuse alopecia with thickening and scaling of the skin that persisted until days 16–21. Five lines (1970, 2032, 2034, 2113 and 5418) had fine, sparse hair as compared to normal.

Three lines (1970, 2032, and 2113) retained the phenotype of thick, scaly skin as adults. The adult phenotype varied from uniform involvement of the abdominal and genital areas to focal involvement of areas like the head and neck, and may have been induced and sustained by trauma or mechanical irritation. These lines also demonstrated areas of hyperkeratosis and the appearance of spontaneous papillomas at 2-5 months of age. Generally, papillomas appeared at sites prone to wounding (ear tag) or repeated trauma (scratching and biting).

The founder mouse 2032 exhibited small papillomas in the inguinal region, with spontaneous resolution in 2-3 weeks. A typical derivative from the 1970 line had the appearance of multiple small papillomas on the upper back and ears that became large, ulcerative papillomas over a 5 month period, but then began to regress. This regression of papillomas was frequently observed. Autopsies of mice from several different lines demonstrated no gross changes in the mammary gland, liver, pancreas, oral epithelia, or forestomach and the HK1.TGF-α mice appeared to have a normal lifespan.

Histology

Histologic examination of newborn, 8 day old, and adult phenotypic transgenic skin showed marked epidermal hyperplasia with hyperkeratosis of the stratum corneum, preservation of the granular layer, and hypertrophy of the stratum malpighii, and relatively fewer hair follicles as compared to normal. The dermis was somewhat thinner than normal. No abnormal histologic changes were noted in the mammary gland, liver, pancreas, forestomach, or oral mucosa. Biopsies of the papillomas showed marked hyperkeratosis, acanthosis, papillomatosis, and a moderate dermal inflammatory infiltrate, consistent with a well differentiated squamous papilloma. Minimal dysplasia was occasionally seen focally but no frank carcinoma in situ was present.

Expression of HK1.TGF-α in Epidermis and Papillomas

Expression of HK1.TGF-α in the epidermis of phenotypic newborn pups and adults was confirmed by northern analysis of F1 neonatal RNA using a vector specific 3' non-coding (3' NC) probe. A 0.9 kb band, corresponding to the expected size of the HK1.TGF-α mRNA, was seen in all phenotypic epidermis. Identical results were obtained with a TGF-α specific probe. After reprobing with a βactin probe to assess for loading discrepancies, the more severely affected lines demonstrated greater intensity of signals. RT/PCR analysis was employed to detect HK1.TGF-α transcripts in phenotypic adult epidermis and papillomas, and identified the expected 500 bp band. This technique was primarily employed to assess other tissues for transgene expression and this band was absent in experiments involving template RNA isolated from stomach, brain, kidney, liver, lung and spleen, consistent with the expression properties of the vector and the absence of pathology outside the epidermis.

To assess HK1.TGF-α protein expression, $^{35}$S labelled epidermal extracts from phenotypic and control mice were analyzed by immunoprecipitation. In the control sample, a faint 21 kD band that corresponded to the relative mobility of the precursor endogenous TGF-α species was seen. In contrast, transgenic samples had a prominent band appearing around 15 kD which corresponded to the relative mobility of a TGF-α degradation product remaining after cleavage of mature 6 kD TGF-α species. To quantitate the level of human TGF-α, radioimmunoassays were performed. The concentration of human TGF-α in transgenic epidermal extracts varied between 2.4~16.0 ng/mg protein, and the severity of the skin changes correlated with the level of TGF-α expression. Using acid/ethanol extraction, human TGF-α protein levels were enriched approximately 10-fold in the transgenic epidermis. Fractionation into epidermal cystolic and membrane components showed demonstrable increases in both compartments with the majority of the protein appearing in the cystolic fraction.

HK1.TGF-α Transgenic Mice Demonstrate Aberrant Keratin Expression and Hyperproliferation of the Epidermis To assess potential changes in markers of epidermal differentiation and proliferation, frozen sections from normal and transgenic mouse skin and papillomas were analyzed by double-label immunofluorescence (IF) with antibodies to K1, K6, K13, K14, loricrin and filaggrin. Under normal conditions, K14 is expressed in basal cells and is transcriptionally down-regulated once cells commit to terminal differentiation (Mehrel, et al., Identification of a Major Keratinocyte Cell Envelope Protein, Loricrin, Cell, Vol. 61, pp. 1103–1112 (1990)). However, K14 staining is seen to persist into upper layers of the epidermis because of the inherent stability of keratin proteins. K1, an early marker of terminal differentiation, is detected throughout the suprabasal layers, as well as in some basal cells (Roop, et al., Transcriptional Control of High Molecular Weight Keratin Gene Expression in Multistage Mouse Skin Carcinogenesis, Cancer Res., Vol. 48, pp. 3245–3252 (1988)), however, expression in basal cells occurs post-mitotically (Huitfeldt, et al., Altered Regulation of Growth Expression of Differentiation Associated Keratins in Benign Mouse Skin Tumors, Carcinogen., Vol. 12, pp. 2063–2067 (1991)).

While normal control and transgenic epidermis had the appropriate expression of K14, expression of K1 was delayed in transgenic epidermis and papillomas, presumably due to expansion of the proliferative compartment. K6, a marker of hyperproliferation (Weiss, et al., Monoclonal Antibody Analysis of Keratin Expression in Epidermal Diseases: A 48- and 56-Kilodalton Keratin as Molecular Markers for Hyperproliferative Keratinocytes, J. Cell Biol., Vol. 98, pp. 1397–1406 (1984)), and other pathological conditions (Sellheyer, et al., Inhibition of Skin Development by Over-expression of Transforming Growth Factor-β1 in the Epidermis of Transgenic Mice, Proc. Natl. Acad. Sci. USA, Vol. 90, pp. 5237–5241 (1993)), was expressed throughout the epidermis of hyperplastic neonatal skin and in papillomas, but was restricted to expression in hair follicles in normal controls. Expression of both loricrin and filaggrin, late markers of terminal differentiation was not altered in hyperplastic skin. No expression of K13, an early marker of malignant conversion, was seen in papillomas, which also retained K1 expression confirming their benign nature.

To assess potential changes in the proliferative compartment of phenotypic epidermis, normal and transgenic mice were labeled with BrdUrd for 2 hours prior to sacrifice. Staining with an anti-BrdUrd antibody shows a marked increase in mitotically active cells in transgenic epidermis over controls. Control epidermis had 32.2 (±5.8) labeled nuclei per mm, whereas transgenic epidermis had 60.5 (±10.6) labeled nuclei per mm. In addition, labeled nuclei were detected in suprabasal epidermal cells of HK1.TGF-α mice, confirming expansion of the proliferative compartment into the stratum spinosum.

In summary, the expression of human TGF-α was successfully targeted exclusively to the epidermis of transgenic mice using a vector derived from the HK1 gene. Eight transgenic founder lines were established which exhibited similar characteristics, with variations in severity dependent upon the expression levels of TGF-α. Over-expression of TGF-α in the epidermis resulted in transgenic mice whose phenotypes were immediately obvious at birth. These affected mice were smaller and had a markedly thickened and wrinkled skin, sparse thin hair, and epidermal hyperplasia and hyperkeratosis.

This example documents the potential pathological consequences of deregulated expression of TGF-α in the epidermis. Therapeutic strategies designed to inhibit TGF-α expression or interfere with its signal transduction pathway would be expected to prove efficacious in the treatment of certain hyperproliferative skin diseases, and this transgenic model would be expected to be useful in assessing these protocols.

EXAMPLE 11

Effect of on EGFR Expression in Transgenic Mice Expressing TGF-α in the Epidermis EGFR Levels and EGF Binding In vitro studies suggest that TGF-α may regulate EGFR expression (Clark, et al., Epidermal Growth Factor Regulates the Expression of its Own Receptor, Proc. Natl. Acad. Sci. USA, Vol. 82, pp. 8374–8378 (1985); Earp, et al., Epidermal Growth Factor (EGF) Stimulates EGF Receptor Synthesis, J. Biol. Chem., Vol. 261, pp. 4777–4780 (1986); Kudlow, et al., Epidermal Growth Factor Stimulates the Synthesis of its Own Receptor in a Human Breast Cancer Cell Line, J. Biol. Chem., Vol. 261, pp. 4134–4138 (1986)), and in hyperproliferative conditions, is associated with persistent EGFR expression into the upper layers of the epidermis. Therefore, the distribution of EGFR in HK1.TGF-α transgenic mice was analyzed for potential alterations. Skin samples removed from normal adult mice showed intense immunoreactivity for EGFR in interfollicular epidermis, follicular epithelia and sebaceous glands. In adult HK1.TGF-α mice, the distant non-phenotypic skin had an immunolocalization pattern for EGFR identical to that observed in normal mouse skin. When phenotypic skin from three different HK1.TGF-α adult mice were evaluated for the presence of EGFR, a drastically different staining pattern was observed. Within these lesions no specific immunoreactivity for EGFR was detectable in either the epidermal layers at the surface or in the ridges extending into the underlying dermal regions. The validity of this observed negative immunostaining pattern was tested by including serial sections of these samples in three separate immunostaining experiments with sections that stained positive for EGFR. In addition, a longer reaction time with DAB only produced weak non-specific staining of adjacent dermis and the cornified layers. Nevertheless, relatively non-affected epidermis immediately adjacent to the phenotypic site showed the same strong immunostaining for EGFR as observed in both the normal adult epidermis and non-phenotypic epidermis at a more distal location.

When normal neonatal mouse skin was stained for EGFR, intense immunostaining was present in the interfollicular epidermis but only a faint immunostaining for EGFR was present in the growing hair follicles. By contrast, the hypertrophic sites of neonatal skin removed from a HK1.TGF-α mouse showed the complete absence of immunoreactive EGFR in the epidermis.

Additional data indicating that EGFR were downregulated in the phenotypic epidermis of newborn HK1.TGF-α mice were obtained from $^{125}$I EGF binding studies. Control newborn mice exhibited prominent $^{125}$I EGF binding in the basal and spinous layers of the epidermis as well as in hair follicles. A marked reduction in $^{125}$I EGF binding was observed in phenotypic skin. The highest levels of binding were detected in hair follicles and the adjacent epidermis.

EGFR Immunohistochemical Localization

For EGFR immunohistochemical staining, frozen sections were fixed in acetone for 10 minutes, rinsed in PBS and blocked in 5% goat serum for 20 minutes. Sections were then incubated for 18 hours at 4° C. in either EGFR polyclonal antisera or non-specific sera at a dilution of 1:500 using slight modifications to previously published protocols (Nanney, et al., Epidermal Growth Factor Receptors in Idiopathic and Virally Induced Skin Diseases, Am. J. Path., Vol. 140, pp. 915–925 (1992)). Skin sections were rinsed and reacted with the immune reagents in an avidin-biotin complex kit (Vector Laboratories). Immunoreactive sites in the mouse tissues were visualized using 3,3-diaminobenzidine as the chromagen.

EGFR Binding

Localization of EGFR binding by autoradiography was performed as previously described (Nanney, et al., Comparison of Epidermal Growth Factor Binding and Receptor Distribution in Normal Human Epidermis and Epidermal Appendages, J. Invest. Dermatol., Vol. 83, pp. 385–393 (1984)).

Approximately 1 mm$^2$ skin samples from newborn transgenic and control mice were incubated in 0.5 ml of Hank's balanced salt solution with 1 mg/ml BSA, 20 mM HEPES pH 7.4, and 10 ng/ml $^{125}$I EGF for 90 minutes at room temperature. Samples were then repeatedly washed in salt solution for 90 minutes at room temperature, fixed in 10% buffered formalin for 4 hours, and processed for light microscopy. Sections were placed in a 1:1 dilution of NTB-2 emulsion in water and exposed for 4 weeks at 4° C. The emulsion was developed using 1:1 dilution of Kodak Dektol for 2 minutes at 15° C., water stop bath for 20 seconds at 15° C., and 1:3 dilution of Kodak Kodafix solution in water for 5 minutes at 15° C. Sections were rinsed in water for 10 minutes, dried, stained with hematoxylin and eosin, and mounted with Permount.

EXAMPLE 12

Production of Transgenic Mice Expressing TGF-$\beta_1$ in the Epidermis

The pHK1 epidermal-specific targeting vector was also used to target a constituitively active form of TGF-$\beta_1$ to the epidermis of transgenic mice (Roche, et al., Inhibition of Skin Development by Over-expression of Transforming Growth Factor-β1 in the Epidermis of Transgenic Mice, Proc. Natl. Acad. Sci. USA, Vol. 90, pp. 5237–5241 (1993), incorporated herein by reference). These mice exhibited a severe skin phenotype resulting from complete suppression of epidermal cell proliferation. The skin of these animals was very shiny and tautly stretched, and this appeared to restrict their ability to move and breath; death occurred within 24 hours. Both of these studies document the profound phenotypic effects that result from deregulated expression of positive and negative growth factors in the epidermis of transgenic mice.

These results are in marked contrast to recent data generated via targeted disruption of the TGF-α and TGF-$\beta_1$ genes. Mice with a null mutations of the TGF-α gene exhibited a waviness of whiskers and fur and misalignment of hair follicles, but otherwise the skin appeared normal and wound healing was not impaired (Mann, et al., Mice with a Null Mutation of the TGF-α Gene Have Abnormal Skin Architecture, Wavy Hair, and Curly Whiskers and Often Develop Corneal Inflammation, Cell, Vol. 73, pp. 249–261 (1993); Luetteke, et al., TGF-α Deficiency Results in Hair Follicle and Eye Abnormalities in Targeted and Waved-1 Mice, Cell, Vol. 73, pp. 263–278 (1993)).

Although targeted disruption of the TGF-$\beta_1$ gene resulted in death at about 3–4 weeks after birth from multifocal inflammatory disease, no histological changes were detected in the skin (Shull, et al., Targeted Disruption of the Mouse Transforming Growth Factor-$\beta$1 Gene Results in Multifocal Inflammatory Disease, Nature, Vol. 359, pp. 693–699 (1992); Kulkarni, et al., Transforming Growth Factor $\beta$1 Null Mutations in Mice Causes Excessive Inflammatory Response and Early Death, Proc. Natl. Acad. Sci. USA, Vol. 90, pp. 770–774 (1993)).

The failure of TGF-α and TGF-$\beta_1$ null mice to manifest severe skin phenotypes suggests that there may be functional redundancy among the ligands that bind EGF and TGF-$\beta$ receptors in this tissue, and underscores the value of studies that utilize deregulated expression of these ligands in determining their role in normal and abnormal epidermis.

EXAMPLE 13

Production of Transgenic Mice Expressing the HIV tat Gene in the Epidermis

Patients infected with the human immunodeficiency virus (HIV) are at high risk for the development of specific AIDS-associated cutaneous disorders. Often patients manifesting symptoms have skin lesions ranging from hyperproliferative conditions such as psoriasis to Kaposi's sarcoma and metastatic basal cell carcinoma. The precise role of HIV genes, the cells of origin and hence etiology of such skin lesions remains unknown. It may be that specific HIV genes, e.g., the trans-regulatory protein tat, play a role directly or indirectly on the homeostatic mechanisms of host cells and tissues. Alternatively, the HIV tat gene may interact with or activate other viral genes present from latent or opportunistic infections, e.g., human papilloma virus (HPV). To directly assess the role of keratinocytes in the development of AIDS-associated cutaneous disorders, the HIV tat gene is targeted to the epidermis of transgenic mice. Targeting of the tat gene and exclusive expression in keratinocytes is achieved by the use of the human keratin K1 vector (FIG. 7). The development of strains of mice which develop cutaneous lesions with predictable kinetics as a result of expression of the HIV tat gene alone or in combination with other oncogenes serves as a useful model for assessing therapeutic potential of antisense pharmaceuticals designed to inhibit expression of the HIV tat gene.

EXAMPLE 14

Utilization of the HK1 Vector for Gene Therapy Applications

Where exclusive expression in epidermal cells is desirable and for transient expression the HK1 vector is an excellent choice for gene therapy. Unlike the human keratin K1 gene itself, the human keratin K1 vector derived from the 12 kb fragment is expressed in proliferating basal cells in the epidermis. In more recent transgenic experiments, it has been determined that a larger fragment containing the human keratin K1 gene, a 18 kb EcoRV fragment (Shown schematically in FIG. 8), is expressed exactly like the endogenous mouse K1 gene, i.e., post mitotically in cells committed to terminal differentiation. These cells are programmed to die and will eventually slough into the environment. Therefore, for human applications where transient expression is desired, it is possible to design a vector that will only be expressed in cells after they commit to terminal differentiation and begin moving upward toward the outer layers of the epidermis. The vector will be expressed approximately 10–14 days prior to being shed into the environment. This can be accomplished by inserting additional 5' flanking sequences from the 18 kb EcoRV fragment onto the end of the original human keratin K1 vector (See FIG. 9). Smaller portions of this 5' region can be chosen to provide this function using standard methodology (as for 3' regions).

EXAMPLE 15

Detection of Carcinogens and Tumor Promoters

Short-term tests (STTs) for genotoxic chemicals were originally developed as fast, inexpensive assays to assess the potential hazard of chemicals to humans. However, a recent report summarizing the results of a project initiated by the National Toxicology Program to evaluate the ability of STT's to predict rodent carcinogenicity questions the validity of relying solely on STT's. Three of the most potent carcinogens, detected in the rodent assays, produced no genetic toxicity in any of the four STTs evaluated (Tennant, et al., Science, Vol. 236, pp. 933–941 (1987)). Thus, to receive EPA/FDA approval for new compounds, chemical, agricultural, food and drug companies are currently required to perform two year animal tests costing up to $2 million. The development of new transgenic strains of mice that have been genetically engineered to rapidly detect carcinogens and tumor promoters would substantially reduce the overhead cost of long-term animal studies. The suitability of the transgenic mouse lines claimed in this patent application for rapid detection of carcinogens is initially determined with a known skin carcinogen, DMBA, to determine whether benign lesions appear earlier than in control non-treated litter mates. To determine suitability for detecting tumor promoters, a known promoter, 12-O-tetra-decanoylphorbol-13-acetate (TPA) is applied to ras$^{Ha}$, and fos mice. Since benign lesions in ras$^{Ha}$ mice and hyperplasia in fos mice appeared at sites of wounding (i.e., tagged ears), and wounding can promote tumor formation, these lines are useful for these studies.

EXAMPLE 16

Cell Type and Differentiation-specific Regulatory Elements Controlling Expression of Keratin K1 Gene The mammalian epidermis is composed of four histologically defined layers each of which represents a distinct stage of differentiation of the epidermal keratinocyte. Keratinocytes are the major cell type of the epidermis and arise from stem cells in the basal layer. Upon commitment to differentiation they lose their proliferative potential and migrate to the spinous layer. With further maturation they enter the granular layer and finally terminate as cornified squames in the stratum corneum before being sloughed into the environment. The degree of differentiation can also be defined biochemically by the expression of marker proteins that characterize each stage. For instance, basal keratinocytes express keratins K5 and K14 (Fuchs and Green, Cell, Vol. 19, pp. 1033–1042 (1980); Woodcock-Mitchell, et al., J. Cell. Biol., Vol. 95, pp. 580–588 (1982)). Once they enter the differentiation pathway to become spinous layer cells, they down regulate the genes for K5 and K14 and up regulate the genes for the differentiation-specific keratins, K1 and K10 (Roop, et al., Proc. Natl. Acad. Sci. USA, Vol. 80, pp. 716–720 (1983); Schweizer, et al., Cell, Vol. 37, pp. 159–170 (1984); Reganier, et al., J. Invest. Dermatol., Vol. 87, pp. 472–476 (1986)). The expression of K1 precedes that of K10 and is one of the earliest events in keratinocyte differentiation. K1 can be observed in the occasional basal cell that has already ceased mitotic activity and is about to migrate into the spinous layer. Transcription of K1 and K10 is restricted to spinous layer cells and when these mature into granular layer cells, the genes for K1 and K10 are down regulated and other genes, notably loricrin and filaggrin are induced.

Both in vitro and in vivo studies have implicated calcium as a major modulator of epidermal differentiation. A calcium gradient has been identified in the epidermis with the basal and spinous layers having calcium levels much lower than that observed in serum and rising to much higher than serum levels in the upper granular layer and stratum corneum (Malmqvist, et al., Nucl. Instrum. Methods Phys. Res., Vol. 3, pp. 611–617 (1984); Menon, et al., J. Invest. Dermatol., Vol. 84, pp. 508–512 (1985)). In vitro studies have shown that keratinocytes maintain their proliferative capacity when calcium levels of the culture medium are kept below 0.1 mM and that differentiation ensues with calcium levels of 0.1 mM or higher (Hennings, et al., Cell, Vol. 19, pp. 245–254 (1980)). Moreover, differentiation-specific genes including keratins K1 and K10 can be induced in cultured keratinocytes by raising the level of calcium in the medium (Roop, et al., Differentiation, Vol. 35, pp. 143–150 (1987); Yuspa, et al., J. Cell Biol., Vol. 109, pp. 1207–1217 (1989)).

In contrast, retinoic acid appears to suppress epidermal differentiation and indeed, promotes an undifferentiated phenotype in keratinocytes in culture (Yuspa and Harris, Exp. Cell Res., Vol. 86, pp. 95–10517 (1974)). Expression of the differentiation-specific markers are also suppressed; including K1 and K10 (Roop, et al., Differentiation, Vol. 35, pp. 143–150 (1987); Fuchs and Green, Cell, Vol. 25, pp. 617–625 (1981)) loricrin (Hohl, et al., J. Invest. Dermatol., Vol. 96, pp. 414–418 (1991)) and filaggrin (Asselineau, et al., Differentiation, Vol. 45, pp. 221–229 (1990)). In addition, a retinoic acid gradient may also exist in the epidermis, with high levels in the basal layer declining to much lower levels in the differentiated layers (Vahlquist, et al., Upsala J. Med. Sci., Vol. 92, pp. 253–257 (1987)).

Another regulator of epidermal differentiation is the active metabolite of Vitamin $D_3$, 1,25 dihydroxyvitamin $D_3$. It has been shown that Vitamin $D_3$ is a potent inhibitor of proliferation (Matsumoto, et al., Biochem. Biophys. Res. Commun., Vol. 166, pp. 916–923 (1990)) and moreover, will promote the differentiation of spinous and granular cells into the corneocytes of the stratum corneum (Hosomi, et al., Endocrinology, Vol. 113, pp. 1950–1957 (1983); Regnier and Darmon, Differentiation, Vol. 47, pp. 173–188 (1991)). Vitamin $D_3$ is produced by keratinocytes and autoradiographic studies suggest a concentration of 1,25-dihydroxyvitamin $D_3$ in the suprabasal layers of the epidermis (Stumpf, et al., Cell Tissue Res., Vol. 238, pp. 489–496 (1984)). Until now, a direct role for Vitamin $D_3$ on epidermal keratin gene expression has not been reported (Blumenberg, et al., J. Invest. Dermatol., Vol. 98, pp. 42s–49s (1992)).

The best studied example of transcription factors that regulate the differentiation-specific genes of the epidermis is the HK1 gene. A 10.8 kb transgene, containing nucleotides −1246 to +9495 from HK1, was correctly regulated with respect to tissue and developmental specificity in transgenic mice (Roop, et al., in: The Biology of Wool and Hair (Rogers, G. E., Reis, P. J., Ward, K. A., and Marshall, R. C. eds), pp. 311–324, Chapman and Hall, New York (1988); Roop, et al., in: Pharmacology of Retinoids in the Skin (Reichert, U., and Shroot, B., eds.) pp. 1–7, S. Karger, Basal (1989); Rosenthal, et al., Cell Growth and Differentiation, Vol. 2, pp. 107–113 (1991)). Furthermore, the expression of HK1 in keratinocytes cultured from these mice could be induced by the addition of calcium to the medium (Rosenthal, et al., Cell Growth and Differentiation, Vol. 2, pp. 107–113 (1991)). These studies suggested that the transgene encodes all the cis-acting regulatory elements necessary to mediate the calcium response. Recently, an array of regulatory elements that respond to increased calcium levels in vitro were identified and found to reside within a 4.4 kb fragment, 3' of the HK1 gene (Huff, et al., J. Biol. Chem., Vol. 268, pp. 377–384 (1993)). The sequences that mediate the calcium response have recently been defined to a 249 bp fragment that lies 7.9 kb downstream of the HK1 promoter (Rothnagel, et al., J. Invest. Dermatol., Vol. 101, pp. 506–513 (1993)).

A detailed analysis of the 249 bp fragment that encodes the calcium response element (CaRE) was performed. Footprinting and mobility shift assays have identified adjacent cis-elements. One of these encodes an AP-1 element to which all of the calcium response can be attributed. The adjacent region encodes a hormone responsive element through which both vitamin $D_3$ and retinoic acid are able to modulate the calcium response.

Plasmids and Constructs

The plasmid PHIVLTR.CAT (Rosen, et al., Cell, Vol. 41, pp. 813–823 (1985)), was used as a control. Details on the generation of the 249 bp fragment that encodes the calcium response element (CaRE) have been given elsewhere (Rothnagel, et al., J. Invest. Dermatol., Vol. 101, pp. 506–513 (1993), hereby incorporated by reference). Briefly, the 249 bp (+7820 to +8069 (numbering of base pairs is with respect to the start of HK1 transcription)) fragment was generated by polymerase chain reaction and cloned using Bgl II and Bam HI restriction sites into the plasmid vector pSP72 (Promega, Madison, Wis.). The 249 bp fragment was subsequently self ligated into four tandem repeats and inserted into the Bgl II site of pA10CAT$_2$ in an antisense orientation relative to the CAT (chloramphenicol acetyl transferase) gene. This construct is referred to as p249$^b$ in Rothnagel, et al., J. Invest. Dermatol., Vol. 101, pp. 506–513 (1993), and in this specification as CaRE.CAT. The constructs, CaREΔA.CAT and CaREΔB.CAT, were similarly constructed from CaREΔA and CaREΔB. These versions of the 249 bp fragment were created using polymerase chain reaction (Higuchi, in: PCR Technology, Principles and Applications for DNA Amplification (Erlich, H. A. ed) pp. 61–70, Stockton Press, New York (1989), to delete the entire protected region defined by footprint analysis. CaREΔA is lacking nucleotides +7895 to +7921 and CaREΔB is lacking nucleotides +7924 to +7948.

Cell culture and Transfection

Primary murine keratinocytes were cultured and transfected as described in Harper, et al., J. Invest. Dermatol., Vol. 91, pp. 150–153 (1988). Five micrograms of plasmid DNA plus 25 µg carrier DNA were transfected by calcium phosphate in medium containing 0.1 mM potassium to block calcium induced differentiation Id. After 24 hours, the transfected cells were switched to medium containing 0.05 mM calcium and 24 hours later switched to media containing the appropriate concentrations of calcium, 12-0- tetradecanoylphorbol-13-acetate (TPA), or steroid hormones. Cells were harvested after 48 hours in these media and assayed for CAT activity (Gorman, et al., Mol. Cell. Biol., Vol. 2, pp. 1044–1051 (1982)). The CAT assays were normalized by protein content and activity visualized by autoradiography after separation by thin layer chromatography. These experiments were repeated at least three times.

Nuclear Extracts

Nuclear extracts were made from primary murine keratinocyte cultures and prepared essentially as described by Dignam, et al., Nucleic Acid Res., Vol. 11, pp. 1475–1489 (1983). The protein concentration of each extract was determined by the Bradford assay (Bradford, Anal Biochem., Vol. 72, pp. 248–254 (1976)). Aliquots of nuclear extracts were stored at −80° C.

Band Shift Assay

Purified fragments of either the intact CaRE, CaREΔA or CaREΔB were end-labeled at the Bgl II site with DNA polymerase Klenow fragment and [$^{32}$P]dATP (3,000 Ci/mmol). Each $^{32}$P-labeled DNA fragment (10–20 fmol, $10^5$ cpm) was incubated with 2–4 μg nuclear protein extract and 3 μg nonspecific DNA poly (dI/dC) for 15 minutes at room temperature in 20 μl of binding buffer [20 mM HEPES (pH 7.8), 60 mM KCl, 2 mM dithiothreitol, 2.5 mM $MgCl_2$ and 2% Ficoll]. The mixtures were loaded directly onto a 4% polyacrylamide gel and electrophoresed at 30 mA at room temperature for 2 hours. The gels were dried and analyzed by autoradiography.

DNase 1 Footprinting

End labeled probes for footprinting were prepared as described above. Each labelled DNA probe (20–40 fmol) was incubated with 2–8 μg nuclear protein extract or one footprinting unit of purified c-Jun (Promega), 20 ng of poly (dI/dC) and binding buffer (see above) to a total reaction volume of 20 μl. After 15 minutes incubation at room temperature, the reaction was terminated by addition of 100 μl of stop solution containing 1 μg pBR322 plasmid DNA, 15 mM EDTA, 0.15% SDS and 1.5 μg of proteinase K. Samples were analyzed as described by Pastoricic, et al. (Pastoricic, et al., Mol. Cell. Biol., Vol. 6, pp. 2784–2791 (1986)).

Oligonucleotides

All oligonucleotides are double-stranded (only one strand is shown).
AP-1 (Promega) 5'-CGCTTGATGAGTCAGCCGGAA-3'
NS (NON SPECIFIC) 5'-GGCCTGGGGCTCTAGAGG-AAGCCGG-3'

The following sequences are from Umesono, et al., Cell, Vol. 65, pp. 1255–1266 (1991):
VDRE (DR3) 5'-AGCTTCAGGTCAAGGAGGTCAGAG-AGCT-3'
TRE (DR4) 5'-AGCTTCAGGTCACAGGAGGTCAGAG-AGCT-3'
RARE (DR5) 5'-AGCTTCAGGTCACCAGGAGGTCA-GAGAGCT-3'

Identification of Nuclear Protein-DNA Interactions Within the CaRE of HK1

Sequences within a 249 bp fragment located between +7820 to +8069 relative to the transcription start site of HK1 have been shown to direct transcription of both heterologous and homologous promoters in a cell-type specific manner in response to increased calcium levels (Huff, et al., J. Biol. Chem., Vol. 268, pp. 377–384 (1993); Rothnagel, et al., J. Invest. Dermatol., Vol. 101, pp. 506–513 (1993)). To define the sequences that are important for CaRE function, the factor binding sites within the 249 bp fragment were first identified. The CaRE bearing fragment was asymmetrically end-labeled and incubated with a keratinocyte nuclear extract in the presence of DNase I. Two protected regions were predominant. The 5' most footprint was designated as FP(A) and the adjacent footprint as FP(B). The protected region of FP(A) spans nucleotides +7895 to +7921 and contains within it an AP-1 consensus sequence, (TGATTCA) (Lee, et al., Nature, Vol. 325, pp. 368–372 (1987); Angel, et al., Cell, Vol. 49, pp. 729–739 (1987)).

An examination of the sequences protected in FP(B), which spans nucleotides +7924 to +7948, revealed an inverted palindromic sequence. This region contains two half-sites of the canonical hormone response element, (A/G) GGTCA (Evans, Science, Vol. 240, pp. 889–895 (1988)), separated by three nucleotides.

To confirm that binding to FP(A) is due to nuclear factor interaction with the AP-1 site, a 25 bp double-stranded oligonucleotide, containing the AP-1 consensus sequence, was added to the binding reaction. Binding to FP(A) was almost completely abolished by the addition of the competing oligonucleotide whereas that of FP(B) was unaffected. In contrast, the addition of 100 molar excess of a 25 bp nonspecific oligonucleotide had no effect on nuclear factor binding to either FP(A) or FP(B), whereas the addition of the unlabeled 249 bp CaRE fragment, inhibited protection of both regions. To test whether the protected region of FP(A) is due to the interactions of AP-1 transacting factors to this sequence, DNase I protection analysis was performed on the 249 bp fragment in the presence of purified c-Jun protein. As shown in FIG. 10, c-Jun binds to FP(A), although the boundary of the protected region is slightly different from that defined by the keratinocyte nuclear extract. Note that c-Jun did not interact with FP(B) nor with other potential cis-elements encoded by this fragment. The change in the footprinting pattern observed in the FP(B) region with the addition of c-Jun may be attributable to non-specific effects caused by the relatively high levels of c-Jun protein in this assay.

In mobility shift experiments on the CaRE encoding fragment three retarded complexes were consistently observed. Complex II disappeared upon the addition of 60-fold molar excess of an oligonucleotide containing the AP-1 consensus sequence, suggesting that this complex was formed by interaction of AP-1 factors to FP (A). Complexes I and III disappeared when an oligonucleotide encoding the thyroid hormone response element was used as the competitor, suggesting that proteins related to members of the thyroid receptor superfamily interact with cis-elements located within the FP(B) region.

These results were confirmed by repeating the gel shift assay on end-labeled fragments where the FP(A) and FP(B) regions were deleted individually from the original 249 bp CaRE encoding fragment. One complex (Complex II) was formed with a fragment lacking the FP(B) region (CaREAB) and was specifically competed by the AP-1 oligonucleotide but not by oligonucleotides encoding the thyroid response element, retinoic acid response element, or Vitamin $D_3$ response element. Two complexes (Complexes I and III) were observed with a CaRE deletion mutant lacking the FP(A) region (CaREΔA) and both complexes were removed upon the addition of oligonucleotides encoding hormone response elements.

The stability of these complexes were unaffected by the addition of the AP-1 oligonucleotide. Taken together, these data suggest that members of the AP-1 family of transacting factors interact with FP(A) and that members of the steroid hormone superfamily can potentially interact with the FP(B) site.

Calcium Induction is Mediated Through the FP(A) Site

To assess whether the sequences protected in FP(A) and FP(B) were functionally involved in mediating the calcium response, a reporter construct was employed consisting of the CaRE linked to a SV40 minimal promoter CAT construct. The CaRE.CAT construct has been shown to be activated by increasing concentrations of calcium in the medium (Rothnagel, et al., J. Invest. Dermatol., Vol. 101, pp. 506–513 (1993)). To test whether endogenous AP-1 factors were able to induce CAT activity from the CaRE.CAT construct we added 12-0-tetradecanoylphorbol-13-acetate (TPA) to transfected keratinocytes. TPA is a potent inducer of AP-1 factors in keratinocytes (Dotto, et al., EMBO J., Vol. 5, pp. 2853–2857 (1986)), and is able to activate CaRE.CAT in a dose dependent manner. Thus both calcium and TPA are able to induce CAT activity from the CaRE.CAT construct.

To determine the contribution of each protected region to CaRE activity the fragments lacking either FP(A) or FP(B) were linked to pA10CAT$_2$ and their ability to induce reporter gene activity in the presence of calcium was tested. Deletion of FP(B) did not affect calcium responsiveness while deletion of FP(A) completely abolished the calcium response. This observation suggests that all of the calcium response mediated by the CaRE can be attributed to factors interacting with the sequences protected in FP(A).

Vitamin D$_3$ and Retinoic Acid Modulate Calcium Induction of the HK1 CaRE

To determine the function of the FP(B) region, various steroid hormones, including thyroid hormone, retinoic acid, Vitamin D$_3$, and estrogen, were used to induce the activity of the 249 bp element in low calcium medium. These hormones by themselves were unable to induce CAT activity in a CaRE.CAT fusion construct. To determine whether these hormones were able to modulate calcium induction of the CaRE, transfected keratinocytes were treated with each hormone in the presence of high calcium medium (0.35 mM). Thyroid hormone, retinoic acid or estrogen had no effect on calcium induction but interestingly, Vitamin D$_3$ was found to suppress calcium induction. Since it has been observed that steroid hormone receptors are able to form heterodimers with other members of this superfamily (Glass, et al., Cell, Vol. 59, pp. 697–708 (1989)), it was asked whether the simultaneous addition of two hormones could influence CaRE activity in the presence of activating levels of calcium. To assess this, thyroid hormone, retinoic acid or estrogen were added along with Vitamin D$_3$ and calcium after transfection of the CaRE.CAT reporter construct. In combination, retinoic acid was able to reverse the suppression of calcium induction by Vitamin D$_3$. Thyroid hormone and estrogen had no effect on Vitamin D$_3$ suppression of the CaRE.CAT construct.

In order to show that hormonal modulation of CAT activity was specific to the CaRE, the effects of Vitamin D$_3$ alone or in conjunction with retinoic acid on the activity of another TPA responsive promoter (pHIVLTR.CAT) in transfected keratinocytes was tested. The HIVLTR promoter is also inducible by calcium but its activity was only marginally suppressed by Vitamin D$_3$, in contrast to the CaRE of HK1. Moreover, the co-addition of retinoic acid had no effect on the activity of this promoter. To determine whether the modulation of CaRE activity by Vitamin D$_3$ and retinoic acid was mediated through the interaction of receptors with the hormone response element of FP(B), the reporter construct lacking FP(B) was tested for Vitamin D$_3$ suppression of calcium induction. In comparison with the CaRE.CAT construct, the calcium response, of CaREΔB.CAT was less affected by Vitamin D$_3$ and interestingly, this suppression could be relieved by the co-addition of retinoic acid.

The above results are the first example of composite regulation of a keratin gene by AP-1/steroid receptor complexes. Interestingly, the HK1 promoter and immediate upstream sequences were unable to activate transcription of an HK1.CAT reporter fusion construct in the absence of the 3' CaRE. These results suggest that HK1 transcription requires elements both proximal and distal to the promoter and that the 3' CaRE element is functionally important for transcription of this gene. It is noteworthy that another keratin gene, HK14, was also found to require both proximal and distal elements for efficient transcription (Leask, et al., Genes Develop., Vol. 4, pp. 1985–1998 (1990)).

The proximal footprint, FP(A), encompasses sequences between +7895 and +7921 with respect to the start of HK1 transcription and is responsible for mediating the calcium activation of both homologous and heterologous promoters. This region encodes an AP-1 site and it was inferred from the footprint and gel shift assays that AP-1 factors bind to this region to confer the calcium response. A second potential AP-1 site within the 249 bp fragment was identified by sequence homology comparison in the earlier study by Huff, et al. (Huff, et al., J. Biol. Chem., Vol. 268, pp. 377–384 (1993)), but appears to be non-functional in keratinocytes. This site was not protected in footprinting assays by proteins from keratinocyte nuclear extracts nor by purified c-Jun. Moreover, the CaREΔA construct which lacks the first AP-1 site within FP(A) but retains the second potential AP-1 site, was unable to induce CAT expression. The two AP-1 sites differ only in two positions, one of which occurs at a position relatively insensitive to substitutions (Risse, et al., EMBO J., Vol. 8, pp. 3825–2832 (1989)). These results imply that AP-1 factors in keratinocytes can discriminate between these two sites and it is possible that sequences neighboring the AP-1 site within FP(A) also contribute to nuclear factor binding to this region (Ryseck and Rodrigo, Oncogene, Vol. 6, pp. 533–542 (1991)).

AP-1 sites have been identified in keratins K8 and K18 (Tamai, et al., Gene, Vol. 104, pp. 169–176 (1991); Oshima, et al., Genes Develop., Vol. 4, pp. 835–848 (1990)), as well as in the promoter regions of the keratinocyte-specific, human papilloma viruses types 16 and 18 (Cripe, et al., The New Biologist, Vol. 2, pp. 450–463 (1990); Offord and Beard, J. Virol., Vol. 64, pp. 4792–4798 (1990); Mack and Laimins, Proc. Natl. Acad. Sci. USA, Vol. 88, pp. 9102–9106 (1991); Thierry, et al., J. Virol., Vol. 66, pp. 3740–3748 (1992)). An AP-1 site in the first intron of human K18 has been shown to be activated by co-expression of Fos and Jun (Oshima, et al., Genes Develop., Vol. 4, pp. 835–848 (1990)). Similarly, Fos and Jun have been shown to bind to the AP-1 sites within the long control region of human papilloma viruses where it is suggested that AP-1 sites are necessary but not sufficient for transcription. However, none of the above sites have been reported to be involved in calcium induction of these genes. In this respect the AP-1 site identified in the HK1 CaRE appears to be unique.

The expression of HK1 mRNA is tightly regulated and restricted to the spinous layer of the epidermis which can be considered as an intermediate state between the loss of proliferative potential and cell death. Since calcium can inhibit proliferation of keratinocytes and promote their differentiation and Vitamin D$_3$ can induce cornification of cells already undergoing differentiation, we propose that calcium promotes HK1 gene transcription through the upregulation of AP-1 factors and their subsequent binding to the FP(A) site, concomitant with or soon after the cell enters the differentiation pathway. HK1 transcription would then be maximal in the mature spinous layer cell where retinoic acid levels are high enough to antagonize the action of vitamin $D_3$ keeping the FP(A) site responsive to calcium activation. Later, as the keratinocyte differentiates into a granular layer cell, where Vitamin $D_3$ levels are maximal and retinoic acid levels are at their lowest, the activity of the FP(A) site would be suppressed and HK1 transcription down regulated. Thus the interaction of these modulators with the CaRE can account for the restricted expression of HK1 observed in vivo.

In summary, we have demonstrated the interaction of AP-1 factors with FP(A) and that of Vitamin $D_3$ and retinoic acid through their receptors with FP(B). The complex interplay between each of these factors serves to restrict expression of HK1 to the spinous cell during epidermal differentiation. We conclude therefore that the CaRE of HK1 functions as a differentiation stage-specific enhancer.

All patents and publications mentioned in this specification are indicative of the levels of those skilled in the art to which the invention pertains. All patents and publications which are incorporated herein by reference are incorporated to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The bioreactors, nucleic acid sequences, transformed epidermal cells, transgenic animals and human keratin K1 vector, along with the methods, procedures, treatments, molecules of specific compounds, are exemplary and are not intended as limitations on the scope of the invention. Changes therein and other uses will occur to those skilled in the art which are encompassed within the spirit of the invention as defined by the scope of the claims.

We claim:

1. A method of treating skin cancer in a mammal comprising administering a K-1 keratin expression vector at or directly around the site of a skin cancer cell, wherein said vector comprises in operable association:

a nucleic acid sequence encoding a functional p53 protein;

a 5' flanking region from a mammalian gene including necessary sequences for expression of said nucleic acid sequence;

a 3' flanking region from a mammalian K1 keratin gene which regulates expression predominantly in epidermal tissue; and a linker connecting said 5' flanking region to said nucleic acid sequence, said linker having a position in which said nucleic acid sequence is inserted, wherein expression of said p53 protein by said skin cancer cell results in inhibition of the cell's proliferation.

2. The method of claim 1, wherein said 5' flanking region includes a promoter, a 5' UTR and a first intron and intron/exon boundary in appropriate relationship for expression of said nucleic acid cassette.

3. The method of claim 1, wherein said 3' flanking region includes a 3' UTR and a 3' NCR containing the transcriptional termination region.

4. The method of claim 2, wherein said 5' flanking region is approximately 1.2 kb, said first intron/exon boundary is 1.0 kb, and said 3' flanking region is approximately 3.9 kb of said mammalian keratin K1 gene.

5. The method of claim 2, wherein said 5' flanking region is approximately 1.2 kb, said first intron and intron/exon boundary is 1.0 kb, and said 3' flanking region is approximately 4.3 kb of said mammalian keratin in K1 gene.

6. The method of claim 1, wherein said vector further comprises a modulator sequence in either the 5' flanking region or the 3' flanking region.

7. The method of claim 6, wherein said modulator sequence comprises sequences responsive to calcium, Vitamin D or its metabolite, Vitamin A or its metabolite, or progesterone.

8. The method of claim 6, wherein said 3' flanking region further includes an 18 KB EcoRV fragment from said mammalian keratin K1 gene.

9. The method of claim 2, wherein said 5' flanking region comprises nucleotides 1 to 1246 of Sequence ID No. 1;

said 3' flanking region comprises nucleotides 6891 to 10747 of Sequence ID No. 1; and said linker comprises nucleotides 2351 to 2376 of Sequence ID No. 2.

10. The method of claim 2, wherein said 5' flanking region comprises nucleotides 1 to 46 of Sequence ID No. 1;

said 3' flanking region comprises nucleotides 7895 to 7921 of Sequence ID No. 1; and said linker comprises nucleotides 2351 to 2376 of Sequence ID No. 2.

11. The method of claim 2, wherein said 5' flanking region comprises nucleotides 1 to 46 of Sequence ID No. 1;

said 3' flanking region comprises nucleotides 7924 to 7948 of Sequence ID No. 1; and said linker comprises nucleotides 2351 to 2376 of Sequence ID No. 2.

12. The method of claim 1 wherein said skin cancer cell is a squamous epithelial cell.

13. The method of claim 12, wherein said squamous epithelial cells are selected from a group consisting of epidermis, oral mucosa, esophageal, vaginal, tracheal or corneal epithelia.

14. The method of claim 12, wherein said 5' flanking region includes a promoter, 5' UTR, and a first intron and intron/exon boundary in appropriate relationship for expression of said nucleic acid sequence.

15. The method of claim 12, wherein said 3' flanking region includes a 3' UTR and a 3' NCR containing a transcriptional termination region.

16. The method of claim 14, wherein said 5' flanking region is approximately 1.2 kb, said first intron and intron/exon boundary is 1.0 kb, and said 3' flanking region is approximately 3.9 kb of a keratin K1 gene.

17. The method of claim 14, wherein said 5' flanking region is approximately 1.2 kb, said first intron and intron/exon boundary is 1.0 kb, and said 3' flanking region is approximately 4.3 kb of a keratin K1 gene.

18. The method of claim 14, wherein said 5' flanking region comprises nucleotides 1 to 46 of Sequence ID No. 1;

said 3' flanking region comprises nucleotides 6891 to 10747 of Sequence ID No. 1; and said linker comprises nucleotides 2351 to 2376 of Sequence ID No. 2.

19. The method of claim 14, wherein said 5' flanking region comprises nucleotides 1 to 46 of Sequence ID No. 1;

said 3' flanking region comprises nucleotides 7895 to 7921 of Sequence ID No. 1; and said linker comprises nucleotides 2351 to 2376 of Sequence ID No. 2.

20. The method of claim 12, wherein said 5' flanking region comprises nucleotides 1 to 46 of Sequence ID No. 1;

said 3' flanking region comprises nucleotides 7924 to 7948 of Sequence ID No. 1; and said linker comprises nucleotides 2351 to 2376 of Sequence ID No. 2.

21. The method of claim 12, wherein said vector further comprises a modulator sequence associated with said 3' flanking region or said 5' flanking region.

22. The method of claim 21, wherein said modulator sequence comprises sequences responsive to calcium, Vitamin D or its metabolite, Vitamin A or its metabolite, or progesterone.

23. The method of any of claims 2–11 wherein said skin cancer cell is an epidermal cell.

* * * * *

```
                              SEQUENCE LISTING (1) GENERAL INFORMATION:

(iii) NUMBER OF SEQUENCES:           5

(2) INFORMATION FOR SEQ ID NO:  1:

(i) SEQUENCE CHARACTERISTICS:
              (A) LENGTH:              10747 base pairs
              (B) TYPE:                nucleic acid
              (C) STRANDEDNESS:        single
              (D) TOPOLOGY:            linear (ii) MOLECULE TYPE:            DNA (genomic)

(xi) SEQUENCE DESCRIPTION:  SEQ ID NO:  1:

GAATTCGGCT GCTGTGCTGT CGTACAACAT GCTGTTTAGG ATCTTGCACA TGATAGCTAG      60

GTATTCTTGC TTCAAATCGC AGGCACCCCA CTTACCAACT GTGTAGACTT GATCACGTTA     120

TTCAACCCCT GTGTCTCTGC TTCCTCATTT TACAAATGGG GAGAAAAATA GCATCTATCT     180

CAAAGTTGTG AAAATTAAGC AAGTTAATAC ATATGTGCTA CGTAGAACAG TGCCTGGTAC     240

ATGGTCAGTT TTTGATACAT GTTAGGTATT ATCATTATTA TCACCTCCAG AAACAATTTA     300

AACTTCTCAT ATAAGGCTCT CCAGACACCT CTCATTGTCT TCCCTTCCAA ATCTGCATTT     360

ATCTCTCTCT CTTTGCAGTC CAGTGTGAGG CTTGAATCAC CTATCAAGCC TCACCTCCAC     420

CCCTGTGCTT TACAAAATGT CCTAGAGCTT CTATTTACTC GTCTCACTGC TCTGTGGGCT     480

TTTTCACTCA AGGGCGTTTG CATGCTATCC ATTGCTACCT GTTTTCTGTT GCTGGTGTCT     540

GTCTCCTGCT CTATCTTTGA AGAAAAGAAA CAAGAAAAGG AATAACTGAG AAACAGAGAA     600

AAAAAATGTC TCTCCCTTCT GGTTCTTCCA GACCACCCAC TCATCCATCT TGTTCAATGA     660

CAGCTTCTCT TCCTTTAATT AATCACTGTG GTATATTTAT AAAGCTTATA TTTATGAAAG     720

ACCTTTTAAT TTTTTAGTTA TTAAAGCCCT TTCTCTTTGT CAGGTTGTAA CTGAGTGAGC     780

TCTGGAGTTT GGAAAGAAGA TCTTAGAAAT GGGCCAGAGA GCTCCTTCTG AGATCCAAGC     840

ACGGAGAATT GCACCTGCTG TGCATGGTAA GAGAGTGTGC TTGGTAGCTC ACAAGGGCAA     900

GGTGAGAATA GAAACTTTCA TGCCTTTTTG ATGGGGGTTA TGAAATCCTA CCAAGAAACA     960

CCAGGTATCA GATGTGGGGT CCTGTTTTCC CAAAGCCACA AATGCTTGAA GGAAGATCTT    1020

GTGTGATAAA ATAATTACCA CATGAACCAA TCTTGCATGC ACAGCAATTT TGAGAGCCCA    1080
```

```
TCCTGGGAGC TAGGTGTGTA GTGTTTATCG TATTGTTGAG GCTCGTAAAA ATCTTGTATG    1140

GCTGCAGGCA AGCCAAACCC TTGACAGGCA CTGCATCTCC GCTGACTCTA GAAGACCAAG    1200

CCCAATTTCT TCCCTGTATA TAAGGGGAAG TCTCTATGCT TGGGGTAGAG GAGTGTTTAG    1260

CTCCTTCCCT TACTCTACCT TGCTCCTACT TTTCTCTAAG TCAACATGAG TCGACAGTTT    1320

AGTTCCAGGT CTGGGTACCG AAGTGGAGGG GGCTTCAGCT CTGGCTCTGC TGGGATCATC    1380

AACTACCAGC GCAGGACCAC CAGCAGCTCC ACACGCCGCA GTGGAGGAGG TGGTGGGAGA    1440

TTTTCAAGCT GTGGTGGTGG TGGTGGTAGC TTTGGTGCTG GTGGTGGATT TGGAAGTCGG    1500

AGTCTTGTTA ACCTTGGTGG CAGTAAAAGC ATCTCCATAA GTGTGGCTAG AGGAGGTGGA    1560

CGTGGTAGTG GCTTTGGTGG TGGTTATGGT GGTGGTGGCT TTGGTGGTGG TGGCTTTGGT    1620

GGTGGTGGCT TTGGTGGAGG TGGCATTGGG GGTGGTGGCT TTGGTGGTTT TGGCAGTGGT    1680

GGTGGTGGTT TTGGTGGAGG TGGCTTTGGG GGTGGTGGAT ATGGGGGTGG TTATGGTCCT    1740

GTCTGCCCTC CTGGTGGCAT ACAAGAAGTC ACTATCAACC AGAGCCTTCT TCAGCCCCTC    1800

AATGTGGAGA TTGACCCTGA GATCCAAAAG GTGAAGTCTC GAGAAAGGGA GCAAATCAAG    1860

TCACTCAACA ACCAATTTGC CTCCTTCATT GACAAGGTGA GTTTCTCTCT CATTGCACTG    1920

GTAGGGCTGC CGCTGGTCCA CTTGGGATTG GTGCAGTCAA AACACATGTA GGTTTGAACC    1980

TCAAGTTTCC ATGTTTACAT GATTAAAAGG ATGTTTTGTG GAATGGTCTC CTAGGAGATA    2040

TGTTAGATGT ATGCTTGTGA ATGGTGTTAA TGACTCTCTC TTTGACAAAG GGTTCGTGGT    2100

CGACCTAAAG GTGGGTCAGT GTGACATTAA CATTTAAGTG CTTTTTATTC AGCTCTTGAG    2160

CGGAATTGGG ACTCATATCT GTTGAATGAA GATAATAGAA ATGGGGCTAA CTGAACTTTC    2220

CAGGGTGCAA GTGAGAACCC TGGAAAGGTC TTCCTAACCA TAGAAAGGGA GTTGAGTGTG    2280

AACATAGTAT AGAGTGTTAT TGTAGCAGAA AACATGTGGT CAGTCAGTGC CAAACATCTT    2340

TTGCTGTCAG AGGGGAGCTC TGCCTTCTAA TAATTTTACA TTGGTACTGG ATGAGGCTAG    2400

AGTTTTTTTA TACTAATATC TCCAAAAATC AGCTCTAAAA AACTCAGATA AACCATTTTT    2460

TTAATTTTTT GCTTAATCAT TAATAGTGCC AATCCAAGGT TATCCACAAC AAATTTCAAA    2520

TCCAATTTTG AATTTTCCTG ATATACTTTT GAAATGTGTG TGTGTCCTGG GGATGCAAAC    2580

CAGTTTTTAT GGTAATATAC CTAACAAAAT TTTGGAAGGC AAATCTCTTA AATACCATGC    2640

ACCTATTTCA AAACATAATT GCAATAATTC TGTATGCGCT TTGCTATTGG TATTTGTTTA    2700

GTTACTCCCT TCCAAGCCCT CTCTGAATTA ACAAGTTGGG TTTTATTATG CAGATGATAT    2760

TAACTTGATC ATCTTCTTCC TATTTCTCTG TCATGGTCAG AAGATAGGAA TTGAGGTTCT    2820

TTTCCAAATG AGGCACAGTT CTCCATGGCT ATGAGACTCC ATTTATGCAT CAGGAGTAAA    2880

GGGGTCTTGT GTTTTTAGGT GAGGTTCCTG GAGCAGCAGA ACCAGGTACT GCAAACAAAA    2940

TGGGAGCTGC TGCAGCAGGT AGATACCTCC ACTAGAACCC ATAATTTAGA GCCCTACTTT    3000

GAGTCATTCA TCAACAATCT CCGAAGGAGA GTGGACCAAC TGAAGAGTGA TCAATCTCGG    3060

TTGGATTCGG AACTGAAGAA CATGCAGGAC ATGGTGGAGG ATTACCGGAA CAAGTAAGGG    3120

ACCCTGTCTG GGCAGTTCTT AACTTTTGCT GTAAAAGAGT TCCAGAAAGT AATAAGCTAA    3180

GATCATGAAG CAGCATGTAG CTATGTCTTT TCTTAGGTTA GAGGCACATC AGTTTGACAT    3240

TTTCAGAAAT CTTCATTTTC TCAGGAGATG GAAATAGTCT AGTGGTTTTA TTGCTCAGTA    3300

GAAAGTAGTG GCCAATATGT CCTAGGTTCA TAATAGAAAG GCAGTGATAG GCAATGCCAC    3360

CTTTAGTTTA GAATGCTGGA CTTCAGGTCT TACCACCTCT GAATCTCCTA ATTGTTTCTG    3420
```

```
CTTTCCTGCA GGTATGAGGA TGAAATCAAC AAGCGGACAA ATGCAGAGAA TGAATTTGTG   3480

ACCATCAAGA AGGTAAGCAA ATTCTGTAGG ACGGAACTCA CATTTGAAAT AAATAAGGGA   3540

AGAGGGTCTC CAATTACTAA GCAGAAAGCA GCCATGATAT GGAGAGCCAG GTAGTAGACC   3600

TGGGGAGTAT ATGGAGTGGG GCTATATTTT TCACATCATC ATGGACCTGG ACTGATCCAG   3660

GCACTTGGCT TCTCCATATT TCCCAGCACC TTACATAGTA AGTGGAGTGG CAGATTCTCA   3720

GCAAGCCAGG CACACTCCCT TGATGGTGCT ATCCGGGGGT GGGACAGTTA GGGAACTGTG   3780

ATTTACCTGG GGCAAAAAGG AGTGGAGTAG ACCCAAAGCT CCTTTTTTTG CTTGGAGAAT   3840

CCCCTCACAG GTAATGAGAG GGACCTGCCC TGGAGAGAAC GTGCCTTCAT GATGTCCCTT   3900

GTTCCTCTAG GATGTGGATG GTGCTTATAT GACCAAGGTG GACCTTCAGG CCAAACTTGA   3960

CAACTTGCAG CAGGAAATTG ATTTCCTTAC AGCACTCTAC CAAGCAGTAA GTCTTCCAGT   4020

TTCAACCAAG TTTATCTAAA TGGAGAGTTT TTAAGCCGGA ACCCACAACG ATTCAGAAGA   4080

ATAGATATTT ATCTTTTATT TCCTGACTGC TTTCTCTGTC TAAGTTGTTT TTTGTTTTAG   4140

TGCTGTAAGA GTCACTAACC TATTATGTCT TGCAGGAGTT GTCTCAGATG CAGACTCAAA   4200

TCAGTGAAAC TAATGTCATC CTCTCTATGG ACAACAACCG CAGTCTCGAC CTGGACAGCA   4260

TCATTGCTGA GGTCAAGGCC CAGTACGAGG ATATAGCCCA GAAGAGCAAA GCTGAGGCCG   4320

AGTCCTTGTA CCAGAGCAAG GTGAGTGGGC TGAAACCGTA GCCAGTTTCC CTGAAATGGC   4380

TTGTCTTGCT ATCCTGTGTT ATCTCATGTA TGTGTGCCTG TGCCATGCTG AGTTCTGCCT   4440

ACATTTAACA AACGCTATCT ACCATCTTTA GTATGAAGAG CTGCAGATCA CTGCTGGCAG   4500

ACATGGGGAT AGTGTGAGAA ATTCAAAGAT AGAAATTTCT GAGCTGAATC GTGTGATCCA   4560

GAGACTTAGA TCTGAAATCG ACAATGTCAA GAAGCAGGTA TGTGCTTTCT CCTTCTACCA   4620

CTCAGCTGTA TGGAATGGGG GTAACCCTCA GGTAAAGGGC GAGTGCTTTC CTAGTTTTGA   4680

ATCTTGCAAT TCAGCCCAAG GCTACATTAT TAGCCCTGGT TCCTTTTCTG ACTATGCTAG   4740

TTTCCAGAAT GCAGCCATCA TGCTGGGTTC TCTTTAGGGA AATCTGTGAG AATGGCCTAG   4800

TAGAGAAAGA TGGGATGGTC AATGTGAGTG ATCTAGCCTA TGACCCAAAG TGGACTTAAG   4860

AGTTGGGGAG TGAGAGGAAG GGCAGCCAGG AGGTTTTAGA GTAGGTGTTT AGAAGAATGT   4920

CAAGTCTGTA AGGGTTGTAG GAGCCTTGAC TCAGGGCCAA GAGAGGCTGT TGAGTTATCC   4980

CTAAGGTCTT TTAAGGAAGT CAACATGGTG ATGTGTTATC TGGAGGTGGG TGTGAGATGA   5040

CTTAAGGCCA AGTGGTTCTG TTGGACTCAT TATTGGCCTC ACTGGAGTGG GGAGACCAAT   5100

TGGGATGAGG AGGCCTAGTG GGGAATGCAT ATTATGAGAG GGTGTCATAT CTTTTTCAGA   5160

TCTCCAACTT GCAGCAGTCC ATCAGTGATG CAGAGCAGCG TGGCGAGAAT GCCCTCAAGG   5220

ATGCCAAGAA CAAGCTGAAT GACCTGGAGG ATGCCCTGCA GCAGGCCAAG GAAGACCTGG   5280

CCCGCCTGCT GCGTGACTAC CAGGAGCTGA TGAACACCAA GCTGGCCCTG GATCTGGAGA   5340

TTGCCACCTA CAGGACCCTC CTGGAGGGAG AAGAAAGCAG GTGAGGAAGG GACGCTGGGA   5400

GTCGAACCTC TTCTCATGGT CTTCCTTCCT TGCAAGCTGA TTGTTGTTGA AGATGCAGCC   5460

ATCTGATTGC AGCTTGTGCT GGGTATGGGG AAATGAAAAG TACACGGAGC AGGAGGAAGG   5520

ACCTAGTTTT ACTTTGGGAG CTGGAGTCCC AAGCTGTTTA TTTTTTTCTT CTAGGGCTGT   5580

AACATATCTA GAAAGAGCTT TGAGGTGGAG CAAATTATTC TTTATCTGGG CTGCCTCAGA   5640

TGGCAGCTGG CCTAAAGTCG GCATCTTTAG AGGGGGCCTT CATTGGCTGC AAGGCTCGTC   5700

TCGTTTATAT GGGAATTTCT CCGTGTTTGT ACTCTTGCTG AGAAAAAATG ACAGGTCTGG   5760

GAGGCCAGAG GGGATTGGAT TAAGTTTCAG ATTAAGTGCA TTGGAGAAGA CCCAGATGGG   5820
```

-continued

```
GAAAGTCTTC AAGGTGGTGG AGCGGGGAAT GGGGAAGCGG TTTGGGAAGC TGGAGTGTCC    5880

TGAGGAATTT TCTTATTTTC TCCTACAGGA TGTCTGGAGA ATGTGCCCCG AACGTGAGTG    5940

TGTGTAAGTA CAAGTCGATT TCTCAGGGGC ATGTGCAGGC TTTGTTGGGC TGGAAACGGA    6000

GTTGAGGTTG AAAATAACTG AGCTTCCTCT TGCAGCTGTG AGCACAAGCC ACACCACCAT    6060

CAGTGGAGGT GGCAGCCGAG GAGGTGGCGG CGGTGGCTAC GGCTCTGGAG GTAGCAGCTA    6120

TGGCTCCGGA GGTGGTAGCT ATGGTTCTGG AGGTGGCGGC GGCGGCGGCC GTGGCAGCTA    6180

TGGCTCCGGA GGTGGCAGCT ATGGCTCTGG AGGTGGCGGC GGCGGCCATG GCAGCTACGG    6240

CTCCGGAAGC AGCAGTGGGG GCTACAGAGG TGGCTCTGGA GGCGGCGGCG GCGGCAGCTC    6300

TGGCGGCCGG GGCTCTGGCG GCGGGAGCTC TGGAGGCTCC ATAGGAGGCC GGGGATCCAG    6360

CTCTGGGGGT GTCAAGTCCT CTGGTGGCAG TTCCAGCGTG AAGTTTGTTT CTACCACTTA    6420

TTCCGGAGTA ACCAGATAAA GAGATGCCCT CTGTTTCATT AGCTCTAGTT CTCCCCCAGC    6480

ATCACTAACA AATATGCTTG GCAAGACCGA GGTCGATTTG TCCCAGCCTT ACCGGAGAAA    6540

AGAGCTATGG TTAGTTACAC TAGCTCATCC TATTCCCCCA GCTCTTTCTT TTCTGCTGTT    6600

TCCCAATGAA GTTTTCAGAT CAGTGGCAAT CTCAGTCCCC TGGCTATGAC CCTGCTTTGT    6660

TCTTTCCCTG AGAAACAGTT CAGCAGTGAC CACCACCCAC ATGACATTTC AAAGCACCTC    6720

CTTAAGCCAG CCAGAGTAGG ACCAGTTAGA CCCAGGGTGT GGACAGCTCC TTAGCATCTT    6780

ATCTCTGTGC TGTTTTGGTT TTGTACATAA GGTGTAAGCA AGTTGTTTTT CTTTTGTGGA    6840

GAGGTCTTAA ACTCCCCATT TCCTTGTTTT GCTGCAATAA ACTGCATTTG AAATTCTCCA    6900

TGTCTCGATC GCCCTTGTTT ACGGCACTGT CTAACCTGGA TGGGTGTTTT GTGAGGTAAA    6960

AGAAGACACT AGAGCCACAT GGCATATGGG AAAGTCATGC ACACAAACAT GAGAAAAATG    7020

CAGAGGCCAA CCAGGCAACA TTTCACCAGA CTGGAATCAC AGAGAGAGCA AGCACTTTCC    7080

CAGATGGTGG GGATGTCATG GAGAAATGGA GAGACCGGGT GACAGGTTTT GTTCATTTGA    7140

GAAGGCTTTC TTGAAAAGGG CAGTGAGCAA GCAGGTTGGG AGGAAGAGGT GTGGCATTGA    7200

GAAGAAGGGA AAGTATTGCA TGAAAAAGTA ATTCTTCACG TGGAACAGCC AGTAAGGAGG    7260

GGCATGAGTA ATATAGGGTC AGCAGTTACT GGAGCCAGAA TACAGACTTT GGCCTGGGGA    7320

GTTCAAGAAC TAAGAGTGGT AATAGAGAGT TGGATATTCC ATTTCCCTTC TCTTTTTGTG    7380

CCACCACCCA AAGCTCTGCA TAATCTAAGA AGTTCCCTTG TTGACACATA GCTCATACTT    7440

GTGAAGTTGT ACAACAGGAT AGCATAGTGG CCAGAAGCAT GGACAGTTGA ACTCAGATAT    7500

GCTTGGGTTT GAATCTTACC ATCACCATTT ACTAGTTCTG TAATACAGTG CAAGTTACAG    7560

ACATCTCTGC ACCTCAGTTT TAGTATGTCT AAATTGGGGA TGATAATGCC TTCCTTGTGG    7620

GGATAGTGTG AGGATTGAAT AAGATGAATA CACATGGCTG AGCACACAGC AAGCACTAAA    7680

TAAGTGCCAG TTTTAATGAT AACGGTGATG ATGATGATGA TGATGATGAT GACGTAACAT    7740

TGCTTGTGGG ACTCCATACA GCTCAGTAGA TGCTTGCTCA AAGAAGCAAG TTACCAAAAT    7800

TTTTGTAATG GTTCTATGAA CGTGAAAAAA GCAGTCAACT TCTCTGAGGA TCAATTTCCT    7860

TAGTTTCCAA TTAGGAAAAG TCTTCTTAGC TCCAGAGTCC CACAGGGCTA ATGGAATAAG    7920

GAGAGGATAG ATCACACATG TATTATGCAA ACACAACTCA GGTGAGCTCT ATTCTTCCTT    7980

CTCAGTTATC CCTTCTGTAG GGACCCCAGT GTCCCTGCT GTCTTTCTGT GTCCTGACCG    8040

GGAAACACAG TGTGCCTTGT CTACTCCATC ACTTGGCCAG CTGCATGCTT TCCTTTGCAG    8100

GCTTGAAGCA AAGCTGGGTC TCGGACATTC TCAGGCACTG ACAAAGCTGT TTAGTTGTTG    8160
```

-continued

```
CTGGGAAACA CTGGGAAATA GCCCTTTTGT TAAACACACA GAAACTAGCC TTCGCCCTGA    8220

GCCAAATTCC TTAAACTCGT CTATGAAATT CCATAACCTG ACTCCTTAAC TGCAGACATA    8280

CCCAGCTAGA ACATCCCTCA TGTCCCTGTC CACCGTGAGA ATGCTGCACT TCACTCTGAA    8340

CCTTTAGTCC TCCTTTTAAA TACTGCACAC TGATCACCCT GGTGTTAGT GCTTTGTTTT     8400

TTGGAATCCC ACCTGGCTCC ATTTTGGGAT GGTTCCGGGC ACTTCCCTAT GGAAATTCCC    8460

CTGCTGTCAC TGTCAGAGTG AGTCCAGCAG TGGGTTTAGC TGGATGAAAC ACCACCATGT    8520

CCATTTCCAT TCAGACTAAT GTCAGAATTT GAAAGGCACT ATGGTAGAGT AGAAAGAACA    8580

AGGAACTGTA CTATTTAAAG GGCAGGCAAA GAAAAGGCAT CTATAGCTTA TAAGATGTGT    8640

GGATCTTTGG ATGTGACTTG GCCATCCTGA GCCTAAGTTG TCTTGTAGGA GAAATGGGAA    8700

TGAGAATATT TTCCTCTAGA CATCAAGAGG AAAAGAAATA TAACGTGAAA ACCTTTGTGA    8760

ATTGTGAATG TGTTATACAG AGTAGCTAAA AGAATTAAAA AGGGAGTGAC AAAAAAGTAA    8820

AAGGCAGCTG GCTGCTCAGG GCCTCCATGG AGGGAAGTAC CTTGATATGG TCACTGTGGC    8880

TCAGTGACAG CTCTGCAGGG ACAGGAAATT GATTTGTTAG TGCACCCAAA GTTGAATCTG    8940

CTCCTGAGTA CTGATTTATG GGAACCAAAC ACACAAGAGA TGAAGGATGT GTCAACCAGA    9000

ATGTCCAGCA TTAGCTTGTG GGGAAACACA TACTTCCAGT GACTGAAATA CCATCCTGTT    9060

ATCAAGAGAT CTGGGAAACT AAAGTACTGA CAAGAGCTGG CTTGATCTGT GGATTTAGAA    9120

CAATGAGAGT TAGGTGGCCT TGAGGGAGAT GATTCACTCT CCTTCACAGA AGAGCTGACC    9180

TCTGGGGTCA ACAGATATAG CACCTCTTTC CCAGGGACGC TACTGAATGA ACAGTGATGT    9240

GTTCTTATAC TCTGGCCCAG ATTTTCTACA TACTTTCTTA GGTTACAACT TTATTTAGTC    9300

ACATTTCAGT ACTGGGGATA CTCCTGTTTA TCTTCTTTGG ACTCGAGTTT TTATGGGAAG    9360

GTCATGAAAC AGAGAAAAAT ACAATTTGCA GGGAAACTTA CCAAGGCTTG TAAGGTTACA    9420

AGGATTAAAT GAAAACCCTG TGTAAGTCAG TATATAGTGA AGAAGTAAAT TGAGTTAGAC    9480

CAAACGCCAA AATGCATCCG CATTAGAAAG ACGATAAAGG AAGACTCTGG ATTCAGTTCT    9540

GTTCAAAAAA CATTTTCTGC ACAAATACTA TGTATGAGGA ACTGGGCGTT GGGGAGATGA    9600

TGATGAGTGA GACATGGTTC TTGCTTTCAG AGAGCCTAGA GACCTGGGTG GTAGCAATGG    9660

TAGAGATACA TCCAAGACAC AGAAATAGAT ATACAGGAAC ACAGATGATT GAAAGTGATG    9720

CTTGGCAGGG CTTTAAAGAA TGAATCAGAG TTTTTCAGGC AGACGAGGAT CTTCAAGGCA    9780

GAGGGAATCA TATAGATAAG GACATAGAAG AGTGAAATTT CATGAAGTAG TTAAGCATCT    9840

GAAGAAGCAT GGAATTAGTG ACAAGAAATG ATGCGGAAAA GATATCCAGA TCCAATCAAG    9900

AAGGGCCTTG TTGGCATTCT ATGGAGTCTG GACTTTGGCT TCTGGGTCAC AAGTTCTCAG    9960

ATGGGGTTTT CATATCTATT ATTAGACCTA CTATGTACTG GTCCAGTGGA AGGGAAAGGG   10020

GTTGTCTTAC TGCTAGTGGA GTAGGAATTG GGTATGGACC ACAGCTTGTC TTGTTTCCAA   10080

GTATTCCCTA AGAAATCTGG TCTGCTGATG GGAGATCTAT TTATGGAAAT GTCTTTTTCC   10140

CTCAGGAATT TTATGTCGGA AACAGCTGTC ATAGGTGAGG AGGAACTGGT AAAAGTACTT   10200

AATAGGAGAG TGTCATGGTC AGATTGGTGT TTTGGAAAAG TCAGCCAGGG CAGATTGGAG   10260

AGGTCCATAT TGGAGGCAGG AAGACTTAAG AGACTATTGC AAAGGTGAAG ACAAAAGACG   10320

ATAGGGACTT GCACTTTAAT TCCAGCCCTT AGAAGTAGTA GAAGGTCAGA AATGAGAATA   10380

TGCATTACAG AGATAGTTAG TTGCTATATC ATTAGGACTT GGTGATAGAT TGGATGAGGA   10440

TGCGGTTGGG TGAGGCAAAG AGGAGAGTCC ACATTCCTGG TCTGGGTAGT AACAAAGAAT   10500

CTAGCAAGAG GGCTTGTGGG GAAAGATGCT GAGTTACGTA GCAAGTGCAT CTGCTTTATC   10560
```

CTTGTAATGA ATGGGGCTAA AGGTGTAAAC CAAAGAGTCA TCAGCATTTG GAGGGTAGAA     10620

TAAATCATCA GATAACTCAG GAAGAAGGAG CAGAAGAATT ACTGATACTC CCTGGAAGGA     10680

AAACCGGAAG TAAATGGGAG AAACTTGCTC AAGTGGACAA AGTTTAACAG ACATGAAGCA     10740

TGAATTC                                                              10747

(2) INFORMATION FOR SEQ ID NO: 2:

(i) SEQUENCE CHARACTERISTICS:
           (A) LENGTH:          6693 base pairs
           (B) TYPE:            nucleic acid
           (C) STRANDEDNESS:    single
           (D) TOPOLOGY:        linear (ii) MOLECULE TYPE:       DNA (genomic)

(xi) SEQUENCE DESCRIPTION: SEQ ID NO: 2:

GAATTCGGCT GCTGTGCTGT CGTACAACAT GCTGTTTAGG ATCTTGCACA TGATAGCTAG       60

GTATTCTTGC TTCAAATCGC AGGCACCCCA CTTACCAACT GTGTAGACTT GATCACGTTA      120

TTCAACCCCT GTGTCTCTGC TTCCTCATTT TACAAATGGG GAGAAAAATA GCATCTATCT      180

CAAAGTTGTG AAAATTAAGC AAGTTAATAC ATATGTGCTA CGTAGAACAG TGCCTGGTAC      240

ATGGTCAGTT TTTGATACAT GTTAGGTATT ATCATTATTA TCACCTCCAG AAACAATTTA      300

AACTTCTCAT ATAAGGCTCT CCAGACACCT CTCATTGTCT TCCCTTCCAA ATCTGCATTT      360

ATCTCTCTCT CTTTGCAGTC CAGTGTGAGG CTTGAATCAC CTATCAAGCC TCACCTCCAC      420

CCCTGTGCTT TACAAAATGT CCTAGAGCTT CTATTTACTC GTCTCACTGC TCTGTGGGCT      480

TTTTCACTCA AGGGCGTTTG CATGCTATCC ATTGCTACCT GTTTTCTGTT GCTGGTGTCT      540

GTCTCCTGCT CTATCTTTGA AGAAAAGAAA CAAGAAAAGG AATAACTGAG AAACAGAGAA      600

AAAAAATGTC TCTCCCTTCT GGTTCTTCCA GACCACCCAC TCATCCATCT TGTTCAATGA      660

CAGCTTCTCT TCCTTTAATT AATCACTGTG GTATATTTAT AAAGCTTATA TTTATGAAAG      720

ACCTTTTAAT TTTTTAGTTA TTAAAGCCCT TTCTCTTTGT CAGGTTGTAA CTGAGTGAGC      780

TCTGGAGTTT GGAAAGAAGA TCTTAGAAAT GGGCCAGAGA GCTCCTTCTG AGATCCAAGC      840

ACGGAGAATT GCACCTGCTG TGCATGGTAA GAGAGTGTGC TTGGTAGCTC ACAAGGGCAA      900

GGTGAGAATA GAAACTTTCA TGCCTTTTTG ATGGGGGTTA TGAAATCCTA CCAAGAAACA      960

CCAGGTATCA GATGTGGGGT CCTGTTTTCC CAAAGCCACA AATGCTTGAA GGAAGATCTT     1020

GTGTGATAAA ATAATTACCA CATGAACCAA TCTTGCATGC ACAGCAATTT TGAGAGCCCA     1080

TCCTGGGAGC TAGGTGTGTA GTGTTTATCG TATTGTTGAG GCTCGTAAAA ATCTTGTATG     1140

GCTGCAGGCA AGCCAAACCC TTGACAGGCA CTGCATCTCC GCTGACTCTA AAGACCAAG      1200

CCCAATTTCT TCCCTGTATA TAAGGGGAAG TCTCTATGCT TGGGGTAGAG GAGTGTTTAG     1260

CTCCTTCCCT TACTCTACCT TGCTCCTACT TTTCTCTAAG TCAACATCGA ATTTGCCTCC     1320

TTCATTGACA AGGTGAGTTT CTCTCTCATT GCACTGGTAG GGCTGCCGCT GGTCCACTTG     1380

GGATTGGTGC AGTCAAAACA CATGTAGGTT TGAACCTCAA GTTCCATGT TTACATGATT      1440

AAAAGGATGT TTTGTGGAAT GGTCTCCTAG GAGATATGTT AGATGTATGC TTGTGAATGG     1500

TGTTAATGAC TCTCTCTTTG ACAAAGGGTT CGTGGTCGAC CTAAAGGTGG GTCAGTGTGA     1560

CATTAACATT TAAGTGCTTT TTATTCAGCT CTTGAGCGGA ATTGGGACTC ATATCTGTTG     1620

AATGAAGATA ATAGAAATGG GGCTAACTGA ACTTTCCAGG GTGCAAGTGA GAACCCTGGA     1680

AAGGTCTTCC TAACCATAGA AAGGGAGTTG AGTGTGAACA TAGTATAGAG TGTTATTGTA     1740

-continued

```
GCAGAAAACA TGTGGTCAGT CAGTGCCAAA CATCTTTTGC TGTCAGAGGG GAGCTCTGCC    1800

TTCTAATAAT TTTACATTGG TACTGGATGA GGCTAGAGTT TTTTTATACT AATATCTCCA    1860

AAAATCAGCT CTAAAAAACT CAGATAAACC ATTTTTTTAA TTTTTTGCTT AATCATTAAT    1920

AGTGCCAATC CAAGGTTATC CACAACAAAT TTCAAATCCA ATTTTGAATT TTCCTGATAT    1980

ACTTTTGAAA TGTGTGTGTG TCCTGGGGAT GCAAACCAGT TTTTATGGTA ATATACCTAA    2040

CAAAATTTTG GAAGGCAAAT CTCTTAAATA CCATGCACCT ATTTCAAAAC ATAATTGCAA    2100

TAATTCTGTA TGCGCTTTGC TATTGGTATT TGTTTAGTTA CTCCCTTCCA AGCCCTCTCT    2160

GAATTAACAA GTTGGGTTTT ATTATGCAGA TGATATTAAC TTGATCATCT TCTTCCTATT    2220

TCTCTGTCAT GGTCAGAAGA TAGGAATTGA GGTTCTTTTC CAAATGAGGC ACAGTTCTCC    2280

ATGGCTATGA GACTCCATTT ATGCATCAGG AGTAAAGGGG TCTTGTGTTT TTAGGTGAGG    2340

TTCCTGGAGC AGGATCCCGG GTACCGCGGC CGCATCGATT CGATAAGAGA TGCCCTCTGT    2400

TTCATTAGCT CTAGTTCTCC CCCAGCATCA CTAACAAATA TGCTTGGCAA GACCGAGGTC    2460

GATTTGTCCC AGCCTTACCG GAGAAAAGAG CTATGGTTAG TTACACTAGC TCATCCTATT    2520

CCCCCAGCTC TTTCTTTTCT GCTGTTTCCC AATGAAGTTT TCAGATCAGT GGCAATCTCA    2580

GTCCCCTGGC TATGACCCTG CTTTGTTCTT TCCCTGAGAA ACAGTTCAGC AGTGACCACC    2640

ACCCACATGA CATTTCAAAG CACCTCCTTA AGCCAGCCAG AGTAGGACCA GTTAGACCCA    2700

GGGTGTGGAC AGCTCCTTAG CATCTTATCT CTGTGCTGTT TTGGTTTTGT ACATAAGGTG    2760

TAAGCAAGTT GTTTTTCTTT TGTGGAGAGG TCTTAAACTC CCCATTTCCT TGTTTTGCTG    2820

CAATAAACTG CATTTGAAAT TCTCCATGTC TCGATCGCCC TTGTTTACGG CACTGTCTAA    2880

CCTGGATGGG TGTTTTGTGA GGTAAAAGAA GACACTAGAG CCACATGGCA TATGGGAAAG    2940

TCATGCACAC AAACATGAGA AAAATGCAGA GGCCAACCAG GCAACATTTC ACCAGACTGG    3000

AATCACAGAG AGAGCAAGCA CTTTCCCAGA TGGTGGGAT GTCATGGAGA AATGGAGAGA     3060

CCGGGTGACA GGTTTTGTTC ATTTGAGAAG GCTTTCTTGA AAAGGGCAGT GAGCAAGCAG    3120

GTTGGGAGGA AGAGGTGTGG CATTGAGAAG AAGGGAAAGT ATTGCATGAA AAAGTAATTC    3180

TTCACGTGGA ACAGCCAGTA AGGAGGGGCA TGAGTAATAT AGGGTCAGCA GTTACTGGAG    3240

CCAGAATACA GACTTTGGCC TGGGGAGTTC AAGAACTAAG AGTGGTAATA GAGAGTTGGA    3300

TATTCCATTT CCCTTCTCTT TTTGTGCCAC CACCCAAAGC TCTGCATAAT CTAAGAAGTT    3360

CCCTTGTTGA CACATAGCTC ATACTTGTGA AGTTGTACAA CAGGATAGCA TAGTGGCCAG    3420

AAGCATGGAC AGTTGAACTC AGATATGCTT GGGTTTGAAT CTTACCATCA CCATTTACTA    3480

GTTCTGTAAT ACAGTGCAAG TTACAGACAT CTCTGCACCT CAGTTTTAGT ATGTCTAAAT    3540

TGGGGATGAT AATGCCTTCC TTGTGGGGAT AGTGTGAGGA TTGAATAAGA TGAATACACA    3600

TGGCTGAGCA CACAGCAAGC ACTAAATAAG TGCCAGTTTT AATGATAACG GTGATGATGA    3660

TGATGATGAT GATGATGACG TAACATTGCT TGTGGGACTC CATACAGCTC AGTAGATGCT    3720

TGCTCAAAGA AGCAAGTTAC CAAAATTTTT GTAATGGTTC TATGAACGTG AAAAAAGCAG    3780

TCAACTTCTC TGAGGATCAA TTTCCTTAGT TTCCAATTAG GAAAAGTCTT CTTAGCTCCA    3840

GAGTCCCACA GGGCTAATGG AATAAGGAGA GGATAGATCA CACATGTATT ATGCAAACAC    3900

AACTCAGGTG AGCTCTATTC TTCCTTCTCA GTTATCCCTT CTGTAGGGAC CCCAGTGTCC    3960

CCTGCTGTCT TTCTGTGTCC TGACCGGAA ACACAGTGTG CCTTGTCTAC TCCATCACTT     4020

GGCCAGCTGC ATGCTTTCCT TTGCAGGCTT GAAGCAAAGC TGGGTCTCGG ACATTCTCAG    4080
```

-continued

```
GCACTGACAA AGCTGTTTAG TTGTTGCTGG GAAACACTGG GAAATAGCCC TTTTGTTAAA      4140

CACACAGAAA CTAGCCTTCG CCCTGAGCCA AATTCCTTAA ACTCGTCTAT GAAATTCCAT      4200

AACCTGACTC CTTAACTGCA GACATACCCA GCTAGAACAT CCCTCATGTC CCTGTCCACC      4260

GTGAGAATGC TGCACTTCAC TCTGAACCTT TAGTCCTCCT TTTAAATACT GCACACTGAT      4320

CACCCTGGTG TTTAGTGCTT TGTTTTTTGG AATCCCACCT GGCTCCATTT TGGGATGGTT      4380

CCGGGCACTT CCCTATGGAA ATTCCCTGC TGTCACTGTC AGAGTGAGTC CAGCAGTGGG       4440

TTTAGCTGGA TGAAACACCA CCATGTCCAT TTCCATTCAG ACTAATGTCA GAATTTGAAA      4500

GGCACTATGG TAGAGTAGAA AGAACAAGGA ACTGTACTAT TTAAAGGGCA GGCAAAGAAA      4560

AGGCATCTAT AGCTTATAAG ATGTGTGGAT CTTTGGATGT GACTTGGCCA TCCTGAGCCT      4620

AAGTTGTCTT GTAGGAGAAA TGGGAATGAG AATATTTTCC TCTAGACATC AAGAGGAAAA      4680

GAAATATAAC GTGAAAACCT TTGTGAATTG TGAATGTGTT ATACAGAGTA GCTAAAAGAA      4740

TTAAAAAGGG AGTGACAAAA AAGTAAAAGG CAGCTGGCTG CTCAGGGCCT CCATGGAGGG      4800

AAGTACCTTG ATATGGTCAC TGTGGCTCAG TGACAGCTCT GCAGGGACAG GAAATTGATT      4860

TGTTAGTGCA CCCAAAGTTG AATCTGCTCC TGAGTACTGA TTTATGGGAA CCAAACACAC      4920

AAGAGATGAA GGATGTGTCA ACCAGAATGT CCAGCATTAG CTTGTGGGGA AACACATACT      4980

TCCAGTGACT GAAATACCAT CCTGTTATCA AGAGATCTGG GAAACTAAAG TACTGACAAG      5040

AGCTGGCTTG ATCTGTGGAT TTAGAACAAT GAGAGTTAGG TGGCCTTGAG GGAGATGATT      5100

CACTCTCCTT CACAGAAGAG CTGACCTCTG GGGTCAACAG ATATAGCACC TCTTTCCCAG      5160

GGACGCTACT GAATGAACAG TGATGTGTTC TTATACTCTG GCCCAGATTT TCTACATACT      5220

TTCTTAGGTT ACAACTTTAT TTAGTCACAT TTCAGTACTG GGGATACTCC TGTTTATCTT      5280

CTTTGGACTC GAGTTTTTAT GGGAAGGTCA TGAAACAGAG AAAAATACAA TTTGCAGGGA      5340

AACTTACCAA GGCTTGTAAG GTTACAAGGA TTAAATGAAA ACCCTGTGTA AGTCAGTATA      5400

TAGTGAAGAA GTAAATTGAG TTAGACCAAA CGCCAAAATG CATCCGCATT AGAAAGACGA      5460

TAAAGGAAGA CTCTGGATTC AGTTCTGTTC AAAAAACATT TTCTGCACAA ATACTATGTA      5520

TGAGGAACTG GGCGTTGGGG AGATGATGAT GAGTGAGACA TGGTTCTTGC TTTCAGAGAG      5580

CCTAGAGACC TGGGTGGTAG CAATGGTAGA GATACATCCA AGACACAGAA ATAGATATAC      5640

AGGAACACAG ATGATTGAAA GTGATGCTTG GCAGGGCTTT AAAGAATGAA TCAGAGTTTT      5700

TCAGGCAGAC GAGGATCTTC AAGGCAGAGG GAATCATATA GATAAGGACA TAGAAGAGTG      5760

AAATTTCATG AAGTAGTTAA GCATCTGAAG AAGCATGGAA TTAGTGACAA GAAATGATGC      5820

GGAAAAGATA TCCAGATCCA ATCAAGAAGG GCCTTGTTGG CATTCTATGG AGTCTGGACT      5880

TTGGCTTCTG GGTCACAAGT TCTCAGATGG GGTTTTCATA TCTATTATTA GACCTACTAT      5940

GTACTGGTCC AGTGGAAGGG AAAGGGGTTG TCTTACTGCT AGTGGAGTAG GAATTGGGTA      6000

TGGACCACAG CTTGTCTTGT TTCCAAGTAT TCCCTAAGAA ATCTGGTCTG CTGATGGGAG      6060

ATCTATTTAT GGAAATGTCT TTTTCCCTCA GGAATTTTAT GTCGGAAACA GCTGTCATAG      6120

GTGAGGAGGA ACTGGTAAAA GTACTTAATA GGAGAGTGTC ATGGTCAGAT TGGTGTTTTG      6180

GAAAAGTCAG CCAGGGCAGA TTGGAGAGGT CCATATTGGA GGCAGGAAGA CTTAAGAGAC      6240

TATTGCAAAG GTGAAGACAA AAGACGATAG GGACTTGCAC TTTAATTCCA GCCCTTAGAA      6300

GTAGTAGAAG GTCAGAAATG AGAATATGCA TTACAGAGAT AGTTAGTTGC TATATCATTA      6360

GGACTTGGTG ATAGATTGGA TGAGGATGCG GTTGGGTGAG GCAAAGAGGA GAGTCCACAT      6420

TCCTGGTCTG GGTAGTAACA AAGAATCTAG CAAGAGGGCT TGTGGGAAA GATGCTGAGT       6480
```

```
TACGTAGCAA GTGCATCTGC TTTATCCTTG TAATGAATGG GGCTAAAGGT GTAAACCAAA    6540

GAGTCATCAG CATTTGGAGG GTAGAATAAA TCATCAGATA ACTCAGGAAG AAGGAGCAGA    6600

AGAATTACTG ATACTCCCTG GAAGGAAAAC CGGAAGTAAA TGGGAGAAAC TTGCTCAAGT    6660

GGACAAAGTT AACAGACAT GAAGCATGAA TTC                                  6693

(2) INFORMATION FOR SEQ ID NO: 3:

(i) SEQUENCE CHARACTERISTICS:
          (A) LENGTH:           24979 base pairs
          (B) TYPE:             nucleic acid
          (C) STRANDEDNESS:     single
          (D) TOPOLOGY:         linear (ii) MOLECULE TYPE:         DNA (genomic)

(xi) SEQUENCE DESCRIPTION: SEQ ID NO: 3:

GAATTCCAAG CTTTCTGCTG TAAGGAGGGA CCTCAGGGAG CCAAGGTCAG CCTGCAGCCT      60

TTCTGTGCTC CTTTGCCTCG CCTGACAGGT ATGAGGATGA AATCAACAAG AGGACTGGCA     120

GCGAGAATGA CTTTGTCGTC CTGAAGAAGG TGAGGGAAAG GGGAGTCCTG AGGGTGGCTG     180

TGGACCCAGG AGGCTGAGGG GAGTGAGGAA TCCCTATGGA TGCTCTGTGA CAATGGCAGG     240

GTGGCCTCTA CGGCCGGCTT GCTGTGTATG ATGCCTGAAT GCGGGCCCT TACATTGGAA      300

CTGACACTGA TAATGACTCT TCAGGAAGCC TTGAGTTCGT ATCTCTCTGG GGTCTGAAAG     360

TGAAATGAAG TGAAATGACA GCTTTTGAGT GTCAGTTACC TGTAGCCTTG GGACCTAAGG     420

AAGGACCTGG GGTGTTGGTT GTGACTGACT GGGATGTGGA GGTTGGTGTC ACATCTCCTT     480

CTGGCCAGGA AAGCCAGGAC TTGTGGGTCC TTATTCGAGT GCGGTGATGA ATTTTTTAAG     540

TAAGGAAATA AACCTAGAGT GGCTCTGGTC CTGAGCCAGC CAGTGAGCTG TGGCAGGCAA     600

TGCCTGGGCA ATAAAGTCAA ACTGTTCTGC CTGCTATTCA GGATGTGGAT GCTGCTTATG     660

TGAGCAAAGT GGACCTGGAG TCCAGGGTGG ACACTCTGAC TGGGAGGTC AATTTCTTGA      720

AATATTTATT TTTGACGGTG AGTTAAGCCT TTATAAGAAC CTCCTTTCTT TTCTCACATC     780

TCACAAGGAG TATGGGCTGT AAGAGGGGAG GCCTGAAACC CAACACTACC CACTAGGGAC     840

TCATCTCCCC AGGTACCCCA ACTCTGTGGG CCTGGAGTCA GCCATCCTCT CCACCCCAAT    900

CCTCAGAATC CCCAGGTCGG GGTAATGAAG ATGGAAGGCT GGGAGAATCC TGAGTTAGGT    960

GGAGGCGAAT GTGTCCCTGG TTCATGGCTT CCAATCTGTC TGGGAAATCA CCCAGACATA   1020

TAAGGGGCAA AACCAACCAG AAATCTTCAT TAATTCTGGG GAGTTGATGG AGCTGTTAGG   1080

AACTCTGTGG GAGGTGACAG TGTGAGTCTC AAGGAGTGGA CTGACCTTAG TGATGGGGGA   1140

TCAAACACTC CACCACCCGG CCCTCTTTTG CCTGTGTCTA ACTTGGGGGT ACGTGCTCTG   1200

GGCCAGATGC TGTGTTAGAA GTTTATGTTA TGGGTATCTC CATTCTACAG ATGGGAAAAC   1260

TGAGGCACTG AGGGGTTAAA TTACTTGCTT CATTACCTAG CTAGTCAATG GTACAGCCAA   1320

GACTCAAAAG TGAGTCCAAG TGACTCCTTA ACTAGAGTCC ATCTACTGCC TCGGAGTACT   1380

CATGTGGTTT CAAGGAAGAG GCATGCCTGC CAAGGAGCCC AGCTCACTAT GGTGGCCAAG   1440

TCAGAGCAAG GCAGAGTGGC AGCTGCAGGA GAAGTGTGAT GGGGAGATGG TATCTGAACG   1500

CTCCAGGTTT AGGCTCCTTC CTTCTCCCCT GGAAGGCAGT TAAGACTCTC CCTATTATCT   1560

CTCATTGCAC ACAACAATTC CAAGAGCTTT TCCCAAGACT ACCTGGCCCA GGCTTCTGGC   1620

TTCCCCCGAG AGCCTTGAGG GAGCAGCAGA GGAAAACTGA GGCCCCCAGA GGAGAATGGA   1680

AGGAGTCAGC CTGTGCGCCA TGCCTCGCAG GAGCTGTCTC AGGTGCAGAC TCACATCAGC   1740
```

-continued

```
GACACCAACG TCATCCTGTT CATGGACAAT AACCGTTCCC TGGACCTGGA CAGCATCATC  1800

GATCGAGTGC GGACCCAGTA TGAACTGATT GCACAGAGGA GCAAGGACGA GGCCGAAAGC  1860

CTGTACCAGA CCAAGGTGGG CGTGGCCCAG ATCTGGTGCC CAGAAAAACA GATTCTTCCC  1920

AGAATTGTCT TTCTCTTATT GCATTGTCTT TCTCTTATTT CTGAAGTAAA ATGTGTTTGT  1980

TATACAAATT CTAGAAATTA CATGTAAAGA TTACCCATCT CTCACTACCG CTATTAATAT  2040

GTTAATATCT CTTCTACCAG TTCTTTGTCG CTATTAGGCT AGTGGAAAAG TGATTGCGGT  2100

TCTCGCCATT AAAAGTAATG ACGAGAACTG CAATTACTTT TGCAAAAACC CAATAATGTT  2160

TATTGAGAAC TCATATGTGT TAGGCACCTA GCAAAGTGCT TTACTTATTT ATTATTATTT  2220

CATTCAGTCC TTACAACAAC CAATGAGGTA AGAATTTCGT TATCACCATT TTATAATAGA  2280

TAGTAGTGTG TGACATTACT TAATTTCCCT AATGCCTTGT AGCTAGTAAA TGCAGAGCCA  2340

GAGCTTAATT AAAATTGGTT TGTGTCTACA AACCCATTCC CCTCACCACT AGAATGATTT  2400

TTATTCTTTT TTCATAATGG TATCTATTAA AATATATTTT TTTTACTTTT TTTTTTTTTT  2460

GAGATGGAAA CTCACTCTAT CTCCCAGGCT GGAGTGCAGT GGCCTGATAT CAGTTCACTA  2520

CAAACTCCGC CTCCTGGGTC CAAGTGATTC TCCTGCCTCA GCCTCCTGAG TAGCTGGGAT  2580

TACAGGCACG TGCACTACAC CAAGCTAATT TTTGTATTTT TAGTAGTGGC AGGGTTTTGC  2640

CATGTTGGCC AGGCTATACT TTCTCTTTTA CTTAACACAT ATGGATACTT TTCTGTGACA  2700

CTAAATAACC TGCCGCATTT TTAACAGCCT GGTATTATAT TGTTAGACTA CACCCTCCCT  2760

TATTAGATCA ACTCCTTTGT GGCTAAGTTG TTGGGCACAT CTTTGGTTAC TTCTTTTCCA  2820

TAAACTGACC TGGATCTTTT TGGATGGTGA AGCCTCTGGT TGAAAGGGTG TGGCTGACAG  2880

TCCAGTCACT AAATTCTGAA CAACTAGCAT TGATGACTGG CTTTGAGGAT GATCTGTGGC  2940

CAACTCCAAT CCTGGCTGAC CTCTGTCCCA CGGTCCTGCA CAGTGTTCTG GGGTGGAATG  3000

GATTTCGACA TTAGACTAGG AAGCCAGATG GCCAACAGTG AAAAATAGCA GAGTGTACCA  3060

GATTCCCTTG CAAGTCGATG CTTCTCCTAC CCACTTCAGA GCCCTGTGCC TGGGGGGTGG  3120

AGTTCTGACT AATGGGCAA TACAGAGACA GAAACAGAGA TGGAGGGAA ATGAGACTGA  3180

ACGTGGAGCC AATGGAGGGC CTCTGAGGAC ATGAGGTCTG CTTGACTGCT AGGGAGATCA  3240

TCCTGGAAAA GGGTGGGAAG CTATATGGTG GGTGGAAAGA GTGAGGGGGT CTCAGTGTGG  3300

GTAAGGACCA ACGTGAAGGC TTAGATGTGT GAAAAGGTGG TAGAAGGGCA TCACAAAGCA  3360

GGTTTGTCTG GCCTGGGATG AGAGTCTGCC CAGAGACTGG TGGGAATGCG GGAGGCTTGG  3420

GATAGTGTGA GTGTGTGCAT GTATACATGT GTTTGCAGCC TGGGTGAGGG AGGTTTGGTA  3480

TAGCTGTGAG TATGCATGTA GGGGTGACCA CAGTGCAAGG TGGGTGGGAA TCTCCCAGGG  3540

GAGAGCAGCC CAGACCTACT CCTCCTGGAG GGGCTTGTGG TGGGCAGCAC ATGCTGACTA  3600

TGATGCTCGC TTTGGCCCCA GTACCAGGAG CTCCAGATCA CGGCAGGGAG ACATGGAGAT  3660

GACCTGAAGA ACAGCAAGAT GGAGATTGCA GAGCTCAACC GCACCGTCCA GAGGCTGCAG  3720

GCAGAGATCA GCAACGTGAA GAAGCTGGTG GGACGGGTGC TTAGGGAGGG CTGACCAAAG  3780

CCCTGCACCT CCTACAATGC CCTGCCAGAT CGAGCTCTGG AAACTTAACC ATTAAATGGT  3840

CTCCAACTGT CTCTGGAGCA GATTGAACAG ATGCAGTCAC TCATTTCGGA TGCTGAGGAG  3900

AGAGGCGAGC AGGCCCTCCA GGATGCGTGG CAGAAGCTGC AGGACCTGGA GGAGGCCCTG  3960

CAGCAGTCCA AGGAGGAGCT GGCCCGGCTG CTGCGTGACT ACCAGGCCAT GCTGGGGGTC  4020

AAGCTGTCCC TGGATGTGGA GATCGCCACC TACCGCCAGC TGCTGGAGGG CGAGGAGAGC  4080
```

```
AGGTGGGTCT GGCAGCTGTG TTTCTGGGGC TAAGGCTTGA GATGCACCAT GAAGCTGTGG    4140

GACTGGCTAT TTGGAGAAAA GATAAGCCCA CCTTTTTGGG AAGATTGGTA GCCAGGTGAG    4200

CAGAAACATT CCAATTAGAG GCAGAGGCTG TGTGAATGGA CAAGCCTCTT CACACAGGGA    4260

GAAGTCATTG TTATCATTCC TCCACCTCCA AGTAGAATGT CCTTATACCC AATCCAAGC     4320

CTCTGCAGCT GGTATTCACC CCCAATGCTA AAAGGCTTCA TGAAAACCCT GAAATTTCTC    4380

TCTGCCCCAC TGGCTTCCTG ACCTCTGCTC ATGCACACAC ATTTCCCTAA GGCTTGGGGA    4440

CACCTCTGAT CCAGATGTCT GTGGCCACAG CCTTCTCTCC TCAGGCCCTG TGGGTCTGGC    4500

TGACCGTGTG CTTTGGTTTT ACAGGATGTC AGGAGAGCTG CAGAGCCATG TGAGCATCTG    4560

TAAGTAGCAG ACCCAGGGGC AGAGAGAGGC TGGTGGTGCT GGGTGGAGGG AGGGCCAGGA    4620

GGTGGCCAGC AGAGAACGGA AAGTCTGGCA TTTTAGCTTC CAGTCCTGTG CAATAGACAC    4680

CAAAGTAAGC AAGTGTAATG CAAAGCCTGG AAGAATTCAT TTCAAATAAA TGGTTATGAT    4740

TTCAGGTCTG CTTATCTTAA TTGTTATGAT GCCTTTTTAT TAAATGATGC CTAGGAGGAA    4800

TCAGCAGCGG CTAGAACTCT TTAGGGTACA TATTCAATAA ACAATGTAAG TGTGTTGCTG    4860

AGAGGAACCC TGGCATCCCT TTGTAGTATG AAGAATACTT TTCAAGTAGG AACACTTTCA    4920

ATTTTCAATG TATCGGGTTT GCAAGTCGAT GCCACGGGTG ATCGAGGATG GAGGAGGCTG    4980

CAGGTGCAGG GCGGGTGCAG GTGGGGGCCT TGCCTGTCCC TCTGACCCCG TGTGCACTGT    5040

CCCTACCCAC AGCCGTGCAG AACAGCCAGG TGAGCCGTCA ACGGCGGCGC GGGAGGCGGC    5100

GGCAGCTACG GCTCAGGAGG CTACGGCGGC GGCAGCGGTG GGGGCTATGG CGGCGGAAGA    5160

AGCTACCGCG GAGGCGGGGC ACGAGGCGGG AGTGGAGGCG GTTATGGCAG CGGCTGCGGC    5220

GGCGGTGGCG GGAGCTACGG AGGGAGCGGC AGAAGCGGCC GCGGATCCTC GCGCGTGCAG    5280

ATCATCCAGA CCTCCACCAA CACCTCCCAC AGGCGGATCT TGGAGTAGAG GCCTCGTTTC    5340

TGCCACACAT CACGCCTGCC CCTCACCGAC CTCTCCTCAA ACTCCTCCCC TCCACGCCCT    5400

TCCTAATCCC CTCTCATTCA CTTTTCTTAA TGGGTCTCAG CAATTTTGCC AATAAATTCG    5460

ACTCTAATGG GGGAAGCAGG GTGGATAAGT CCAAACAGCA GATCTCTCTT TTGGAGGGCA    5520

CTGGCTTGCA GTCAGATTCA CAGCTAGGCA CATTCTCACT CAGACCCCGC TCTGCTGGCC    5580

CTGCTGCTGT TCCTGCTCCC ACCTTTTTGG AAGATCGGTA GCCCAGGGTG AGCACAAACA    5640

TTCCAGTTAG AGGCAGAGGC TGCGTGAGTT GGCAAGGTAG GGAGAAGTCA TTGTTATCAT    5700

TCCTCTGCCT CCAAGTAGAA TGCCCTTATG CCCCAGTTCA AGCCACTGCA GCTAAGTATT    5760

AACCCCCAGT GCTAAAAGAT ACCAGGCATC TAGTTTAGCA ATGGAGGGAA ACAGAAACAG    5820

CCTGTAGAGA GCATCGACAA GGCGCATAAT GGAGAGTTGG TATCTCAACC CCAAGCTCCC    5880

TTTGCTGTAC CTGGGCCTGC TCTGTGAACA AGAATCCACG CCCCCCTGCC CTGCTGGGAC    5940

CACATAATGA TCCCTTTGGG GAAGTTGCTG ATTGCAGGGC AAGCTAGCTT GGTAAGGAAA    6000

ACCTCTGCAC CAGCGGCCTA TTCCTGCCTC TTGGTCCATA GCCTCATACA CTCATGTTGA    6060

TGGATAGTAT AGATTTGCTG CCCACACCAG ATATCTGTAA GGCATCACTG TCCTGATTCT    6120

GAACCTCTGT TTCAGGAAGC ATTCTCCCCT GTGTAAACAA CTCAAGGTGG AAGTATTTCA    6180

GAGGGCATAG GGTCATGAAT CCTTACCCAA AGGAAGCCTG TTTTAGCAGT GGATGCAGGA    6240

GTTGATGAAC AGACAAGCAA GTTCTGCTTC TGTCCTGTTT CCTCCTGACA GCTCCATTCT    6300

TTTGAAGCCT GACCCTTCCT AAGCTCTGCA TCATAACCAC TCTGAGAATT GCCCCATTGG    6360

TGGGCATGTG AAGCCAGCTC TGTTCCATCC AGGTGCCTCG GGCCTGAGGA GTCTGAGGAT    6420

CTGACTTGGG TCTTGGAAGG GTTCCAACCC AAGTCAGTCA GGAAGCTGCC CATTTTTTTG    6480
```

```
CAAGGCATTT TAATGCCTTT CCCAGACCTC TCTAGTCCCT CCTGCCTTCT GTTCTCTCGA      6540

CAGCTGTGAG CCCTTTAGAG AGAATATGAC TCTTAATTTT GAATCTTATG TAAGAGGCTT      6600

GAGATGTGCT GGAGAGGGCA GGAAGAGGAA AGTATCAGGC CTTGAGAGAG GGAATGTAGC      6660

TTTGCTTCTA TGATCTGGAG TCACCTTCAC TTGCTAGCTG AGTCCTAACA CAACTTCCAA      6720

GTCCATGATT CTCTTGGGGC ATTGGATGGG CTCAGTGTGG GTCTCTTAGG CTGTTCTTGT      6780

GACTTCATCA TTTCCTGGTT CAAAGTTGTA CTGTCAAGGG GCAGCATTTC TGGTATTTCT      6840

ATAATAAATT TTCTGTGATC TCAAATTGCT GTTTGGTCAG GAGATGCATT ATTTCTTCTT      6900

CTTCTTCTCC TTCTTCTCCT TTGCCTTCCT CCTCTTCTCC CTCCTCTGCT TCTCCTTGCT      6960

CCTCTGGCTC CTCCTCCGCG CTCCTCCTCC TCCTCCTCCG CGCTCCTCCT CCGCGCGCTC      7020

CTCCTCCTTC TTCTTCTTCT CCTTCTCCTT CTCATTCTTC CATCTTCATC TTCATCTTCT      7080

CCTCTTTTTC TTCTTTCTTC TAAATAAAGA TGGGGTCTCA CCATGTTTCC AAGGCTGGTC      7140

TTGAACTCCT GGGCTCAGGT GATCCTCCCA CCTTGGCTTC CCACATTGCT GGGATTACAG      7200

GTGTGAGGTG TGGTACCTGG GCTATTTCTT TAAAAATTTC TGCAGACCTC TGAAATTATT      7260

TATATTTGGG AAGTTAAAAT TTCTTCTTAT TTTTTATTGT ACAAGTAATA CACAGTCTTG      7320

AAGAATCTTA CAGACATAAT CTTATTAATC CTTAAAGTGG CTGATCATCC AAAAGTCAAT      7380

TATACATTTG TTCAATGAGC ACTTATTAAG CTCCTACTGT GTGGCGGGCA GTGGCTTAGG      7440

CACTGGGAAT GCAATGTTGA ATGAACATGT TTCTGACTCT TAAGTTGCTC ACAACTAAAT      7500

GACATATTAT GGGGGAGGGA CGATTCAAGG AGAGAAGAGA AATCTGAGTG TGCTTCTAAG      7560

GACCTCTAGC CTGAGAGTGG AAGCAAGGCC TATCCTGAGG ACACAGGCAG ACCCCCCAAA      7620

ACAGGAACAG GTGGGACTTA CGACAGGTGC CAGTGCTGGG GAAGGGACGT TTGGTTCCAA      7680

CAGACTCCTG GAGGACTGGG ATATGGAACA GGGCCAAGGA AGAGAGGTGT GGGTGGGGAG      7740

ATGAGGGAAG GGCCCTCCAA ACAGGGGGAT AGTCTGCTCA GAGACTCAAA ATAAGAGAGA      7800

GTGTGGGGGT GAGAAGGAGC AGCTGGACAG GAGAAACTGA GCTAGGGAAG GAAGGGGCTG      7860

AGGCCACAAA CTGAGTGGGG TCATGGGCAG AGACATCTTC AATTGATGCC TTGAGGGAAG      7920

CAGAGATGCA GAAATTCCAT AATGGAGCAA GTTAAGCCAT CACCTCATCC TATGTGGTAG      7980

TTCTCAGTCC ATGTAAAAGA ATCACATAAA AGATGTGATC TACTTTCTAA TTCCCTGGAG      8040

GACTTTGCAT GCAAATTTGG ATATGGGATT CATTCGAATA TGACAGGAAC CCCATATTGA      8100

TAAGACACTG TTGCTCCCGG GTGGGCATTG TTCAACTCAA GACTTGATGA CCCAGATAGG      8160

TGTGTCTTTG CAGTTAGCTG TCACATGTCC CACCGTTGAA AGGTGGGCTT CTCCTCCACA      8220

TGTGCAGGGC TCTCTGCCTG CCTTTCCCTT TTCTCGTGTC CTCTGACAGC CTGCTGCCAG      8280

GATAGATGAG ATGGGGAGAA ACTTCTCAGA GAGAATAGAG GGGTGTGCAT GGAAACAGAG      8340

TGTCTTATCA CTATGGGTTG ATATGATGTT TGCAGTTAGC TGCCACATCC TCCCCAAAGA      8400

CTTCTGGAGG GCATGCCTGG GAACACAATG TTTTATTCAT ATGGGTTGCT GTCCTATTCC      8460

AATGAATCCC ATATCCAAAT TCCATCAATA TCGCCTTCAG GAAGCTACAA CATATTCGGC      8520

TCAATATAAG AAGCACCTTT CTATGATCCT GACATGGGAG AGGCTACCCT GGGGAGTGAT      8580

CAAGTTTCAA GTCAGAGATT GGCTAACCGT TTGGCAGGAA CGTTGAGGGC GGGAGTGGAG      8640

ATGGGTGGGG ATATGGTATG GAGGCATCTC ACTACTTTGC TGTACTAAGA GTTCACATGG      8700

CGAAACCTGA GAAAAAAAAT TCTACTCTCT GTGTTATATG GGAAGAATAA GGTCAGGTGC      8760

CAGTGAAAGC TAAAGTCACA AAGAAGCCAA AGGCCCTAGC CAGAACTGTT AAATGAGGCT      8820
```

-continued

| | | | | |
|---|---|---|---|---|
|AAGTTTTCTG|GCAGCACAGG|GTCTATTACA|GGGTGTGAGT|TTGATTATCC CTGGGATCAT 8880|
|GCATGTGTGA|TACTCTAATG|GGATCCACGT|TGGCTCTGAG|AAAACACGCA AGGATAAGGC 8940|
|CAACCACAGC|TCTCCTTTCC|CATCCTCTCT|TGGGAACAAG|TTGAGATTGT CCCAGAAAAT 9000|
|GTGGCCCTGA|CTTATCTCTT|CCGAATTCCT|TGATTTTGTC|CTGTCATGGA GGCCTGGGGG 9060|
|ACAGATGGAG|GGAATCATGT|GCCTGAATCT|GAAGAATATT|GGAATAGAGA TTCCACAAGG 9120|
|TAGGGGCAGG|AGAAATAAAG|GACAGAAAGG|AGAGGAGTTG|GTCAAAGAAG GCATCTCAAC 9180|
|GTCTAAATGA|GAAGTCTTAA|TTCGATGTTC|AGGGAAAGAA|AGAGTAACTT TAGGGACCTA 9240|
|AACAAGGAGG|ACTAGCACTA|AGACACTGAA|GAGATTTCCT|GAAATAGACA ATATTTCCAT 9300|
|CAGAGACAAT|GAGAAATCCC|ATCAGGAGAA|AATGTCTCTC|ACTTTCAGCT CACCCCAGTG 9360|
|AAAACAACAA|GCATTCTATA|AACCATGTAG|GAAATGCCCA|CACATGCATT ATCTCACCTG 9420|
|AGTCCCACTC|ACCTGGGAGT|GCGGAGACCA|GGTGTGGGGG|TCTGCAGTCC TTCTAGGGAC 9480|
|CATGGAGTGC|TCCATCCCTG|CCCCTAATCA|ATGCTATTCC|CACAAGGCAG ATACTCAGAG 9540|
|GGAGAGCCAA|GCAGGCTCAT|TGCAGTGCAA|TAAAGCCAAG|AGGCTGGCAG GAGGGAGCAA 9600|
|ACACCCGGGT|TGGTGAGAGT|CCCAGGGAAA|GTCTGCCAGT|CTGCTCTTTG CTCTGAGAGG 9660|
|CAGGGTGGCA|GGGTTGGGGC|ACTCTGGAAA|TATAAATTTA|GTTCCACCAG CTTCTCATCC 9720|
|ACAGAGATTT|TGATCTGAGG|ACATGGTTAA|CTGGAGGAGC|AATCATTGAC TCAGTAAAAT 9780|
|TCTAACTGCA|TCTGACCTTA|GACAAGGTGT|GCGTTTCTGG|GCTGGGAAAG TTCCTGGTCT 9840|
|GAGGAAGAGT|CTCTTGAGAA|TGTCATCTCT|TTTCAATTAC|CCAGCCTTTT GGCCCAGAAT 9900|
|GCATCTTCAA|ATTAATGAGC|CATTTGCTGG|TTAATTTGGT|CCCAGGGAAA AAAGTCCAGC 9960|
|AAATTACTGG|GCATTACACT|GAGCTTGAAG|GTCCCTCTTC|AAGGTTGCCC TGGTTTTATC 10020|
|AGCTTTCCGA|TCAGTCTGGG|AAATGGGATG|TCTTCAAGGC|TGATCAATGC TCTGTTGAAG 10080|
|GGCTGGCTGG|GAATTTGGGG|TATTGGGAGG|TTTTCTAGCA|TGGAGTACGG CTCCGAGTGG 10140|
|CCCAATCCCA|AGCCTGGAAG|GGCTTCCAGG|GGGCTCTAAG|TGTGCATTCT GACCTCCACA 10200|
|CCTGCCCCTG|TGTGCTCAGC|CCTCAGTGTT|TGTGCTCCCC|CTGCAGAGCA GCTCTGCAGT 10260|
|GAGGGCAAAG|GCTCCTCGCA|TCTGGCCCCA|GCTCCCTCCA|GCCTCAGGTG AGCCCGGTGA 10320|
|TGCACCTGTG|ATCTCTTCTT|CCATGTGATG|CCCCCTAGCT|TTCCCAGGGC AAGTCCGTGG 10380|
|ACTTCTTAAG|GCTTTCTCTC|ACAAGATGAG|GAAATGGGCC|CATGTCAAGG GCTTAAATGT 10440|
|CCTGTTCCAG|CCTTTTCACT|GTTTCCAGTA|AATCAGGGGC|TTGTTCTAAA GTTTGTTTTT 10500|
|TTTTTTCTGG|TTATTATATC|AGCTTCTGGG|TTCTCTCAAA|TGCAAGAGTG AGGGAAAATC 10560|
|TTCCTTTTTT|CCTTTTTTGA|GATGGAGTCT|TCAGCATCAG|TAGCCCAGGC TGGAGTTCAG 10620|
|TGGCGAGATC|TCGGCTCACT|GCAAGCTCCG|TCTCCTGGGT|TCACGCCATT CTCCTGCCTC 10680|
|AGCCTCCCGA|GTAGCTGGGA|CTACAGGGCC|TGCCACCACA|CTGGGCTAAT TTTTTTTGTA 10740|
|TTTTTAGTGG|AGACGGGGTT|TCACCTTGTT|AGCCAGGATG|GTCTCGATCT CCTGGTCTCG 10800|
|TGATCCGCCC|ACCTCTACCT|CCCAAAGTGC|TGGGATTAAC|GTGAGCCACC ACGCCTGGCT 10860|
|CCTTTTTTCT|TTATCTATAC|TCTACTATGC|TTCAGTTTCC|CTGGAAGGTA CATAGAGCCT 10920|
|CCTTTTACAG|AGAGAACTAG|CTCAGAGAGG|TCAGTGACCT|GCCTAGAGCA GTGCAGAATC 10980|
|AGGAGCGGAG|CCCAGCCTGG|CAGCCTCCAT|GGCACAGAGC|AAGATGGGCC CCACCGCCTC 11040|
|TCTCCTCCAT|GTTCATCTTT|GGTTTCCTCC|TTCCTGGCCT|CTGCTCTGCT CCAGCCTTGC 11100|
|TAGTGAGTGA|CTCCTGAGGA|CCTCCTTCTT|TGCTGTCCAT|CCTAAATAGG GCTGCCCCTC 11160|
|TGTCTGCAGC|TCTCCCTCCT|GCATAAGAAG|CCTTGCGCCC|TCCTCTGCTG CCTGGCTGCT 11220|

```
TTCAACATCT CGCCCCGCCT CCCCATTGTC TGTGATTTCT CTTCACTCCA CCCAGGCCTC    11280

AATTTTCCTC ACTCCCCTGG GATTTCCCTG TCCCATGTCC CTGGTGGAGT CCCTCAGGGT    11340

GGGTGGTTGT CATGCAGTGC TTTCTTCACT CTTTTCTTGG TCCCATCCCA CAAAAGCTCT    11400

CAAAACATCA CCACACCTGC TCCTGCCCAT GCCCCACAGC CACCCCTGGC AGCCTCATCT    11460

CAATGATCAG TTCTGGGTTG TGTGTGTGAG TCCTTGGGTG GGGGTGTTTT GGTGCTCTGT    11520

CATCAGCACC GCTGGGGTAA CTCTCAAGTA TAAGGGGCCA TGTGGGATGC TGGGAGGGCA    11580

TCAAAAGACA CAGGGGACTT AGTCTTGCTT TCCAAAGGCT TCCAGAGTGA TTGAGGGGCC    11640

AGGAAACACA CAAGCACATG CATGAAAATG AGCCAACAAA TGCATCAATA TGTACTAAGT    11700

CTGGCAGCAG CCGAGCTTGG AAAAAGAGAC CAATAGAGCA CTTGCCCGAT GTGGACTGAG    11760

CAAAACTCCC TGGAGGAGAT GAGATCTGGA CCTGTCTGCT GCCTGCTTTG AGTGAGAGAT    11820

GAAGGCATTT GCCCACAAGC CCTGATGGAC CAAAAACAGA TTCAGGACCA AATGCTCAGC    11880

CATTGAGATC TTTGGTGCCC CAGAGCTTGA CTATGGGTAG GGATTTGTGG CAATGCCGAG    11940

GCAACCAGAA GACCTTTCAG AAAAGAGAAG AGTAGAAGTG GGCTTGGAAG ACAGAGAGGA    12000

ACAGGGATGG AAAGGGAAGA AGAGGGTGAT CAGTCTTGGG CAAAGCACGA GAGCTGAAGG    12060

GGTCAAGGCT GTGAGGCCGG GGAAGTGGGT GAGCAGGGTA AGATGTAGGT GGTGCTGGTG    12120

GTGAGAGCAG GCCAATGACA GAAGGAGCCC ATGTGATGCG GCGGGCTTGG ACTCTGGAGT    12180

GAGGCACGTG GCTTGTCAGT TACCTGCTGG ATGACTTTGG GCACATATTT CAACCTCTAT    12240

AAACCTAAGA TGCCTTTTCT TTAAAATGGG CTAAGAGCT CCCACGACGC AGACTTTGTG    12300

TGGTATTTAA ATGCAATGTG GCTCCTAACA GCATAGTTGC TGCGTGTAGA TGTTAGTGTC    12360

TCTTTCTTTC TCATTTTGTC TTTATTTCAT AAATGCACAG TCACTAAGTA AGAAAGGAGA    12420

GAGTGTGTGG CTCACACTTT CCTGCATGTG GTTCTTCATA TCCCACACAC CACACTGATC    12480

CTGGGACAT CACAGGAGAT GACGGGCCTG GTCTGGCAGC ACTGCAGCTC CAGCTCTGTT     12540

GGGCTGCCTC GAAAGTGGGC AGTGGAAAAA GAAAAGGAGT TTGATTCAAC AATTGGAAGA    12600

GTCTCAGGAA TTGACTTATG ACTTGGACAC TTTTTTTTTT TTTTTTTTT TTTTTTTTT      12660

TACTTTTTTG GGCCTGTGCT CTCACTTCTC TGTGAGGCAG GTTAGATGAT GTGACCTTTG    12720

AGGCCCCATG GATGAGAACA TTCTGTAATT CTCTGTGTAC TTGTTTATAG GGCCCAGTTC    12780

CACTTGCCTG TCTTTGAGCC TCTTCCCGGT TCAGGGAGGA ATGTCACTTG AATTGAAATC    12840

AGAAAACCCA GATTCTGCTT CCAGATGTGT CTTTTCCTAG CCGGAGTGTC TAGAGGAAGC    12900

CACTTAATCT CTGAGAATCA GTTTTCTGTT TCATGAAATG GGTTGAGAAC AGCTTGATTG    12960

CCTAGTTCTC AGGGCTCTTG TGGGATGCTC TTTGCATATG TGTTTGGTGG GGTGAGCTGT    13020

GCAAATGTAA GCTATGGTGA GGTTTATGGC ACTTATTCCT GCTAGTCCTG CATTTCTCCC    13080

TTCTCACAGG AGCACCTGGG GTATGTTTTG CAGCTAAGTT GTCTACCAAT TCCCTGACCA    13140

TTCATTCAAA CCTTTGATTT TTCTGTATGT CAGTTTCTTA GTTCAAAGAT GGGAGTGTGG    13200

ATCACTGCCA AGGTCTGTTT TTGGCTGGCA CACACATGCA CACAAACATG TGTGCACACA    13260

AACATGTGTG CCCAAACATA CTCACACCCC TCCAAAATGC TAGAAGGAAT CGATTGTGCA    13320

GAACAATATG TCTCATGAGG GAGTATGCTG AACTAAAATA ATTTTGATTG CTTGTCAGAA    13380

AATGATTAGG CAACAGTCAT TACCATGCCA AGACTGTCCC AGTCTCCATT GTTCCTAACA    13440

AGACCTGAAT TACTCATTCC CTAAAGAGAT GGTTGGTTTA GCAGCCGAAG GATTTTAGTG    13500

CTAGACAGAG TCCCAGACAG CAGTGCCACA GTGATGGCGA GGGAGAGGAG TAGCAGGGGA    13560
```

```
GCGGTGAGGG GCACTTTCTG GAGGAGGGTA TAGGGCAAAA ACTGGGAGGA GAAGAGGGAC    13620

AAGGTTCAAT AGCGGAGTGC AATGGAGAGG ACCGACACAG CCAGCCCGAT TCAGAGCCAC    13680

AGAGTAATGG GACCAGATGA TCTTCACAGA CTCCCTTTCT CCCATAGATC TTGCACACCA    13740

TAGTGGAGAC TTCCCATGTA CATCTATGGT TTGCCACTTA CAGAGTTACT TGGAGCCAGC    13800

TGAAGTTAGA GCTGGCTTCT CCCCTTTGAG TCTTCAATTC TGTGTTTATG TGCAGGCCCG    13860

GGGACCATGC CAGGCTTCTA AGAAGGTCTT CGAATGAAAG TCTGCTTGGG CTCTAGTGTG    13920

TCCAGATCTC AGTGCCACTA TTATCCACTG ATATTGATCA AGTGCTGCTC TCCAGGAAGA    13980

CCCCTGAGGT TTCCTGGTCC ATTGCAATGC ATGCTGGGTA CTCTTGCACT TGGATGGAAG    14040

TAAAATCTCC TCACTAAACT CTGTGCCACC AAAATCTCCT TCTCAGTGTG AATTGAAGAA    14100

ACATTTTCCA AGACTTGCAT GTGCCAGGAG CCAAGGACTC AGAGTGATAA AACAGCCTTC    14160

TGCCCTCAGA GCTCTCTGTG GTGGGCGCT TCCTGTGCTG TCTGGCTTTA CACACAGCAG    14220

GCAGAATGAC TTGAATTCGG CTGCTGTGCT GTCGTACAAC ATGCTGTTTA GGATCTTGCA    14280

CATGATAGCT AGGTATTCTT GCTTCAAATC GCAGGCACCC CACTTACCAA CTGTGTAGAC    14340

TTGATCACGT TATTCAACCC CTGTGTCTCT GCTTCCTCAT TTTACAAATG GGGAGAAAAA    14400

TAGCATCTAT CTCAAAGTTG TGAAAATTAA GCAAGTTAAT ACATATGTGC TACGTAGAAC    14460

AGTGCCTGGT ACATGGTCAG TTTTTGATAC ATGTTAGGTA TTATCATTAT TATCACCTCC    14520

AGAAACAATT TAAACTTCTC ATATAAGGCT CTCCAGACAC CTCTCATTGT CTTCCCTTCC    14580

AAATCTGCAT TTATCTCTCT CTCTTTGCAG TCCAGTGTGA GGCTTGAATC ACCTATCAAG    14640

CCTCACCTCC ACCCCTGTGC TTTACAAAAT GTCCTAGAGC TTCTATTTAC TCGTCTCACT    14700

GCTCTGTGGG CTTTTTCACT CAAGGGCGTT TGCATGCTAT CCATTGCTAC CTGTTTTCTG    14760

TTGCTGGTGT CTGTCTCCTG CTCTATCTTT GAAGAAAAGA AACAAGAAAA GGAATAACTG    14820

AGAAACAGAG AAAAAAAATG TCTCTCCCTT CTGGTTCTTC CAGACCACCC ACTCATCCAT    14880

CTTGTTCAAT GACAGCTTCT CTTCCTTTAA TTAATCACTG TGGTATATTT ATAAAGCTTA    14940

TATTTATGAA AGACCTTTTA ATTTTTTAGT TATTAAAGCC CTTTCTCTTT GTCAGGTTGT    15000

AACTGAGTGA GCTCTGGAGT TTGGAAAGAA GATCTTAGAA ATGGGCCAGA GAGCTCCTTC    15060

TGAGATCCAA GCACGGAGAA TTGCACCTGC TGTGCATGGT AAGAGAGTGT GCTTGGTAGC    15120

TCACAAGGGC AAGGTGAGAA TAGAAACTTT CATGCCTTTT TGATGGGGGT TATGAAATCC    15180

TACCAAGAAA CACCAGGTAT CAGATGTGGG GTCCTGTTTT CCCAAAGCCA CAAATGCTTG    15240

AAGGAAGATC TTGTGTGATA AAATAATTAC CACATGAACC AATCTTGCAT GCACAGCAAT    15300

TTTGAGAGCC CATCCTGGGA GCTAGGTGTG TAGTGTTTAT CGTATTGTTG AGGCTCGTAA    15360

AAATCTTGTA TGGCTGCAGG CAAGCCAAAC CCTTGACAGG CACTGCATCT CCGCTGACTC    15420

TAGAAGACCA AGCCCAATTT CTTCCCTGTA TATAAGGGGA AGTCTCTATG CTTGGGGTAG    15480

AGGAGTGTTT AGCTCCTTCC CTTACTCTAC CTTGCTCCTA CTTTTCTCTA AGTCAACATG    15540

AGTCGACAGT TTAGTTCCAG GTCTGGGTAC CGAAGTGGAG GGGGCTTCAG CTCTGGCTCT    15600

GCTGGGATCA TCAACTACCA GCGCAGGACC ACCAGCAGCT CCACACGCCG CAGTGGAGGA    15660

GGTGGTGGGA GATTTTCAAG CTGTGGTGGT GGTGGTGGTA GCTTTGGTGC TGGTGGTGGA    15720

TTTGGAAGTC GGAGTCTTGT TAACCTTGGT GGCAGTAAAA GCATCTCCAT AAGTGTGGCT    15780

AGAGGAGGTG GACGTGGTAG TGGCTTTGGT GGTGGTTATG GTGGTGGTGG CTTTGGTGGT    15840

GGTGGCTTTG GTGGTGGTGG CTTTGGTGGA GGTGGCATTG GGGTGGTGG CTTTGGTGGT    15900

TTTGGCAGTG GTGGTGGTGG TTTTGGTGGA GGTGGCTTTG GGGTGGTGG ATATGGGGGT    15960
```

```
GGTTATGGTC CTGTCTGCCC TCCTGGTGGC ATACAAGAAG TCACTATCAA CCAGAGCCTT    16020

CTTCAGCCCC TCAATGTGGA GATTGACCCT GAGATCCAAA AGGTGAAGTC TCGAGAAAGG    16080

GAGCAAATCA AGTCACTCAA CAACCAATTT GCCTCCTTCA TTGACAAGGT GAGTTTCTCT    16140

CTCATTGCAC TGGTAGGGCT GCCGCTGGTC CACTTGGGAT TGGTGCAGTC AAAACACATG    16200

TAGGTTTGAA CCTCAAGTTT CCATGTTTAC ATGATTAAAA GGATGTTTTG TGGAATGGTC    16260

TCCTAGGAGA TATGTTAGAT GTATGCTTGT GAATGGTGTT AATGACTCTC TCTTTGACAA    16320

AGGGTTCGTG GTCGACCTAA AGGTGGGTCA GTGTGACATT AACATTTAAG TGCTTTTTAT    16380

TCAGCTCTTG AGCGGAATTG GGACTCATAT CTGTTGAATG AAGATAATAG AAATGGGGCT    16440

AACTGAACTT TCCAGGGTGC AAGTGAGAAC CCTGGAAAGG TCTTCCTAAC CATAGAAAGG    16500

GAGTTGAGTG TGAACATAGT ATAGAGTGTT ATTGTAGCAG AAAACATGTG GTCAGTCAGT    16560

GCCAAACATC TTTTGCTGTC AGAGGGGAGC TCTGCCTTCT AATAATTTTA CATTGGTACT    16620

GGATGAGGCT AGAGTTTTTT TATACTAATA TCTCCAAAAA TCAGCTCTAA AAAACTCAGA    16680

TAAACCATTT TTTTAATTTT TTGCTTAATC ATTAATAGTG CCAATCCAAG GTTATCCACA    16740

ACAAATTTCA AATCCAATTT TGAATTTTCC TGATATACTT TTGAAATGTG TGTGTGTCCT    16800

GGGGATGCAA ACCAGTTTTT ATGGTAATAT ACCTAACAAA ATTTTGGAAG GCAAATCTCT    16860

TAAATACCAT GCACCTATTT CAAAACATAA TTGCAATAAT TCTGTATGCG CTTTGCTATT    16920

GGTATTTGTT TAGTTACTCC CTTCCAAGCC CTCTCTGAAT TAACAAGTTG GGTTTTATTA    16980

TGCAGATGAT ATTAACTTGA TCATCTTCTT CCTATTTCTC TGTCATGGTC AGAAGATAGG    17040

AATTGAGGTT CTTTTCCAAA TGAGGCACAG TTCTCCATGG CTATGAGACT CCATTTATGC    17100

ATCAGGAGTA AAGGGGTCTT GTGTTTTTAG GTGAGGTTCC TGGAGCAGCA GAACCAGGTA    17160

CTGCAAACAA AATGGGAGCT GCTGCAGCAG GTAGATACCT CCACTAGAAC CCATAATTTA    17220

GAGCCCTACT TTGAGTCATT CATCAACAAT CTCCGAAGGA GAGTGGACCA ACTGAAGAGT    17280

GATCAATCTC GGTTGGATTC GGAACTGAAG AACATGCAGG ACATGGTGGA GGATTACCGG    17340

AACAAGTAAG GGACCCTGTC TGGGCAGTTC TTAACTTTTG CTGTAAAAGA GTTCCAGAAA    17400

GTAATAAGCT AAGATCATGA AGCAGCATGT AGCTATGTCT TTTCTTAGGT TAGAGGCACA    17460

TCAGTTTGAC ATTTTCAGAA ATCTTCATTT TCTCAGGAGA TGGAAATAGT CTAGTGGTTT    17520

TATTGCTCAG TAGAAAGTAG TGGCCAATAT GTCCTAGGTT CATAATAGAA AGGCAGTGAT    17580

AGGCAATGCC ACCTTTAGTT TAGAATGCTG GACTTCAGGT CTTACCACCT CTGAATCTCC    17640

TAATTGTTTC TGCTTTCCTG CAGGTATGAG GATGAAATCA ACAAGCGGAC AAATGCAGAG    17700

AATGAATTTG TGACCATCAA GAAGGTAAGC AAATTCTGTA GGACGGAACT CACATTTGAA    17760

ATAAATAAGG GAAGAGGGTC TCCAATTACT AAGCAGAAAG CAGCCATGAT ATGGAGAGCC    17820

AGGTAGTAGA CCTGGGGAGT ATATGGAGTG GGCTATATT TTTCACATCA TCATGGACCT    17880

GGACTGATCC AGGCACTTGG CTTCTCCATA TTTCCCAGCA CCTTACATAG TAAGTGGAGT    17940

GGCAGATTCT CAGCAAGCCA GGCACACTCC CTTGATGGTG CTATCCGGGG GTGGGACAGT    18000

TAGGGAACTG TGATTTACCT GGGGCAAAAA GGAGTGGAGT AGACCCAAAG CTCCTTTTTT    18060

TGCTTGGAGA ATCCCCTCAC AGGTAATGAG AGGGACCTGC CCTGGAGAGA ACGTGCCTTC    18120

ATGATGTCCC TTGTTCCTCT AGGATGTGGA TGGTGCTTAT ATGACCAAGG TGGACCTTCA    18180

GGCCAAACTT GACAACTTGC AGCAGGAAAT TGATTTCCTT ACAGCACTCT ACCAAGCAGT    18240

AAGTCTTCCA GTTTCAACCA AGTTTATCTA AATGGAGAGT TTTTAAGCCG GAACCCACAA    18300
```

-continued

```
CGATTCAGAA GAATAGATAT TTATCTTTTA TTTCCTGACT GCTTTCTCTG TCTAAGTTGT    18360

TTTTTGTTTT AGTGCTGTAA GAGTCACTAA CCTATTATGT CTTGCAGGAG TTGTCTCAGA    18420

TGCAGACTCA AATCAGTGAA ACTAATGTCA TCCTCTCTAT GGACAACAAC CGCAGTCTCG    18480

ACCTGGACAG CATCATTGCT GAGGTCAAGG CCCAGTACGA GGATATAGCC CAGAAGAGCA    18540

AAGCTGAGGC CGAGTCCTTG TACCAGAGCA AGGTGAGTGG GCTGAAACCG TAGCCAGTTT    18600

CCCTGAAATG GCTTGTCTTG CTATCCTGTG TTATCTCATG TATGTGTGCC TGTGCCATGC    18660

TGAGTTCTGC CTACATTTAA CAAACGCTAT CTACCATCTT TAGTATGAAG AGCTGCAGAT    18720

CACTGCTGGC AGACATGGGG ATAGTGTGAG AAATTCAAAG ATAGAAATTT CTGAGCTGAA    18780

TCGTGTGATC CAGAGACTTA GATCTGAAAT CGACAATGTC AAGAAGCAGG TATGTGCTTT    18840

CTCCTTCTAC CACTCAGCTG TATGGAATGG GGGTAACCCT CAGGTAAAGG GCGAGTGCTT    18900

TCCTAGTTTT GAATCTTGCA ATTCAGCCCA AGGCTACATT ATTAGCCCTG GTTCCTTTTC    18960

TGACTATGCT AGTTTCCAGA ATGCAGCCAT CATGCTGGGT TCTCTTTAGG GAAATCTGTG    19020

AGAATGGCCT AGTAGAGAAA GATGGGATGG TCAATGTGAG TGATCTAGCC TATGACCCAA    19080

AGTGGACTTA AGAGTTGGGG AGTGAGAGGA AGGGCAGCCA GGAGGTTTTA GAGTAGGTGT    19140

TTAGAAGAAT GTCAAGTCTG TAAGGGTTGT AGGAGCCTTG ACTCAGGGCC AAGAGAGGCT    19200

GTTGAGTTAT CCCTAAGGTC TTTTAAGGAA GTCAACATGG TGATGTGTTA TCTGGAGGTG    19260

GGTGTGAGAT GACTTAAGGC CAAGTGGTTC TGTTGGACTC ATTATTGGCC TCACTGGAGT    19320

GGGGAGACCA ATTGGGATGA GGAGGCCTAG TGGGAATGC ATATTATGAG AGGGTGTCAT    19380

ATCTTTTTCA GATCTCCAAC TTGCAGCAGT CCATCAGTGA TGCAGAGCAG CGTGGCGAGA    19440

ATGCCCTCAA GGATGCCAAG AACAAGCTGA ATGACCTGGA GGATGCCCTG CAGCAGGCCA    19500

AGGAAGACCT GGCCCGCCTG CTGCGTGACT ACCAGGAGCT GATGAACACC AAGCTGGCCC    19560

TGGATCTGGA GATTGCCACC TACAGGACCC TCCTGGAGGG AGAAGAAAGC AGGTGAGGAA    19620

GGGACGCTGG GAGTCGAACC TCTTCTCATG GTCTTCCTTC CTTGCAAGCT GATTGTTGTT    19680

GAAGATGCAG CCATCTGATT GCAGCTTGTG CTGGGTATGG GGAAATGAAA AGTACACGGA    19740

GCAGGAGGAA GGACCTAGTT TTACTTTGGG AGCTGGAGTC CCAAGCTGTT TATTTTTTTC    19800

TTCTAGGGCT GTAACATATC TAGAAAGAGC TTTGAGGTGG AGCAAATTAT TCTTTATCTG    19860

GGCTGCCTCA GATGGCAGCT GGCCTAAAGT CGGCATCTTT AGAGGGGGCC TTCATTGGCT    19920

GCAAGGCTCG TCTCGTTTAT ATGGGAATTT CTCCGTGTTT GTACTCTTGC TGAGAAAAAA    19980

TGACAGGTCT GGGAGGCCAG AGGGGATTGG ATTAAGTTTC AGATTAAGTG CATTGGAGAA    20040

GACCCAGATG GGGAAAGTCT TCAAGGTGGT GGAGCGGGGA ATGGGGAAGC GGTTTGGGAA    20100

GCTGGAGTGT CCTGAGGAAT TTTCTTATTT TCTCCTACAG GATGTCTGGA GAATGTGCCC    20160

CGAACGTGAG TGTGTGTAAG TACAAGTCGA TTTCTCAGGG GCATGTGCAG GCTTTGTTGG    20220

GCTGGAAACG GAGTTGAGGT TGAAAATAAC TGAGCTTCCT CTTGCAGCTG TGAGCACAAG    20280

CCACACCACC ATCAGTGGAG GTGGCAGCCG AGGAGGTGGC GGCGGTGGCT ACGGCTCTGG    20340

AGGTAGCAGC TATGGCTCCG GAGGTGGTAG CTATGGTTCT GGAGGTGGCG GCGGCGGCGG    20400

CCGTGGCAGC TATGGCTCCG GAGGTGGCAG CTATGGCTCT GGAGGTGGCG GCGGCGGCCA    20460

TGGCAGCTAC GGCTCCGGAA GCAGCAGTGG GGGCTACAGA GGTGGCTCTG GAGGCGGCGG    20520

CGGCGGCAGC TCTGGCGGCC GGGGCTCTGG CGGCGGGAGC TCTGGAGGCT CCATAGGAGG    20580

CCGGGGATCC AGCTCTGGGG GTGTCAAGTC CTCTGGTGGC AGTTCCAGCG TGAAGTTTGT    20640

TTCTACCACT TATTCCGGAG TAACCAGATA AAGAGATGCC CTCTGTTTCA TTAGCTCTAG    20700
```

-continued

```
TTCTCCCCCA GCATCACTAA CAAATATGCT TGGCAAGACC GAGGTCGATT TGTCCCAGCC   20760

TTACCGGAGA AAAGAGCTAT GGTTAGTTAC ACTAGCTCAT CCTATTCCCC CAGCTCTTTC   20820

TTTTCTGCTG TTTCCCAATG AAGTTTTCAG ATCAGTGGCA ATCTCAGTCC CCTGGCTATG   20880

ACCCTGCTTT GTTCTTTCCC TGAGAAACAG TTCAGCAGTG ACCACCACCC ACATGACATT   20940

TCAAAGCACC TCCTTAAGCC AGCCAGAGTA GGACCAGTTA GACCCAGGGT GTGGACAGCT   21000

CCTTAGCATC TTATCTCTGT GCTGTTTTGG TTTTGTACAT AAGGTGTAAG CAAGTTGTTT   21060

TTCTTTTGTG GAGAGGTCTT AAACTCCCCA TTTCCTTGTT TTGCTGCAAT AAACTGCATT   21120

TGAAATTCTC CATGTCTCGA TCGCCCTTGT TTACGGCACT GTCTAACCTG GATGGGTGTT   21180

TTGTGAGGTA AAAGAAGACA CTAGAGCCAC ATGGCATATG GGAAAGTCAT GCACACAAAC   21240

ATGAGAAAAA TGCAGAGGCC AACCAGGCAA CATTTCACCA GACTGGAATC ACAGAGAGAG   21300

CAAGCACTTT CCCAGATGGT GGGGATGTCA TGGAGAAATG GAGAGACCGG GTGACAGGTT   21360

TTGTTCATTT GAGAAGGCTT TCTTGAAAAG GGCAGTGAGC AAGCAGGTTG GGAGGAAGAG   21420

GTGTGGCATT GAGAAGAAGG GAAAGTATTG CATGAAAAAG TAATTCTTCA CGTGGAACAG   21480

CCAGTAAGGA GGGGCATGAG TAATATAGGG TCAGCAGTTA CTGGAGCCAG AATACAGACT   21540

TTGGCCTGGG GAGTTCAAGA ACTAAGAGTG GTAATAGAGA GTTGGATATT CCATTTCCCT   21600

TCTCTTTTTG TGCCACCACC CAAAGCTCTG CATAATCTAA GAAGTTCCCT TGTTGACACA   21660

TAGCTCATAC TTGTGAAGTT GTACAACAGG ATAGCATAGT GGCCAGAAGC ATGGACAGTT   21720

GAACTCAGAT ATGCTTGGGT TTGAATCTTA CCATCACCAT TTACTAGTTC TGTAATACAG   21780

TGCAAGTTAC AGACATCTCT GCACCTCAGT TTTAGTATGT CTAAATTGGG GATGATAATG   21840

CCTTCCTTGT GGGGATAGTG TGAGGATTGA ATAAGATGAA TACACATGGC TGAGCACACA   21900

GCAAGCACTA AATAAGTGCC AGTTTTAATG ATAACGGTGA TGATGATGAT GATGATGATG   21960

ATGACGTAAC ATTGCTTGTG GGACTCCATA CAGCTCAGTA GATGCTTGCT CAAAGAAGCA   22020

AGTTACCAAA ATTTTTGTAA TGGTTCTATG AACGTGAAAA AAGCAGTCAA CTTCTCTGAG   22080

GATCAATTTC CTTAGTTTCC AATTAGGAAA AGTCTTCTTA GCTCCAGAGT CCCACAGGGC   22140

TAATGGAATA AGGAGAGGAT AGATCACACA TGTATTATGC AAACACAACT CAGGTGAGCT   22200

CTATTCTTCC TTCTCAGTTA TCCCTTCTGT AGGGACCCCA GTGTCCCCTG CTGTCTTTCT   22260

GTGTCCTGAC CGGGAAACAC AGTGTGCCTT GTCTACTCCA TCACTTGGCC AGCTGCATGC   22320

TTTCCTTTGC AGGCTTGAAG CAAAGCTGGG TCTCGGACAT TCTCAGGCAC TGACAAAGCT   22380

GTTTAGTTGT TGCTGGGAAA CACTGGGAAA TAGCCCTTTT GTTAAACACA CAGAAACTAG   22440

CCTTCGCCCT GAGCCAAATT CCTTAAACTC GTCTATGAAA TTCCATAACC TGACTCCTTA   22500

ACTGCAGACA TACCCAGCTA GAACATCCCT CATGTCCCTG TCCACCGTGA GAATGCTGCA   22560

CTTCACTCTG AACCTTTAGT CCTCCTTTTA AATACTGCAC ACTGATCACC CTGGTGTTTA   22620

GTGCTTTGTT TTTTGGAATC CCACCTGGCT CCATTTTGGG ATGGTTCCGG GCACTTCCCT   22680

ATGGAAATTC CCCTGCTGTC ACTGTCAGAG TGAGTCCAGC AGTGGGTTTA GCTGGATGAA   22740

ACACCACCAT GTCCATTTCC ATTCAGACTA ATGTCAGAAT TTGAAAGGCA CTATGGTAGA   22800

GTAGAAAGAA CAAGGAACTG TACTATTTAA AGGGCAGGCA AAGAAAAGGC ATCTATAGCT   22860

TATAAGATGT GTGGATCTTT GGATGTGACT TGGCCATCCT GAGCCTAAGT TGTCTTGTAG   22920

GAGAAATGGG AATGAGAATA TTTTCCTCTA GACATCAAGA GGAAAAGAAA TATAACGTGA   22980

AAACCTTTGT GAATTGTGAA TGTGTTATAC AGAGTAGCTA AAAGAATTAA AAAGGGAGTG   23040
```

```
ACAAAAAAGT AAAAGGCAGC TGGCTGCTCA GGGCCTCCAT GGAGGGAAGT ACCTTGATAT    23100

GGTCACTGTG GCTCAGTGAC AGCTCTGCAG GGACAGGAAA TTGATTTGTT AGTGCACCCA    23160

AAGTTGAATC TGCTCCTGAG TACTGATTTA TGGGAACCAA ACACACAAGA GATGAAGGAT    23220

GTGTCAACCA GAATGTCCAG CATTAGCTTG TGGGGAAACA CATACTTCCA GTGACTGAAA    23280

TACCATCCTG TTATCAAGAG ATCTGGGAAA CTAAAGTACT GACAAGAGCT GGCTTGATCT    23340

GTGGATTTAG AACAATGAGA GTTAGGTGGC CTTGAGGGAG ATGATTCACT CTCCTTCACA    23400

GAAGAGCTGA CCTCTGGGGT CAACAGATAT AGCACCTCTT TCCCAGGGAC GCTACTGAAT    23460

GAACAGTGAT GTGTTCTTAT ACTCTGGCCC AGATTTTCTA CATACTTTCT TAGGTTACAA    23520

CTTTATTTAG TCACATTTCA GTACTGGGGA TACTCCTGTT TATCTTCTTT GGACTCGAGT    23580

TTTTATGGGA AGGTCATGAA ACAGAGAAAA ATACAATTTG CAGGGAAACT TACCAAGGCT    23640

TGTAAGGTTA CAAGGATTAA ATGAAAACCC TGTGTAAGTC AGTATATAGT GAAGAAGTAA    23700

ATTGAGTTAG ACCAAACGCC AAAATGCATC CGCATTAGAA AGACGATAAA GGAAGACTCT    23760

GGATTCAGTT CTGTTCAAAA AACATTTTCT GCACAAATAC TATGTATGAG GAACTGGGCG    23820

TTGGGGAGAT GATGATGAGT GAGACATGGT TCTTGCTTTC AGAGAGCCTA GAGACCTGGG    23880

TGGTAGCAAT GGTAGAGATA CATCCAAGAC ACAGAAATAG ATATACAGGA ACACAGATGA    23940

TTGAAAGTGA TGCTTGGCAG GGCTTTAAAG AATGAATCAG AGTTTTTCAG GCAGACGAGG    24000

ATCTTCAAGG CAGAGGGAAT CATATAGATA AGGACATAGA AGAGTGAAAT TTCATGAAGT    24060

AGTTAAGCAT CTGAAGAAGC ATGGAATTAG TGACAAGAAA TGATGCGGAA AAGATATCCA    24120

GATCCAATCA AGAAGGGCCT TGTTGGCATT CTATGGAGTC TGGACTTTGG CTTCTGGGTC    24180

ACAAGTTCTC AGATGGGGTT TTCATATCTA TTATTAGACC TACTATGTAC TGGTCCAGTG    24240

GAAGGGAAAG GGGTTGTCTT ACTGCTAGTG GAGTAGGAAT TGGGTATGGA CCACAGCTTG    24300

TCTTGTTTCC AAGTATTCCC TAAGAAATCT GGTCTGCTGA TGGGAGATCT ATTTATGAAA    24360

ATGTCTTTTT CCCTCAGGAA TTTTATGTCG GAAACAGCTG TCATAGGTGA GGAGGAACTG    24420

GTAAAAGTAC TTAATAGGAG AGTGTCATGG TCAGATTGGT GTTTTGGAAA AGTCAGCCAG    24480

GGCAGATTGG AGAGGTCCAT ATTGGAGGCA GGAAGACTTA AGAGACTATT GCAAAGGTGA    24540

AGACAAAAGA CGATAGGGAC TTGCACTTTA ATTCCAGCCC TTAGAAGTAG TAGAAGGTCA    24600

GAAATGAGAA TATGCATTAC AGAGATAGTT AGTTGCTATA TCATTAGGAC TTGGTGATAG    24660

ATTGGATGAG GATGCGGTTG GGTGAGGCAA AGAGGAGAGT CCACATTCCT GGTCTGGGTA    24720

GTAACAAAGA ATCTAGCAAG AGGGCTTGTG GGGAAAGATG CTGAGTTACG TAGCAAGTGC    24780

ATCTGCTTTA TCCTTGTAAT GAATGGGGCT AAAGGTGTAA ACCAAAGAGT CATCAGCATT    24840

TGGAGGGTAG AATAAATCAT CAGATAACTC AGGAAGAAGG AGCAGAAGAA TTACTGATAC    24900

TCCCTGGAAG GAAAACCGGA AGTAAATGGG AGAAACTTGC TCAAGTGGAC AAAGTTTAAC    24960

AGACATGAAG CATGAATTC                                                 24979
```

(2) INFORMATION FOR SEQ ID NO: 4:

(i) SEQUENCE CHARACTERISTICS:
        (A) LENGTH:        8 amino acids
        (B) TYPE:          amino acid
        (C) STRANDEDNESS:  single
        (D) TOPOLOGY:     linear (ii) MOLECULE TYPE:        peptide (xi) SEQUENCE DESCRIPTION: SEQ ID NO: 4:

```
Met Ser Arg Lys Ser Tyr Lys His
1               5
```

(2) INFORMATION FOR SEQ ID NO: 5:

(i) SEQUENCE CHARACTERISTICS:
        (A) LENGTH:          16 amino acids
        (B) TYPE:            amino acid
        (C) STRANDEDNESS:    single
        (D) TOPOLOGY:        linear (ii) MOLECULE TYPE:         peptide (xi) SEQUENCE DESCRIPTION: SEQ ID NO: 5:

```
Met Ser Ser Val Lys Phe Val Ser Thr Thr Tyr Ser Gly Val Thr Arg
1               5                   10                  15
```